US006670432B1

(12) United States Patent
Timmers

(10) Patent No.: US 6,670,432 B1
(45) Date of Patent: *Dec. 30, 2003

(54) OLEFIN POLYMERS FORMED BY USE OF CONSTRAINED GEOMETRY ADDITION POLYMERIZATION CATALYSTS

(75) Inventor: Francis J. Timmers, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,414

(22) Filed: May 18, 2000

Related U.S. Application Data

(60) Division of application No. 08/799,749, filed on Feb. 12, 1997, now abandoned, which is a continuation of application No. 08/469,179, filed on Jun. 6, 1995, now abandoned, which is a continuation of application No. 07/545,403, filed on Jul. 3, 1990, which is a continuation-in-part of application No. 07/401,345, filed on Aug. 31, 1989, now abandoned, said application No. 08/799,749, is a continuation-in-part of application No. 07/520,168, filed on May 9, 1990, now abandoned, which is a continuation of application No. 07/436,524, filed on Nov. 14, 1989, now abandoned, said application No. 08/799,749, is a continuation-in-part of application No. 07/428,082, filed on Oct. 27, 1989, now abandoned, and a continuation-in-part of application No. 07/428,283, filed on Oct. 27, 1989, now abandoned, and a continuation-in-part of application No. 07/428,276, filed on Oct. 27, 1989, now abandoned, and a continuation-in-part of application No. 07/401,344, filed on Aug. 31, 1989, now abandoned.

(51) Int. Cl.$^7$ .......................... C08F 212/08; C08F 4/64; C08F 4/642
(52) U.S. Cl. .................. 526/160; 526/161; 526/347
(58) Field of Search ................. 526/347, 161, 526/160

(56) References Cited

U.S. PATENT DOCUMENTS

| 3,117,945 A | * | 1/1964 | Gorham et al. ............ 260/45.5 |
| 4,076,698 A | * | 2/1978 | Anderson et al. ......... 526/348.6 |
| 4,673,711 A | | 6/1987 | Sharps, Jr. et al. .......... 525/240 |
| 5,288,762 A | | 2/1994 | Park et al. .................... 521/79 |
| 5,340,840 A | | 8/1994 | Park et al. .................... 521/60 |
| 5,346,963 A | | 9/1994 | Hughes et al. ............... 525/285 |
| 5,460,818 A | | 10/1995 | Park et al. ................... 426/415 |
| 5,703,187 A | * | 12/1997 | Timmers ..................... 526/282 |

FOREIGN PATENT DOCUMENTS

| EP | 0416815 A2 | 3/1991 |
| EP | 0572990 A2 | 12/1993 |
| EP | 0739906 A1 | 10/1996 |
| JP | 07/278230 | 10/1995 |
| JP | 08/142443 | 6/1996 |
| WO | 95/03339 | 2/1995 |
| WO | 95/32095 | 11/1995 |

OTHER PUBLICATIONS

"First Technical Details on Some Next–Generation Polyolefins", *Plastics Technology*, Sep. 1992, p. 25.

Kurt W. Swogger, "Applications of Insite* Technology in the Rubber/Elastomer Market", *Worldwide Metallocene Conference MetCon '95*, May 17–19, 1995, Houston, Texas.

"Dow pairs ethylene, styrene", *Plastics News*, Jun. 26, 1995, p. 15.

"Metallocene Catalysts Initiate New Era in Polymer Synthesis", *Chemical & Engineering News*, Sep. 11, 1995, pp. 15–20.

Gerald Lancaster et al., "Applications of Insite* Technology in the Rubber/Elastomer Market", *Proceedings of Fifth International Business Forum on Specialty Polyolefins SPO '95*, Sep. 20–22, 1995, pp. 109–123.

"Dow Plots PP Course", *Chemical Week*, Strategies, Dec. 20/27, 1995, p. 8.

Y. W. Cheung et al., "Structure, Thermal Transitions and Mechanical Properties of Ethylene/Styrene Copolymers", *Proceeding of the SPE 54$^{th}$ Annual Technical Conference and Exhibits*, pp. 1634–1637, 1996.

C. P. Park et al., "Compatibilization of Polyethlene–Polystyrene Blends with Ethylene–Styrene Random Copolymers", *Proceeding of the SPE 54$^{th}$ Annual Technical Conference and Exhibits*, pp. 1887–1891.

"Metallocene Technology Drives New Materials", News Update, *Canadian Plastics*, Jan. 1996, vol. 54, No. 1, p. 8.

"Metallocenes yield ethylene–styene interpolymers", NEWSFOCUS, *Plastics Technology*, Jan. 1996, p. 13.

"Dow's plan's for '96: Become force in PP", *Plastics World*, Jan. 1996, pp. 12–13.

*Derwent Abstract 95–40100/51, Oct. 24, 1995 (JP 07278230).

Chemical Absract 122:240559v, Lu, Zejan, et al., "Synthesis structure and properties of styrene–ethylene copolymers", (Institute of Polymer Science, Zhongshan University, Guangzhou, 510275, 1994 (Translation).

International Search Report dated Oct. 6, 1997 issued by the European Patent Office acting as the International Search Authority in PCT/US96/14233.

* cited by examiner

Primary Examiner—Roberto Rabago

(57) ABSTRACT

Metal complexes having constrained geometry and a process for preparation thereof, addition polymerization catalysts formed therefrom, processes for preparation of such addition polymerization catalysts, methods of use, and novel polymers formed thereby, including ElPE resins and pseudo-random copolymers, are disclosed and claimed.

12 Claims, 17 Drawing Sheets

Ethylene/Styrene Pseudo-random Copolymer 9.0 Mole % Styrene, 15% Tail-to-Tail

Ethylene/Styrene Random Copolymer 37 Mole % Styrene, 15% Tail-to-Tail

OLEFIN POLYMERS FORMED BY USE OF CONSTRAINED GEOMETRY ADDITION POLYMERIZATION CATALYSTS

CROSS REFERENCE TO RELATED APPLICATIONS

This application is a divisional of application Ser. No. 08/799,749, filed Feb. 12$^{th}$, 1997, now abandoned, which is a Continuation of application Ser. No. 08/469,179, filed Jun. 6, 1995, now abandoned, which is a Continuation of application Ser. No. 07/545,403, filed Jul. 3, 1990, which is a Continuation-in-part of the following U.S. patent application Ser. No. 07/401,345, filed Aug. 31, 1989, now abandoned; Ser. No. 07/401,344, filed Aug. 31, 1989, now abandoned; Ser. No. 07/428,082, filed Oct. 27, 1989 now abandoned; Ser. No. 07/428,283, filed Oct. 27, 1989, now abandoned; Ser. No. 07/428,276, filed Oct. 27, 1989, now abandoned; and Ser. No. 07/520,168 filed May 9, 1990, now abandoned, which is a continuation of Ser. No. 07/436,524, filed Nov. 14, 1989, now abandoned, the teachings of all of which foregoing applications are incorporated herein in their entireties by reference thereto.

BACKGROUND OF THE INVENTION

The present invention relates to metal coordination complexes having constrained geometry. The invention also relates to certain novel addition polymerization catalysts comprising such metal complexes having constrained geometry. Furthermore, the invention relates to methods for the polymerization of addition polymerizable monomers and to the resulting polymers.

Because of the unique exposure of the active metal site of the metal coordination complexes having constrained geometry, catalysts resulting therefrom have unique properties. Under certain conditions, the catalysts of the invention are capable of preparing novel olefin polymers having previously unknown properties due to their unique facile abilities to polymerize α-olefins, diolefins, hindered vinylidene aliphatic monomers, vinylidene aromatic monomers and mixtures thereof.

Numerous metal coordination complexes are known in the art including such complexes involving monocyclopentadienyl groups and substituted monocyclopentadienyl groups. The present metal coordination complexes differ from those previously known in the art due to the fact that the metal is bound to a delocalized substituted π-bonded moiety in a manner so as to induce a constrained geometry about the metal. Preferably the metal is bound to a cyclopentadienyl, substituted cyclopentadienyl or similar group by both a η$^5$-bond and a bridging linkage including other ligands of the metal. The complexes also preferably include metals having useful catalytic properties.

Also previously known in the art are transition metal coordination complexes known as tucked complexes. Such complexes are described in *Organometallics* 6, 232–241 (1987).

In U.S. Ser. No. 07/008,800, filed Jan. 30, 1987, now abandoned, (published in equivalent form as EP 277,004) there are disclosed certain bis(cyclopentadienyl) metal compounds formed by reacting a bis(cyclopentadienyl) metal complex with salts of Bronsted acids containing a noncoordinating compatible anion. The reference discloses the fact that such complexes are usefully employed as catalysts in the polymerization of olefins. For the teachings contained therein U.S. Ser. No. 07/008,800, now abandoned, and EP 277,004 are herein incorporated in their entirety by reference thereto.

Previous attempts to prepare copolymers of vinylidene aromatic monomers and α-olefins, in particular copolymers or styrene and ethylene, have either failed to obtain substantial incorporation of the vinylidene aromatic monomer or else have achieved polymers of low molecular weight. In Polymer Bulletin, 20, 237–241 (1988) there is disclosed a random copolymer of styrene and ethylene containing 1 mole percent styrene incorporated therein. The reported polymer yield was $8.3 \times 10^{-4}$ grams of polymer per micromole titanium employed.

It has now been discovered that previously known addition polymerization catalysts are incapable of high activity and polymerization of numerous monomers because they lack constrained geometry.

It would be desirable if there were provided novel complexes of groups 3 (other than scandium), 4–10 and the lanthanides having constrained geometry.

Additionally it would be desirable if there were provided novel catalysts for addition polymerizations comprising novel complexes of groups 3 (other than scandium), 4–10 and the lanthanides having constrained geometry.

Furthermore, it would desirable if there were provided a process for the preparation of polymers of addition polymerizable monomers using novel catalysts comprising complexes of groups 3 (other than scandium), 4–10 and the lanthanides having constrained geometry.

Finally, it would be desirable if there were provided novel polymers of addition polymerizable monomers that may be prepared by an addition polymerization process using catalysts comprising novel complexes of groups 3 (other than scandium), 4–10 and the lanthanides having constrained geometry.

SUMMARY OF THE INVENTION

In one aspect the present invention relates to a metal coordination complex having constrained geometry. More particularly it relates to such coordination complexes that are usefully employed in combination with activating cocatalyst compounds or mixtures of compounds to form a catalytic system usefully employed in the polymerization of addition polymerizable monomers, especially ethylenically unsaturated monomers.

In another aspect the present invention relates to a process for preparing certain components of the above metal coordination complexes having constrained geometry and to the precursor compounds necessary therefor.

In yet another aspect the present invention relates to a process for preparing addition polymers, especially homopolymers and copolymers of olefins, diolefins, hindered aliphatic vinyl monomers, vinylidene aromatic monomers and mixtures of the foregoing and to the resulting polymer products.

According to the present invention there is provided a metal coordination complex comprising a metal of group 3 (other than scandium), 4–10 or the lanthanide series of the periodic table of the elements and a delocalized π-bonded moiety substituted with a constrain-inducing moiety, said complex having a constrained geometry about the metal atom such that the angle at the metal between the centroid of the delocalized, substituted π-bonded moiety and the center of at least one remaining substituent is less than such angle in a similar complex containing a similar π-bonded moiety lacking in such constrain-inducing substituent, and provided further that for such complexes comprising more than one delocalized, substituted π-bonded moiety, only one thereof for each metal atom of the complex is a cyclic, delocalized, substituted π-bonded moiety.

In addition there is provided a metal coordination complex corresponding to the formula:

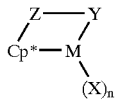

wherein:
M is a metal of group 3 (other than scandium), 4–10, or the lanthanide series of the periodic table of the elements;
Cp* is a cyclopentadienyl or substituted cyclopentadienyl group bound in an $\eta^5$ bonding mode to M;
Z is a moiety comprising boron, or a member of 30 group 14 of the periodic table of the elements, and optionally sulfur or oxygen, said moiety having up to 20 non-hydrogen atoms, and optionally Cp* and Z together form a fused ring system;
X independently each occurrence is an anionic ligand group or neutral Lewis base ligand group having up to 30 non-hydrogen atoms;
n is 0, 1, 2, 3, or 4 depending on the valence of M; and
Y is an anionic or nonanionic ligand group bonded to Z and M comprising nitrogen, phosphorus, oxygen or sulfur and having up to 20 non-hydrogen atoms, optionally Y and Z together form a fused ring system.

There is also provided according to the present invention a process for preparing a metal coordination complex corresponding to the foregoing formula I comprising the steps of:

A) contacting a metal compound of the formula $MX_{n+2}$ or a coordinated adduct thereof with a dianionic salt compound corresponding to the formula:

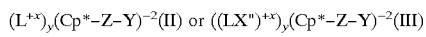

wherein:
L is a metal of group 1 or 2 of the periodic table of the elements,
X" is fluoro, chloro, bromo, or iodo,
x and y are either 1 or 2 and the product of x and y equals 2, and
M, X, Cp, R, and Y are as previously defined; and
B) recovering the resulting product.

Further there is provided a process for preparing a metal coordination complex corresponding to the foregoing formula I comprising the steps of:

A) contacting a metal compound of the formula $MX_{n+1}$ or a coordinated adduct thereof with a dianionic salt compound corresponding to the formulas II or III;
B) oxidizing the metal to a higher oxidation state by contacting the reaction product of step A) with a noninterfering oxidizing agent; and
C) recovering the resulting product.

There is also provided a catalyst useful in addition polymerizations comprising the following components:

a) a metal coordination complex comprising a metal of group 3 (other than scandium), 4–10 or the lanthanide series of the periodic table of the elements and a delocalized π-bonded moiety substituted with a constrain-inducing moiety, said complex having a constrained geometry about the metal atom such that the angle at the metal between the centroid of the delocalized, substituted π-bonded moiety and the center of at least one remaining substituent is less than such angle in a similar complex containing a similar π-bonded moiety lacking in such constrain-inducing substituent, and provided further that for such complexes comprising more than one delocalized, substituted π-bonded moiety, only one thereof for each metal atom of the complex is a cyclic, delocalized, substituted π-bonded moiety; and
b) an activating cocatalyst.

In a further embodiment of the present invention there is provided a catalyst useful in addition polymerizations comprising the following components:

a) a metal coordination complex corresponding to the formula I, and
b) an activating cocatalyst.

Even further according to the present invention there is provided a polymerization process comprising contacting one or more addition polymerizable monomers under addition polymerization conditions with a catalyst comprising:

a) a metal coordination complex comprising a metal of group 3 (other than scandium), 4–10 or the lanthanide series of the periodic table of the elements and a delocalized π-bonded moiety substituted with a constrain-inducing moiety, said complex having a constrained geometry about the metal atom such that the angle at the metal between the centroid of the delocalized, substituted π-bonded moiety and the center of at least one remaining substituent is less than such angle in a similar complex containing a similar π-bonded moiety lacking in such constrain-inducing substituent, and provided further that for such complexes comprising more than one delocalized, substituted π-bonded moiety, only one thereof for each metal atom of the complex is a cyclic, delocalized, substituted π-bonded moiety; and
b) an activating cocatalyst.

Further according to the present invention there is provided an addition polymerization process comprising the steps of:

A) contacting a mixture comprising one or more addition polymerizable monomers under polymerization conditions in the presence of a catalyst comprising a metal coordination complex corresponding to the formula I and an activating cocatalyst; and
B) recovering the resulting polymer.

Further still according to the present invention there is provided a polymer comprising in interpolymerized form one or more addition polymerizable monomers prepared by contacting an addition polymerizable monomer or mixture thereof under addition polymerization conditions with a catalyst comprising:

a) a metal coordination complex comprising a metal of group 3 (other than scandium), 4–10 or the lanthanide series of the periodic table of the elements and a delocalized π-bonded moiety substituted with a constrain-inducing moiety, said complex having a constrained geometry about the metal atom such that the angle at the metal between the centroid of the delocalized, substituted π-bonded moiety and the center of at least one remaining substituent is less than such angle in a similar complex containing a similar π-bonded moiety lacking in such constrain-inducing substituent, and provided further that for such complexes comprising more than one delocalized, substituted π-bonded moiety, only one thereof for each metal atom of the complex is a cyclic, delocalized, substituted π-bonded moiety; and b) an activating cocatalyst.

In a still further embodiment of the present invention there is provided a polymer comprising in polymerized form one or more addition polymerizable monomers prepared by contacting an addition polymerizable monomer or mixture thereof under addition polymerization conditions with a catalyst comprising the following components:

a) a metal coordination complex corresponding to the formula I and an activating cocatalyst.

In still further embodiments there are provided ElPE polymers which are highly elastic, interpolymers of ethylene and one or more olefins other than ethylene.

In addition there are provided pseudo-random interpolymers of an α-olefin, particularly ethylene and a vinylidene aromatic monomer, a hindered aliphatic vinylidene monomer, or a mixture thereof.

The complexes of the invention are usefully employed as catalysts for addition polymerization processes to prepare polymers that are useful as molded articles, films for packaging applications, and foams for cushioning applications; and in the modification of synthetic and naturally occuring resins. The complexes may also be used as catalysts for hydrogenations, catalytic cracking processes, and in other industrial applications.

DETAILED DESCRIPTION OF THE INVENTION

By use of the term "delocalized π-bonded moiety" is meant an unsaturated organic moiety, such as those comprising ethylenic or acetylenic functionality, wherein the π-electrons thereof are donated to the metal to form a bond. Examples include alkene-, alkenyl-, alkyne-, alkynyl-, allyl-, polyene-, and polyenyl-moieties as well as unsaturated cyclic systems.

By use of the term "constrained geometry" herein is meant that the metal atom is forced to greater exposure of the active metal site because of one or more substituents on the delocalized π-bonded moiety. Preferably the delocalized π-bonded moiety is a cyclopentadienyl or substituted cyclopentadienyl group forming a portion of a ring structure wherein the metal is both bonded to an adjacent covalent moiety and is held in association with the delocalized π-bonded moiety through $\eta^5$ bonds. It is understood that each respective bond between the metal atom and the constituent atoms of the delocalized π-bonded moiety need not be equivalent. That is the metal may be symetrically or unsymetrically π-bound to the π-bonded moiety.

The geometry of the active metal site is further defined as follows. The centroid of the π-bonded moiety may be defined as the average of the respective X, Y, and Z coordinates of the atomic centers forming the π-bonded moiety. The angle, Θ, formed at the metal center between the centroid of the π-bonded moiety and each other ligand of the metal complex may be easily calculated by standard techniques of single crystal X-ray diffraction. Each of these angles may increase or decrease depending on the molecular structure of the constrained geometry metal complex. Those complexes wherein one or more of the angles, θ, is less than in a similar, comparative complex differing only in the fact that the constrain-inducing substituent is replaced by hydrogen have constrained geometry for purposes of the present invention. Preferably one or more of the above angles, θ, decrease by at least 5% more preferably 7.5% compared to the comparative complex. Highly preferably, the average value of all bond angles, Θ, is also less than in the comparative complex. Most preferably the metal coordination complex having constrained geometry is in the form of a ring structure, ie. the constrain-inducing substituent is part of a ring system which includes the metal.

Preferably, monocyclopentadienyl metal coordination complexes of group 4 or lanthanide metals according to the present invention have constrained geometry such that the smallest angle, Θ, is less than 115°, more preferably less than 110°, most preferably less than 105°.

Illustrative atomic arrangements of complexes as determined from single crystal X-ray diffraction values are shown in FIGS. 1–7.

Figure 1:
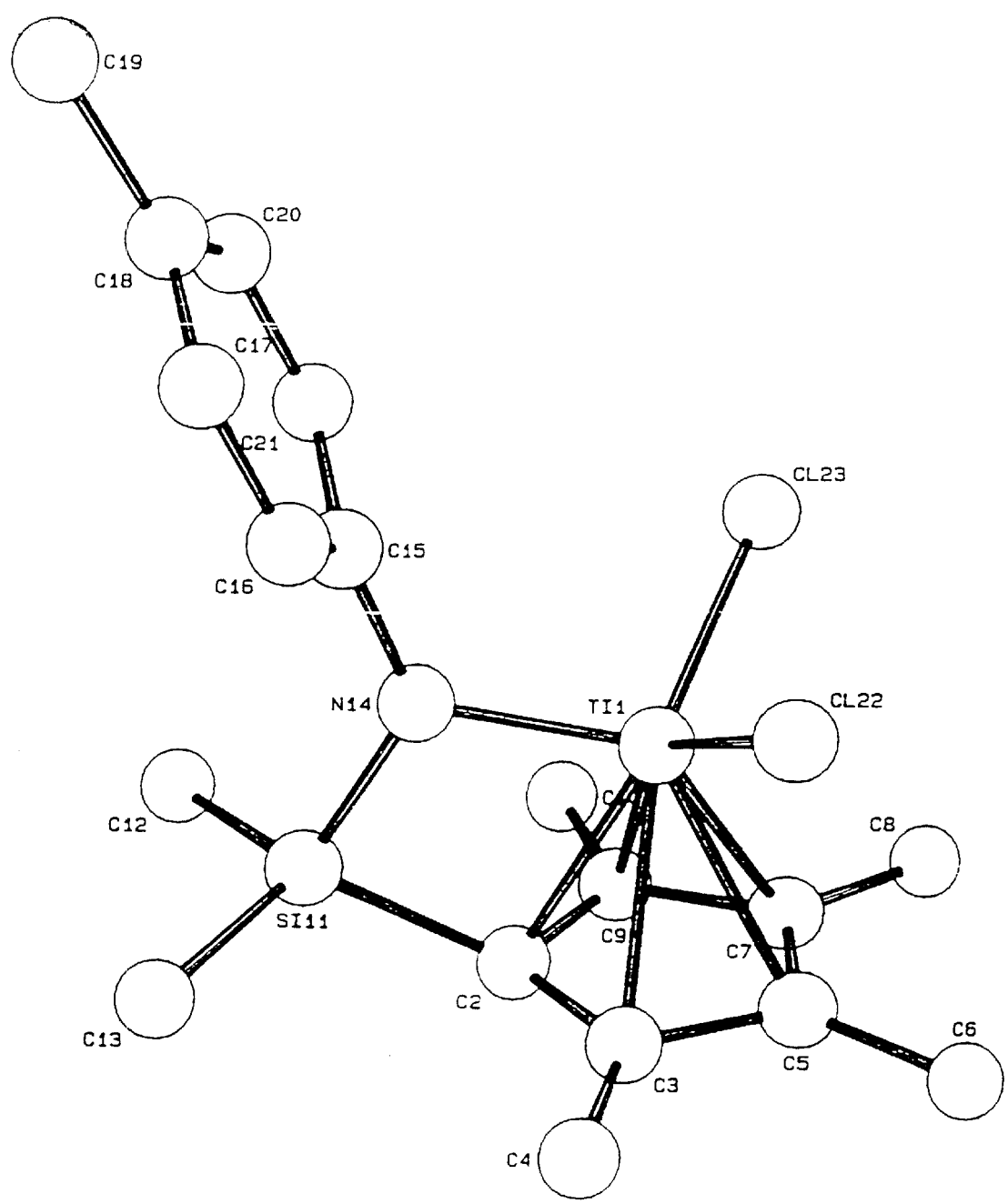
FIGS. 1–5 are computer generated models of constrained geometry complexes of the invention based on single crystal X-ray data.

FIG. 1 shows the single-crystal X-ray crystallographically determined structure of (4-methylphenylamido)dimethyl (tetramethyl-$\eta^5$-cyclopentadienyl)silanetitanium dichloride. The angle formed by the centroid of the cyclopentadienyl ring (C2, C3, C5, C7 and C9), the titanium atom (TI1), and the nitrogen atom (N14) is 105.7°.

Figure 2:
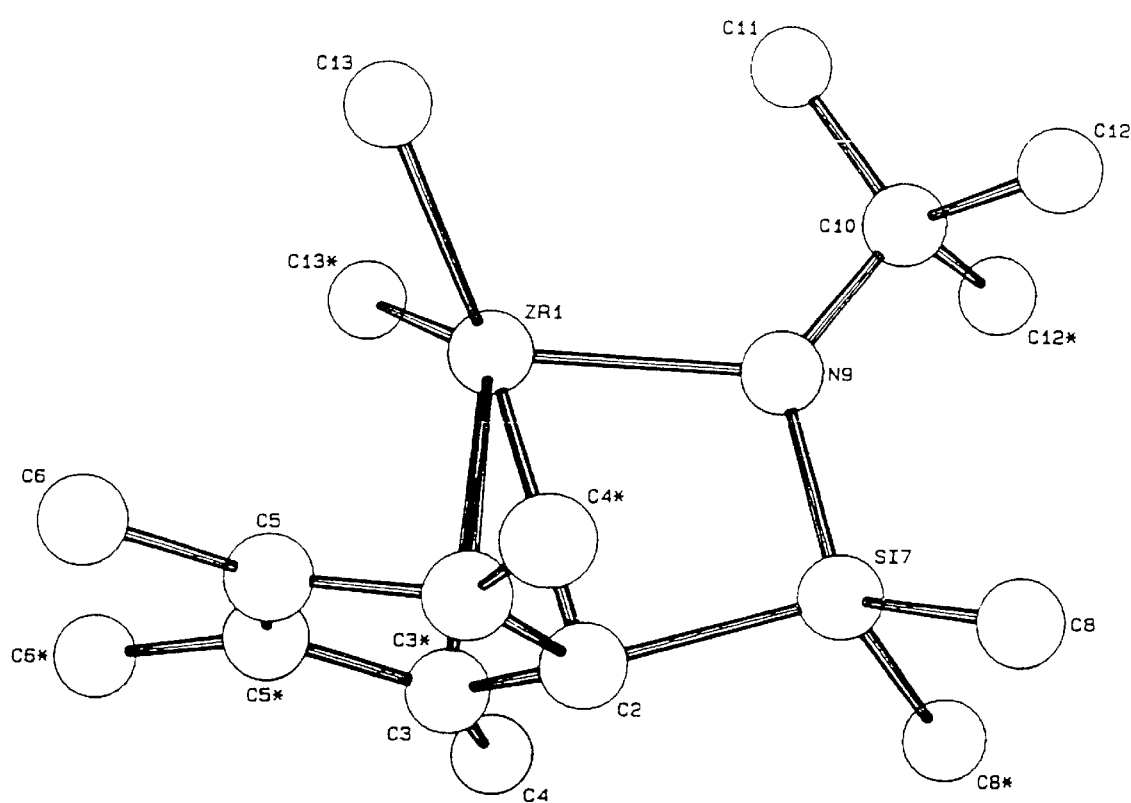

FIG. 2 shows the single-crystal X-ray crystallographically determined structure of (t-butylamido)dimethyl (tetramethyl-$\eta^5$-cyclopentadienyl)silanezirconium dimethyl. The angle formed by the centroid of the cyclopentadienyl ring (C2, C3, C3*, C5, and C5*), the zirconium atom (ZR1), and the nitrogen atom (N9) was determined to be 102.0°.

Figure 3:
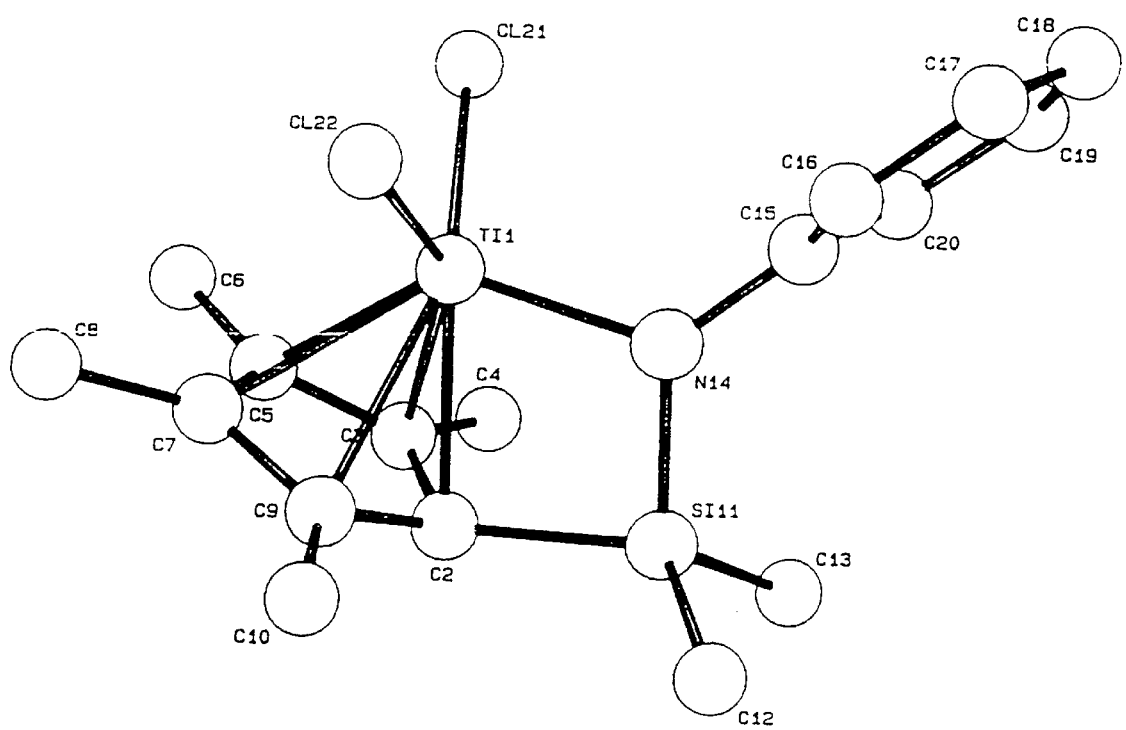

FIG. 3 shows the single-crystal X-ray crystallographically determined structure of (phenylamido)dimethyl (tetramethyl-$\eta^5$-cyclopentadienyl)silanetitanium dichloride. The angle formed by the centroid of the cyclopentadienyl ring (C2, C3, C5, C7, and C9), the titanium atom (TI1), and the nitrogen atom (N14) was determined to be 106.1°.

Figure 4:
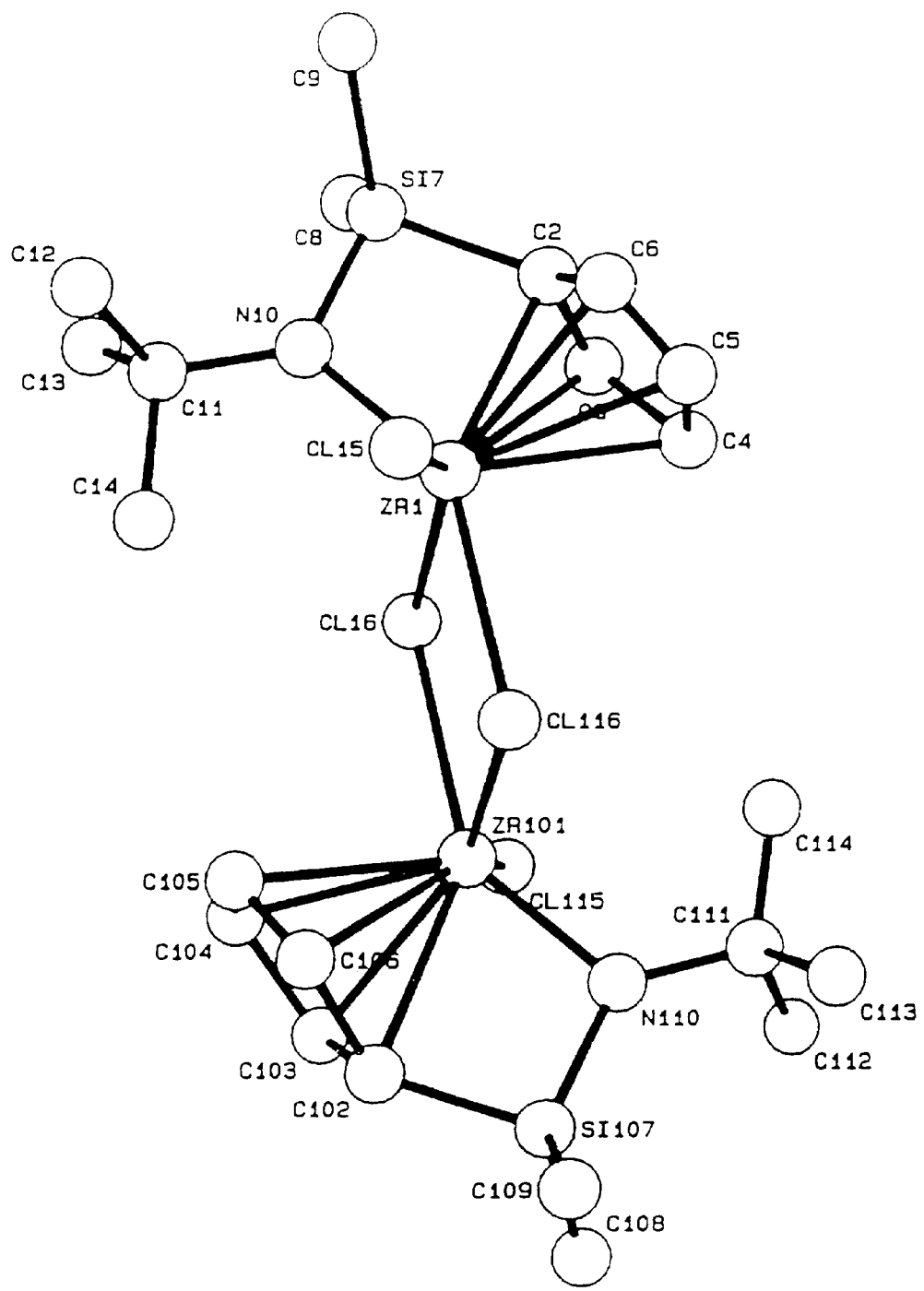

FIG. 4 shows the single-crystal X-ray crystallographically determined structure of (tert-butylamido)dimethyl($\eta^5$-cyclopentadienyl)silanezirconium dichloride. The structure shows that this molecule crystallizes as a dimer with 2 bridging chlorides. The angle formed by the centroid of the cyclopentadienyl ring (C2, C3, C4, C5, and C6), the zirconium atom (ZR1), and the nitrogen atom (N10), or the angle formed by the centroid of the cyclopentadienyl ring (C102, C103, C104, C105, and C106), the zirconium atom (ZR101), and the nitrogen atom (N110) were determined to be 99.1°.

Figure 5:
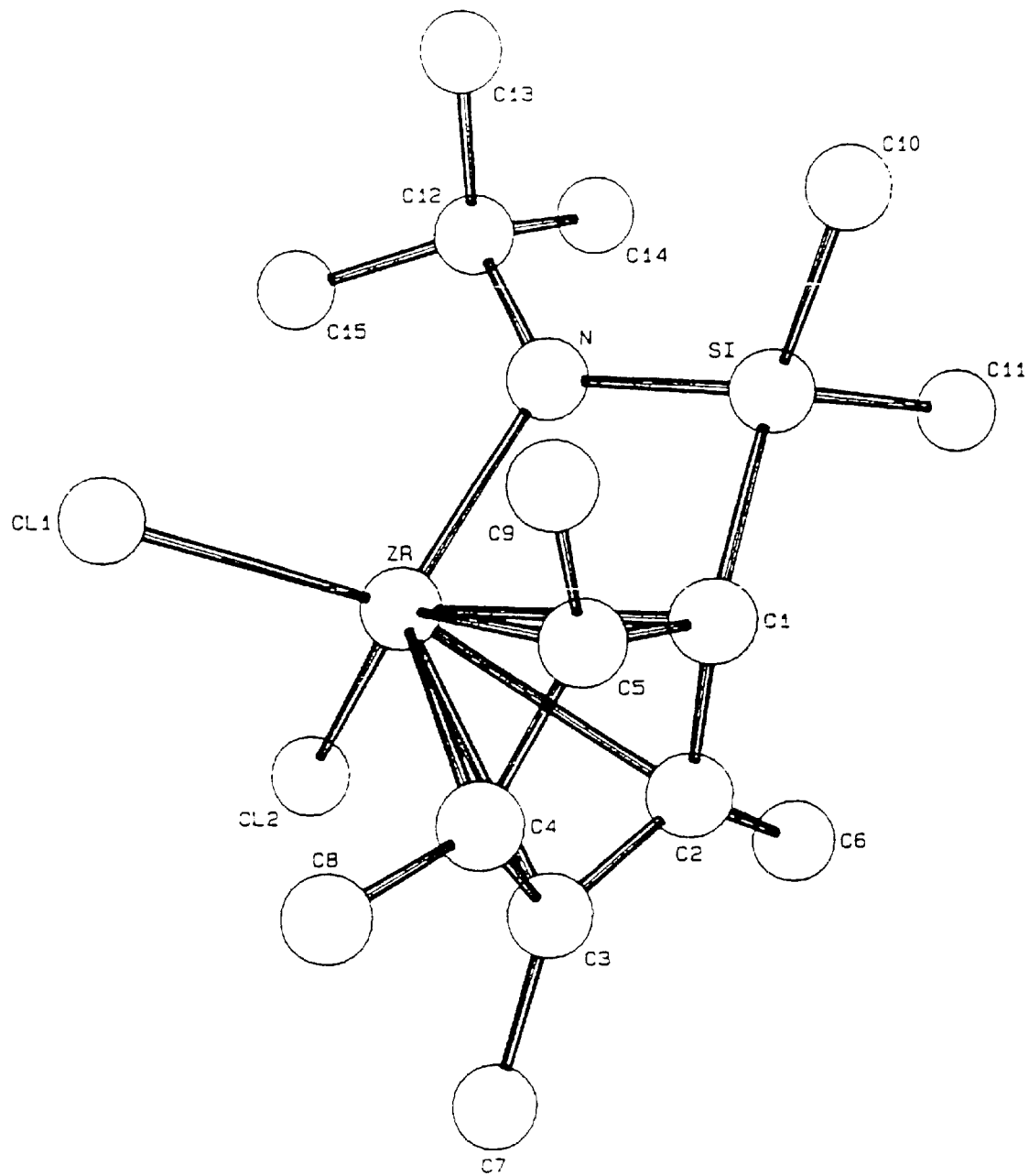

FIG. 5 shows the single-crystal X-ray crystallographically determined structure of (t-butylamido)dimethyl (tetramethyl-$\eta^5$-cyclopentadienyl)silanezirconium dichloride. The angle formed by the centroid of the cyclopentadienyl ring (C1, C2, C3, C4, and C5), the zirconium atom (ZR), and the nitrogen atom (N) was determined to be 102.0°.

Figure 6:
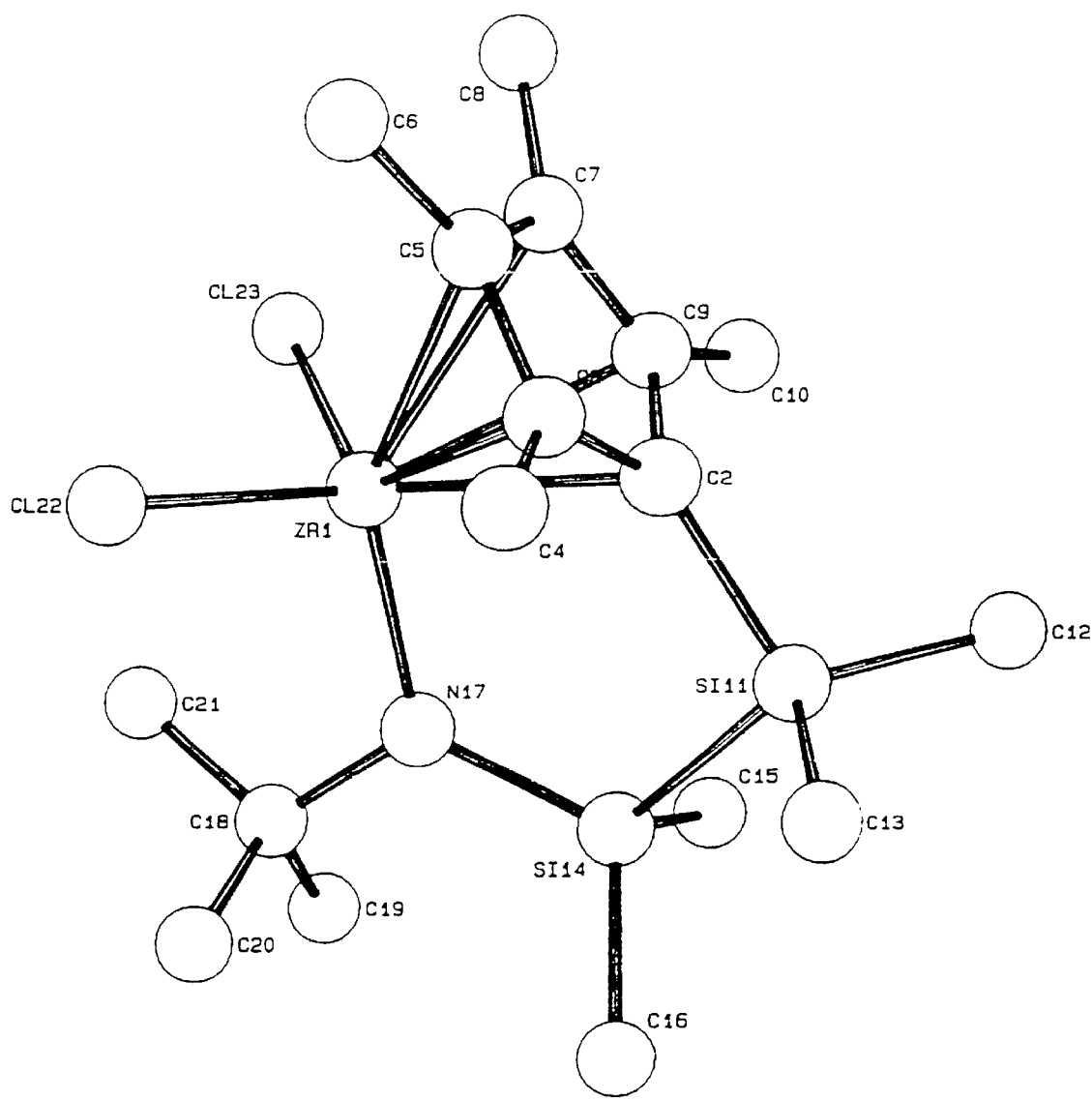
FIGS. 6 and 7 are computer generated models of metal complexes based on single crystal X-ray data showing less constrain- than those of FIGS. 1–5.

FIG. 6 shows the single-crystal X-ray crystallographically determined structure of (t-butylamido)tetramethyl (tetramethyl-$\eta^5$-cyclopentadienyl)disilanezirconium dichloride. The relatively long disilyl linking group that connects the cyclopentadienyl ring to the nitrogen atom of the amide ligand allows the nitrogen atom to be less constrained. The angle formed by the centroid of the cyclopentadienyl ring (C2, C3, C5, C7, and C9), the zirconium atom (ZR1), and the nitrogen atom (N17) was determined to be 118.0°. The activity of this catalyst towards olefin polymerization is considerably diminished relative to the analogous monosilane linking group in (tert-butylamido)dimethyl (tetramethyl-$\eta^5$-cyclopentadienyl)silanezirconium dichloride (FIG. 5).

Figure 7:
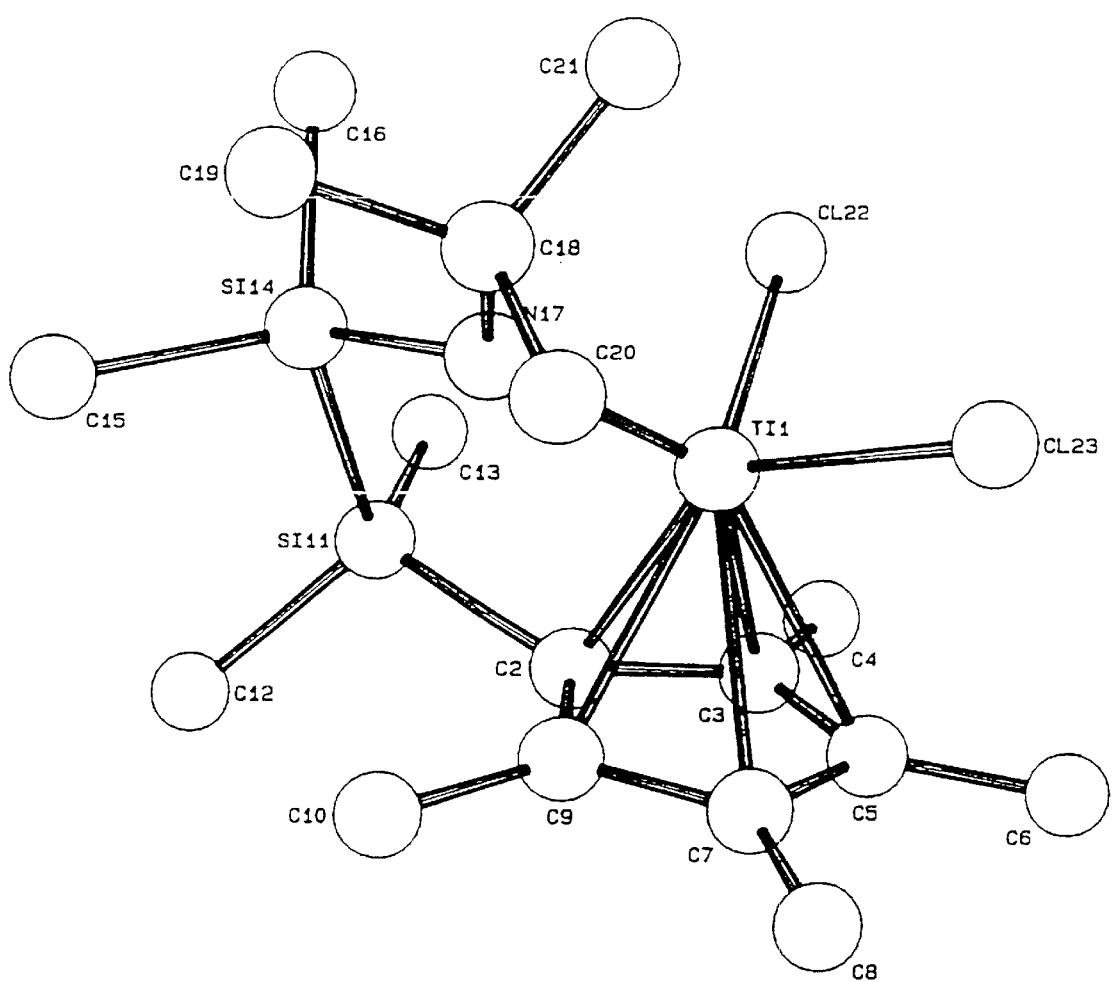
Figure 8:
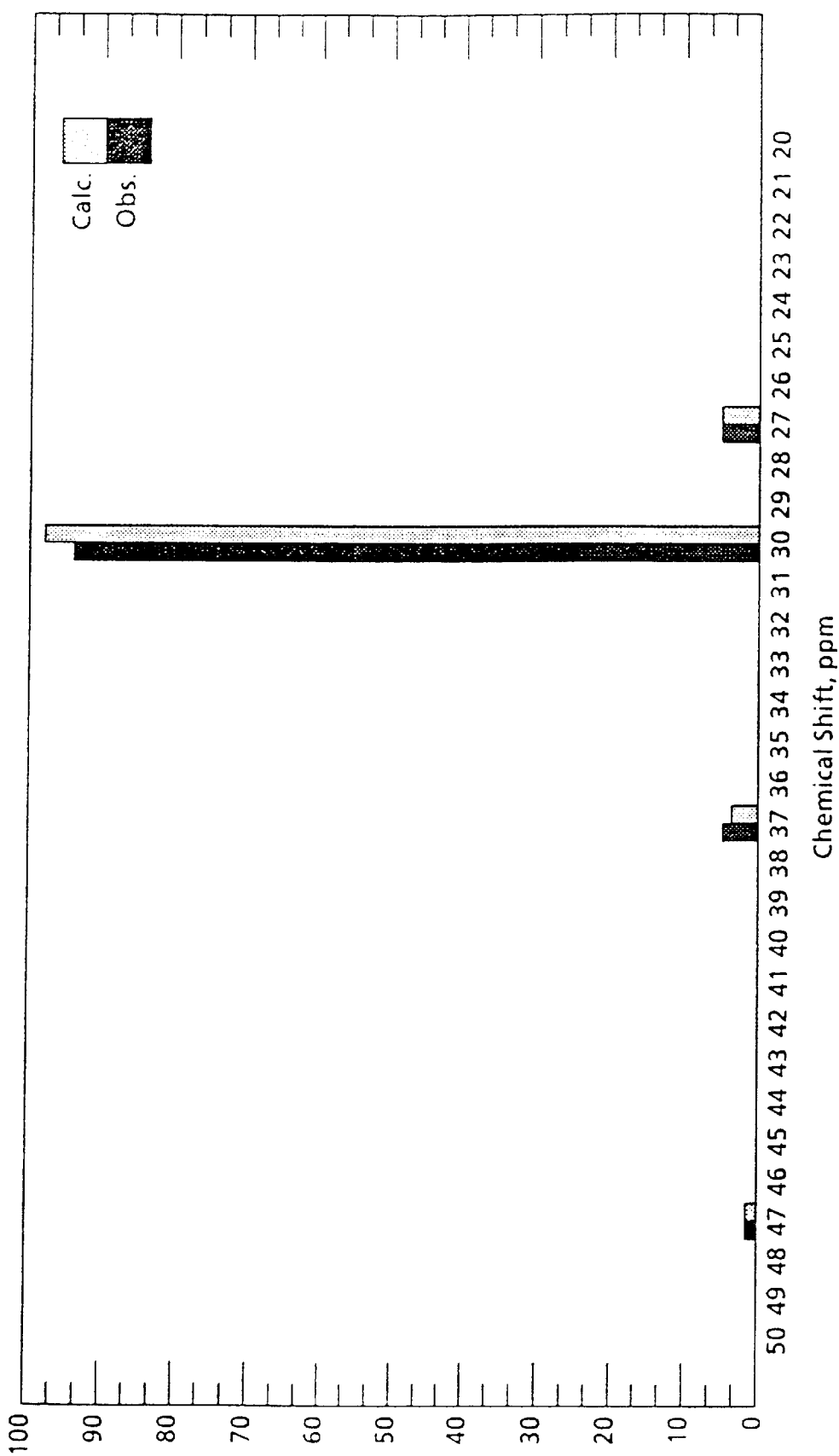
FIGS. 8–13 illustrate calculated and observed distribution of styrene, ethylene and reversed styrene units in ethylene/styrene copolymers observing pseudo-random incorporation rules according to the invention.
Figure 9:
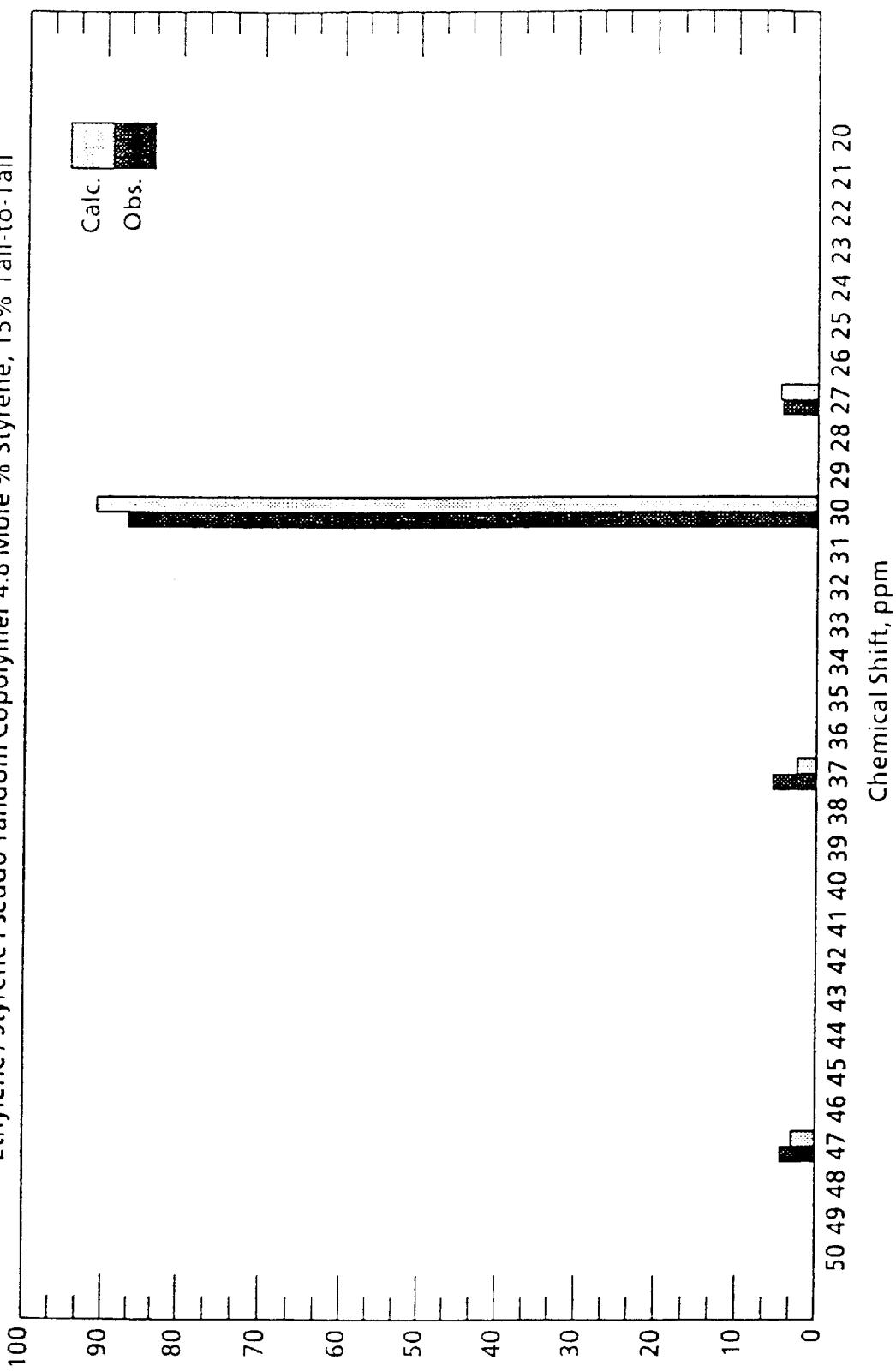
Figure 10:
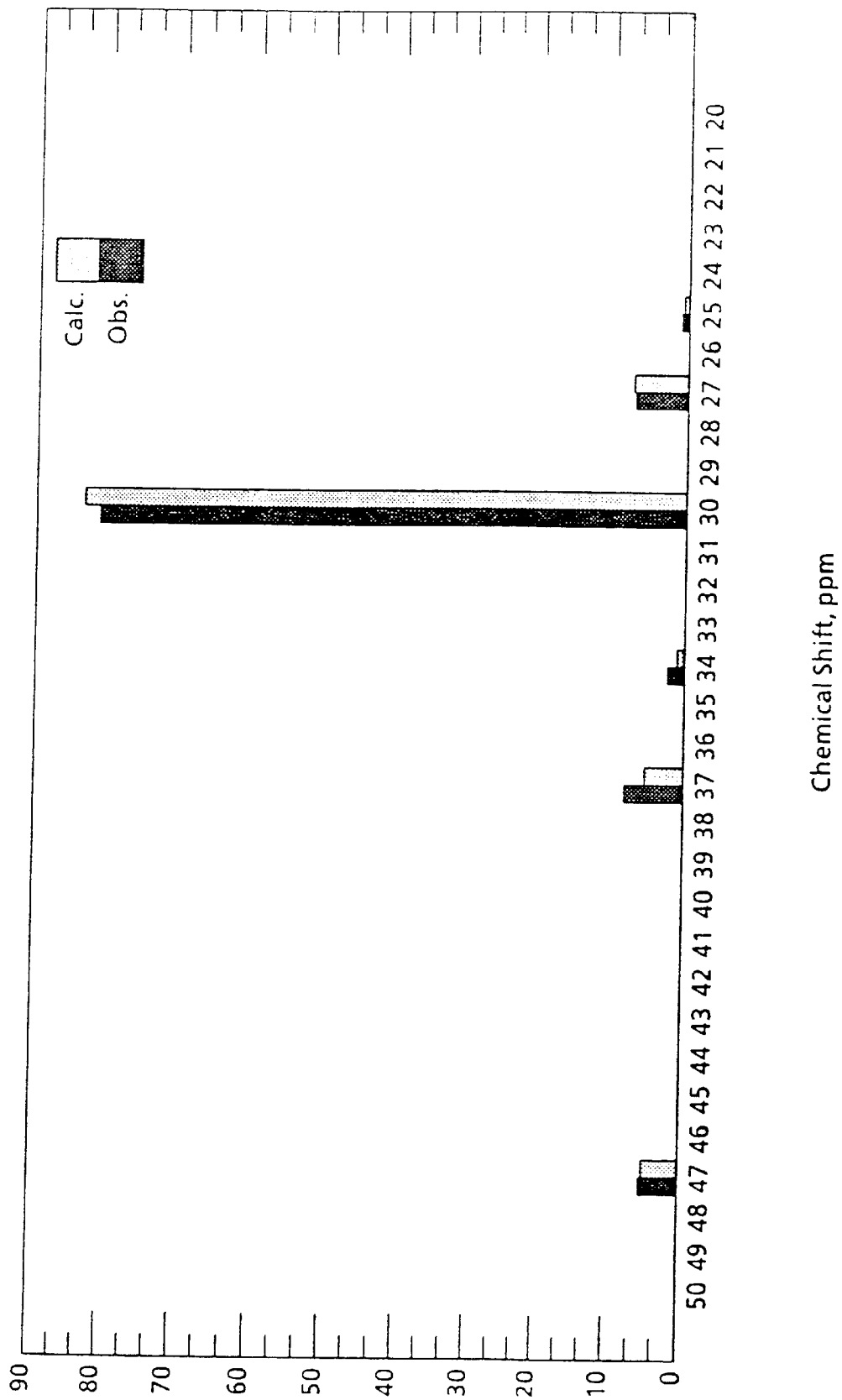
Figure 11:
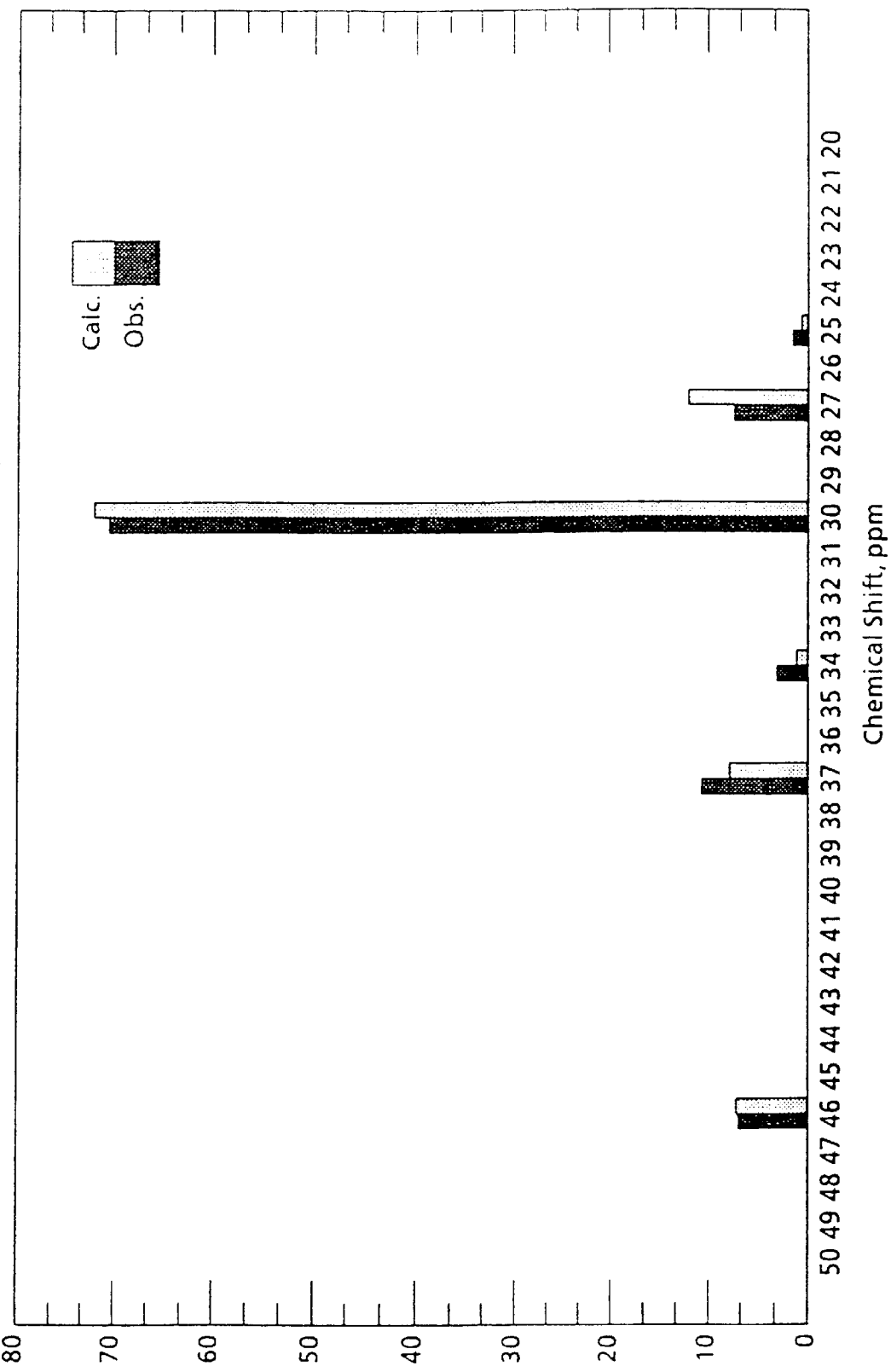
Figure 12:
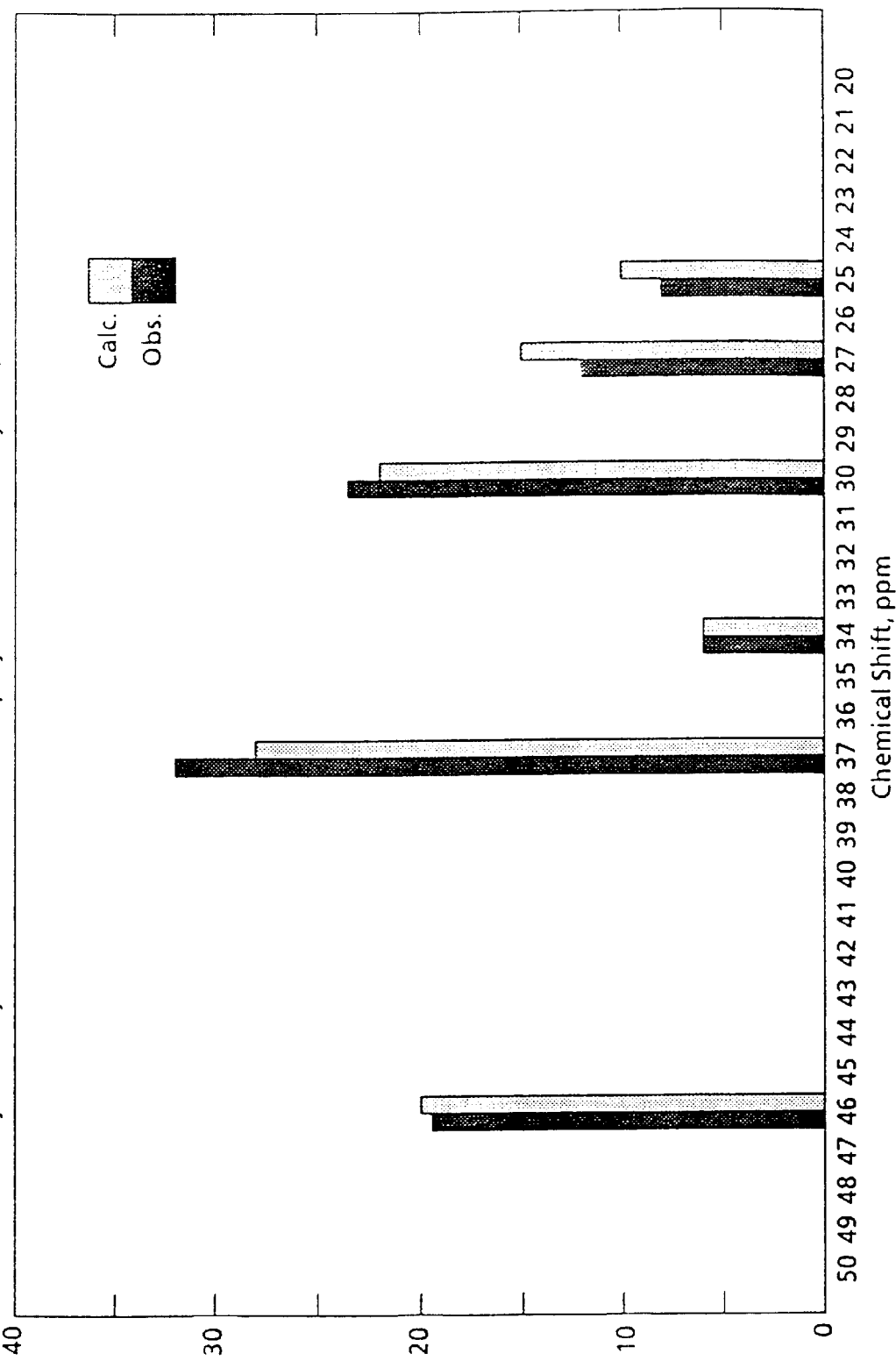
Figure 13:
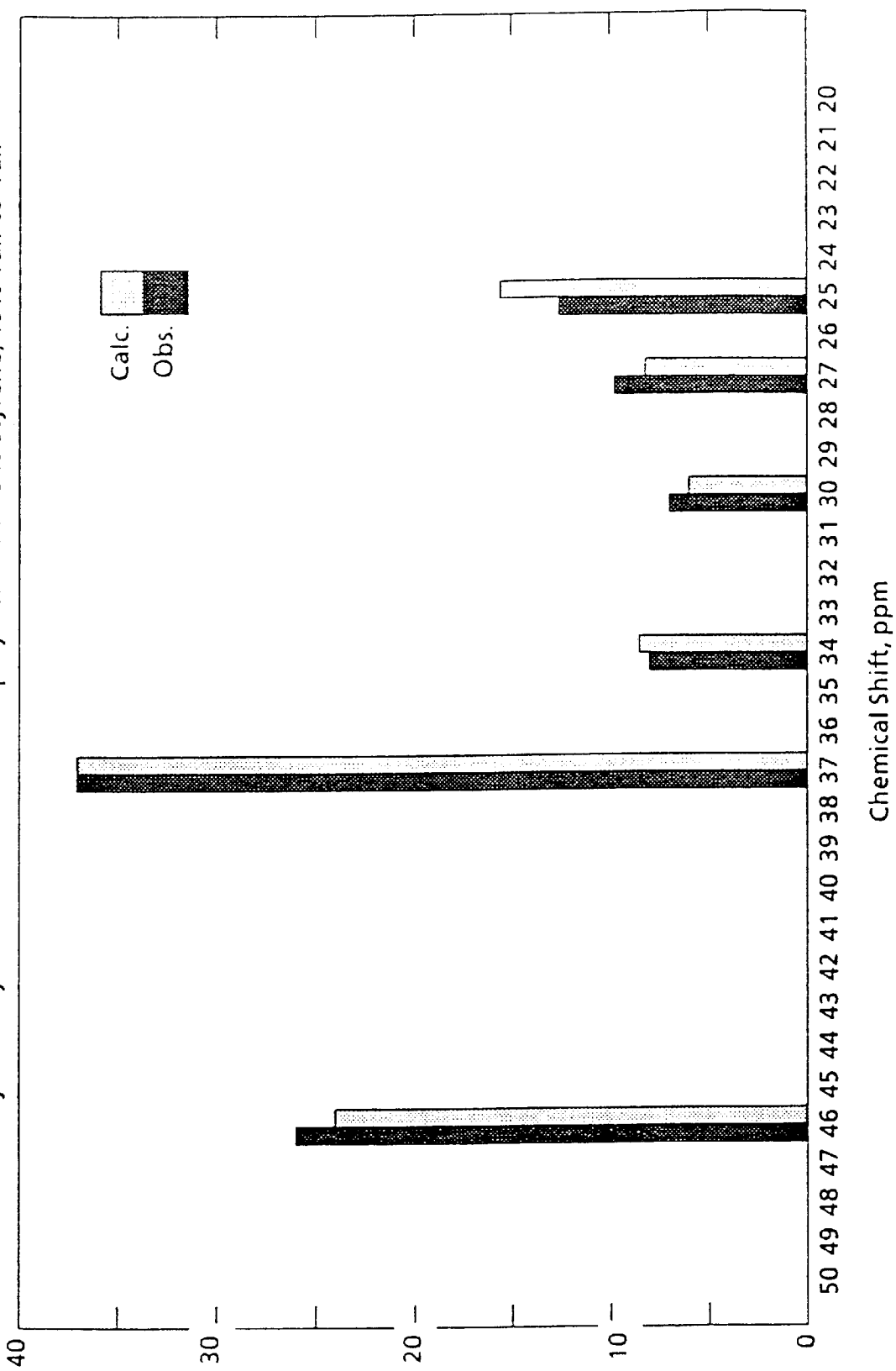

FIG. 7 shows the single-crystal X-ray crystallographically determined structure of (t-butylamido)tetramethyl (tetramethyl-$\eta^5$-cyclopentadienyl)disilanetitanium dichloride. The relatively long disilyl linking group that connects the cyclopentadienyl ring to the nitrogen atom of the amide ligand allows the nitrogen atom to be less constrained. The angle formed by the centroid of the cyclopentadienyl ring (C2, C3, C5, C7, and C9), the titanium atom (TI1), and the nitrogen atom (N17) was determined to be 120.5°. Accordingly, the activity of this catalyst towards olefin polymerization is considerably diminished relative to the analogous monosilane linking group in (t-butylamido) dimethyl(tetramethyl-$\eta^5$-cyclopentadienyl)silanetitanium dichloride.

The term "activating cocatalyst" as used herein refers to a secondary component of the catalyst able to cause the metal-containing complex to become effective as an addition polymerization catalyst or alternatively to balance the ionic charge of a catalytically activated species. Examples of the foregoing activating cocatalysts for use herein include aluminum compounds containing an Al—O bond such as the alkylaluminoxanes, especially methylaluminoxane; aluminum alkyls; aluminum halides; aluminum alkylhalides; Lewis acids; ammonium salts; noninterfering oxidizing agents, ie. silver salts, ferrocenium ions, etc.; and mixtures of the foregoing.

Particular techniques for the preparation of aluminoxane type compounds are disclosed in U.S. Pat. No. 4,542,119 the teachings of which are incorporated herein in their entirety by reference thereto. In a particularly preferred embodiment an aluminum alkyl compound is contacted with a regeneratable water-containing substance such as hydrated alumina, silica, or other substance. A process for preparing aluminoxane employing such regeneratable substance is disclosed in copending application Ser. No. 07/091,566, filed Aug. 31, 1987, now abandoned, and assigned to the same assignee as the present patent application.

Additional suitable activating cocatalysts include compounds corresponding to the formula:

$$AlR_nX''_{3-n}$$

wherein:

R is each occurrence $C_{1-10}$ alkyl or aralkyl;

X" is as previously defined; and n is 1, 2 or 3.

Most preferably such cocatalysts are trialkyl aluminum compounds, particularly triethyl aluminum.

"Addition polymerizable moromers" include for example ethylenically unsaturated monomers, acetylenic compounds, conjugated or nonconjugated dienes, polyenes, carbon monoxide, etc. Preferred monomers include the $C_{2-10}$ α-olefins especially ethylene, propylene, isobutylene, 1-butene, 1-hexene, 4-methyl-1-pentene, and 1-octene. Other preferred monomers include styrene, halo- or alkyl substituted styrene, vinyl chloride, acrylonitrile, methylmethacrylate, tetrafluoroethylene, methacrylonitrile, vinylidene chloride, vinylbenzocyclobutane, and 1,4-hexadiene.

By the term "hindered aliphatic vinylidene compounds" is meant addition polymerizable vinylidene monomers corresponding to the formula:

$$CG_2=CG'R''$$

wherein R" is an sterically bulky, aliphatic substituent of up to 20 carbons, G independently each occurrence is hydrogen or methyl, and G' independently each occurrence is hydrogen or methyl or alternatively G' and R" together form a ring system. By the term "sterically bulky" is meant that the monomer bearing this substituent is normally incapable of addition polymerization by standard Ziegler-Natta polymerization catalysts at a rate comparable with ethylene polymerizations. Preferred hindered aliphatic vinylidene compounds are monomers in which one of the carbon atoms bearing ethylenic unsaturation is tertiary or quaternary substituted. Examples of such substituents include cyclic aliphatic groups such as cyclohexyl, cyclohexenyl, cyclooctenyl, or ring alkyl or aryl substituted derivatives thereof, tert-butyl, norbornyl, etc. Most preferred hindered aliphatic vinylidene compounds are the various isomeric vinyl-ring substituted derivatives of cyclohexene and substituted cyclohexenes, and 5-ethylidene-2-norbornene. Especially suitable are 1-, 3-, and 4-vinylcyclohexene.

By the term "hindered vinylidene compound" is meant addition polymerizable vinylidene monomers corresponding to the formula:

$$CG_2=CG'R'''$$

wherein R'" is R" or an aryl substituent of up to 20 carbons, and G and G' are as previously defined. For example, in addition to hindered aliphatic vinylidene compounds, hindered vinylidene compounds also include the vinylidene aromatic monomers.

By the term "vinylidene aromatic monomers" is meant addition polymerizable compounds corresponding to the formula:

$$CG_2=C(G)-Ph$$

wherein G independently each occurrence is hydrogen or methyl and Ph is phenyl, or a halo- or $C_{1-4}$ alkyl-substituted phenyl group. Preferred vinylidene aromatic monomers are monomers corresponding to the above formula wherein G each occurrence is hydrogen. A most preferred vinylidene aromatic monomer is styrene.

By the term "α-olefin" is meant ethylene and the $C_{3-10}$ olefins having ethylenic unsaturation in the α-position. Preferred α-olefins are ethylene, propylene, 1-butene, isobutylene, 4-methyl-1-pentene, 1-hexene, and 1-octene, and mixtures thereof.

As used herein all reference to the Periodic Table of the Elements and groups thereof shall be to the version of the table published by the Handbook of Chemistry and Physics, CRC Press, 1987, utilizing the IUPAC system for naming groups.

Preferred metal coordination complexes are group 4 or Lanthanide based complexes. Further preferred complexes are those comprising a delocalized $\eta^5$ bonded group which is a cyclopentadienyl or substituted cyclopentadienyl group which forms a ring structure with the metal atom. Preferred delocalized π-bonded moieties are cyclopentadienyl-, indenyl-, and fluorenyl groups, and saturated derivatives thereof which form a ring structure with the metal atom. Each carbon atom in the cyclopentadienyl radical may be substituted or unsubstituted with the same or a different radical selected from the group consisting of hydrocarbyl radicals, substituted-hydrocarbyl radicals wherein one or more hydrogen atoms is replaced by a halogen atom, hydrocarbyl-substituted metalloid radicals wherein the metalloid is selected from Group 14 of the Periodic Table of the Elements, and halogen radicals. In addition two or more such substituents may together form a fused ring system. Suitable hydrocarbyl and ubstituted-hydrocarbyl radicals, which may be substituted for at least one hydrogen atom in the cyclopentadienyl radical, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Suitable organometalloid radicals include mono-, di- and trisubstituted organometalloid radicals of Group 14 elements wherein each of the hydrocarbyl groups contain from 1 to about 20 carbon atoms. More particularly, suitable organometalloid radicals include trimethylsilyl, triethylsilyl, ethyldimethylsilyl, methylciethylsilyl, phenyldimethylsilyl, methyldiphenylsilyl, triphenylsilyl, triphenylgermyl, trimethylgermyl and the like.

In the previously disclosed Formula I, suitable anionic ligand groups, X, are illustratively selected from the group consisting of hydride, halo, alkyl, silyl, germyl, aryl, amide, aryloxy, alkoxy, phosphide, sulfide, aceyl, pseudo halides such as cyanide, azide, etc., acetylacetonate, etc., or a combination thereof.

As previously mentioned, the complexes according to the present invention preferably comprise structures having altered or enhanced catalytic activity at the metal site when the complex is combined with a cocatalyst. In this regard electron donating substituents have been found to improve the catalytic properties of the complexes. That is, even though certain of the complexes do not possess constrained geometry, the same never-the-less possess catalytic properties, alone or in combination with activating substances.

A highly preferred metal coordination complex corresponds to the formula:

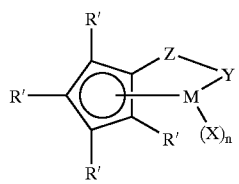

wherein R' each occurrence is independently selected from the group consisting of hydrogen, alkyl, aryl, silyl, germyl, cyano, halo and combinations thereof having up to 20 non-hydrogen atoms;

X each occurrence independently is selected from the group consisting of hydride, halo, alkyl, aryl, silyl, germyl, aryloxy, alkoxy, amide, siloxy, neutral Lewis base ligands and combinations thereof having up to 20 non-hydrogen atoms;

Y is —O—, —S—, —NR*—, —PR*—, or a neutral two electron donor ligand selected from the group consisting of OR*, SR*, NR*$_2$, or PR*$_2$;

M is a previously defined; and

Z is SiR*$_2$, CR *$_2$, SiR*$_2$SiR*$_2$, CR*$_2$CR*$_2$, CR*=CR*, CR*$_2$SiR*$_2$, GeR*$_2$, BR*, BR*$_2$; wherein:

R* each occurrence is independently selected from the group consisting of hydrogen, alkyl, aryl, silyl, halogenated alkyl, halogenated aryl groups having up to 20 non-hydrogen atoms, and mixtures thereof, or two or more R* groups from Y, Z, or both Y and Z form a fused ring system.

It should be noted that whereas formula I and the following formulas indicate a cyclic structure for the catalysts, when Y is a neutral two electron donor ligand, the bond between M and Y is more accurately referred to as a coordinate-covalent bond. Also, it should be noted that the complex may exist as a dimer or higher oligomer.

Further preferably, at least one of R', Z, or R* is an electron donating moiety. Thus, highly preferably Y is a nitrogen or phosphorus containing group corresponding to the formula —N(R"")— or —P(R"")—, wherein R"" is $C_{1-10}$ alkyl or aryl, ie. an amido or phosphido group.

Most highly preferred complex compounds are amidosilane- or amidoalkanediyl-compounds corresponding to the formula:

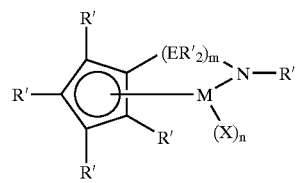

wherein:

M is titanium, zirconium or hafnium, bound in an $\eta^5$ bonding mode to the cyclopentadienyl group;

R' each occurrence is independently selected from the group consisting of hydrogen, silyl, alkyl, aryl and combinations thereof having up to 10 carbon or silicon atoms;

E is silicon or carbon;

X independently each occurrence is hydride, halo, alkyl, aryl, aryloxy or alkoxy of up to 10 carbons;

m is 1 or 2; and n is 1 or 2 depending on the valence of M.

Examples of the above most highly preferred metal coordination compounds include compounds wherein the R' on the amido group is methyl, ethyl, propyl, butyl, pentyl, hexyl, (including isomers), norbornyl, benzyl, phenyl, etc.; the cyclopentadienyl group is cyclopentadienyl, indenyl, tetrahydroindenyl, fluorenyl, octahydrofluorenyl, etc.; R' on the foregoing cyclopentadienyl groups each occurrence is hydrogen, methyl, ethyl, propyl, butyl, pentyl, hexyl, (including isomers), norbornyl, benzyl, phenyl, etc.; and X is chloro, bromo, iodo, methyl, ethyl, propyl, butyl, pentyl, hexyl, (including isomers), norbornyl, benzyl, phenyl, etc.

Specific compounds include: (tert-butylamido)(tetramethyl-$\eta^5$-cyclopentadienyl)-1,2-ethanediylzirconium dichloride, (tert-butylamido)(tetramethyl-$\eta^5$-cyclopentadienyl)-1,2-ethanediyltitanium dichloride, (methylamido)(tetramethyl-$\eta^5$-cyclopentadienyl)-1,2-ethanediylzirconium dichloride, (methylamido)(tetramethyl-$\eta^5$-cyclopentadienyl)-1,2-ethanediyltitanium dichloride, (ethylamido)(tetramethyl-$\eta^5$-cyclopentadienyl)-methylenetitanium dichloro, (tert-butylamido)dibenzyl(tetramethyl-$\eta^5$-cyclopentadienyl)silanezirconium dibenzyl, (benzylamido)dimethyl(tetramethyl-$\eta^5$-cyclopentadienyl)silanetitanium dichloride, (phenylphosphido)dimethyl(tetramethyl-$\eta^5$-cyclopentadienyl)silanezirconium dibenzyl, and the like.

The complexes are prepared by contacting the metal reactant and a group I metal derivative or Grignard derivative of the cyclopentadienyl compound in a solvent and separating the salt byproduct. Suitable solvents for use in preparing the metal complexes are aliphatic or aromatic liquids such as cyclohexane, methylcyclohexane, pentane, hexane, heptane, tetrahydrofuran, diethyl ether, benzene, toluene, xylene, ethylbenzene, etc., or mixtures thereof.

In a preferred embodiment, the metal compound is $MX_{n+1}$, ie. M is in a lower oxidation state than in the corresponding compound, $MX_{n+2}$ and the oxidation state of M in the desired final complex. A noninterfering oxidizing agent may thereafter be employed to raise the oxidation state of the metal. The oxidation is accomplished merely by contacting the reactants utilizing solvents and reaction conditions used in the preparation of the complex itself. By the term "noninterfering oxidizing agent" is meant a compound having an oxidation potential sufficient to raise the metal oxidation state without interfering with the desired complex formation or subsequent polymerization processes. A particularly suitable noninterfering oxidizing agent is AgCl.

In order to assist in the handling of the metal compounds employed in the present process corresponding to the formula $MX_{n+2}$, it may be beneficial first to form a solid adduct thereof by the use of a suitable coordinating agent according to well known techniques in the art. For example, whereas titanium tetrachloride is a fuming liquid which is difficult to handle, one may first form an adduct of $TiCl_4$ with an ether, tertiary amine, tertiary phosphine or other basic nonprotic compound. The resulting solids may be more easily handled. A preferred coordinating adduct is tetrahydrofuran.

The reactions employed in preparing the metal complex may be conducted either heterogeneously or homogeneously. That is, the various reactants or the resulting product need not be substantially soluble in the solvent mixture. Generally the reactants are contacted under an inert atmosphere for a time from several minutes to several days. Agitation may be employed if desired. The temperature of the reaction is generally from −90° C. to 150° C., preferably from −20° C. to 70° C.

Suitable catalysts for use according to the present invention are prepared by combining the metal coordination compound and activating cocatalyst compound in any order and in any suitable manner. Preferably the ratio of the coordination complex and cocatalyst on a molar basis is from about 1:0.1 to about 1:10,000. It will, of course, be appreciated that the catalyst system may also be formed in situ if the components thereof are added directly to the polymerization process and a suitable solvent or diluent, including condensed monomer, is used in said polymerization process. Suitable solvents include toluene, ethylbenzene, alkanes and mixtures thereof. In certain cases the catalysts may be isolated from solution and retained under inert atmosphere prior to use. The catalysts' components are sensitive to both moisture and oxygen and should be handled and transferred in an inert atmosphere such as nitrogen, argon or helium or under vacuum.

The polymerization is conducted according to known techniques for Ziegler-Natta or Kaminsky-Sinn type polymerizations. That is, the monomer(s) and catalyst are contacted at a temperature from −30° C. to 250° C., at reduced, elevated or atmospheric pressures. The polymerization is conducted under an inert atmosphere which may be a blanketing gas such as nitrogen, argon, hydrogen, ethylene, etc. or under vacuum. Hydrogen may additionally be utilized in the control of molecular weight through chain termination as is previously known in the art. The catalyst may be used as is or supported on a suitable support such as alumina, $MgCl_2$ or silica to provide a heterogeneous supported catalyst. A solvent may be employed if desired. Suitable solvents include toluene, ethylbenzene, and excess vinylidene aromatic or olefin monomer. The reaction may also be conducted under solution or slurry conditions, in a suspension utilizing a perfluorinated hydrocarbon or similar liquid, in the gas phase, ie. utilizing a fluidized bed reactor, or in a solid phase powder polymerization. A catalytically effective amount of the present catalyst and cocatalyst are any amounts that successfully result in formation of polymer. Such amounts may be readily determined by the routine experimentation by the skilled artisan. Preferred amounts of catalyst and cocatalyst are sufficient to provide an equivalent ratio of addition polymerizable monomer:catalyst of from $1\times10^{10}$:1 to 100:1, preferably from $1\times10^8$:1 to 500:1, most preferably $1\times10^6$:1 to 1000:1. The cocatalyst is generally utilized in an amount to provide an equivalent ratio of cocatalyst:catalyst from 10,000:1 to 0.1:1, preferably from 1,000:1 to 1:1.

It is to be understood that the metal complex may undergo various transformations or form intermediate species prior to and during the course of a polymerization. Thus other precursors could possibly be conceived to achieve the same catalytic species as are herein envisioned without departing from the scope of the present invention.

The resulting polymeric product is recovered by filtering or other suitable technique. Additives and adjuvants may be incorporated in the polymers of the present invention in order to provide desirable characteristics. Suitable additives include pigments, UV stabilizers, antioxidants, blowing agents, lubricants, plasticizers, photosensitizers, and mixtures thereof.

In the preparation of copolymers containing vinylidene aromatic or hindered aliphatic vinyl monomers it is desirable that a comonomer that is an α-olefin that is not particularly sterically hindered also be employed. Without wishing to be bound by any particular theory of operation, it is believed this is because the active site becomes crowded with the incorporation of the hindered vinyl compound making it unlikely that another hindered vinyl compound could enter into the polymerization as the next monomer in the sequence. After the incorporation of one or more olefins other than a hindered vinyl compound the active site once again becomes available for inclusion of a hindered vinyl monomer. On a limited basis however, the vinylidenearomatic monomer or sterically hindered vinyl monomer may insert into the polymer chain in reverse order, ie. so as to result in two methylene groups between the substituted polymer backbone moiety.

Preferably such polymers possess a Mw of greater than 13,000, more preferably greater than 20,000 and most preferably greater than 30,000. Also preferably such polymers possess a melt index ($I_2$), ASTM D-1238 Procedure A, condition E, of less than 125, more preferably from 0.01–100 and most preferably from 0.1 to 10.

Due to the use of the previously mentioned catalyst system comprising a coordination complex having constrained geometry, copolymers may be prepared that incorporate relatively bulky or hindered monomers in substantially random manner at low concentrations, and at higher concentrations according to an ordered insertion logic. The copolymers of α-olefins, especially ethylene and a hindered aliphatic vinylidene compound or vinylidene aromatic monomer can further be described as "pseudo-random". That is, the copolymers lack well defined blocks of either monomer, however the respective monomers are limited to insertion according to certain rules.

These rules were deduced from certain experimental details resulting from an analysis of the polymers. The polymers were analyzed by $^{13}$C NMR spectroscopy at 130° C. with a Varian VXR-300 spectrometer at 75.4 MHz. Samples of 200 to 250 mg polymer were dissolved in 15 mL of hot o-dichlorobenzene/1,1,2,2-tetrachloroethane-$d_2$ (approximately 70/30, v/v) which was approximately 0.05 M in chromium (III) tris(acetylacetonate) and a portion of the resulting solution was added to a 10 mm NMR tube. The following parameters and conditions were used: spectral width, 16,500 Hz; acquisition time 0.090 s; pulse width, 36°; delay, 1.0 s with the decoupler gated off during the delay,; FT size 32K; number of scans, >30,000; line broadening, 3 Hz. Spectra, as recorded were referenced to tetrachloroethane-$d_2$ (δ 73.77 ppm, TMS scale).

Therefor, without wishing to be bound by any particular theory, the results of the foregoing experimental procedures indicate that a particular distinguishing feature of pseudo-random copolymers is the fact that all phenyl or bulky hindering groups substituted on the polymer backbone are separated by 2 or more methylene units. In other words, the polymers comprising a hindered monomer of the present invention can be described by the following general formula (using styrene as the hindered monomer for illustration):

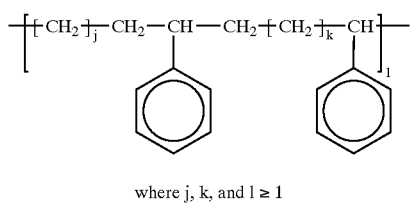

where j, k, and l ≥ 1

In further explanation of the foregoing experimental and theoretical results, and without wishing to be bound by any particular theory it can be concluded that during the addition polymerization reaction employing the present catalysts, if a hindered monomer is inserted into the growing polymer chain, the next monomer inserted must be ethylene or a hindered monomer which is inserted in an inverted or "tail-to-tail" fashion. This is illustrated below for a hindered vinyl monomer where M is the catalyst metal center, HG is a hindering group, and P is the growing polymer chain:

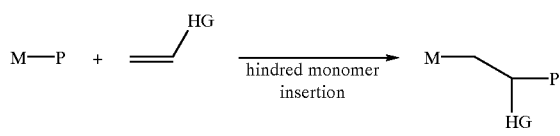

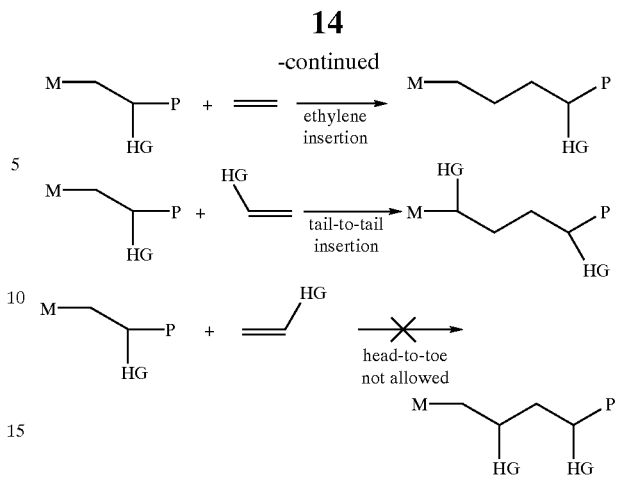

During the polymerization reaction, ethylene may be inserted at any time. After an inverted or "tail-to-tail" hindered monomer insertion, the next monomer must be ethylene, as the insertion of another hindered monomer at this point would place the hindering substituent closer together than the minimum separation as described above. A consequence of these polymerization rules is the catalysts of this invention do not homopolymerize styrene to any appreciable extent, while a mixture of ethylene and styrene is rapidly polymerized and may give high styrene content (up to 50 mole % styrene) copolymers.

As a further illustration of the description of the α-olefin/hindered monomer copolymer of the present invention, a computer model of the polymerization reaction was used to calculate the expected $^{13}$C NMR spectrum of the polymer product. The computer program utilized a random number generator to select either α-olefin or hindered monomer to be inserted into a growing polymer chain, then calculated the number of each type of $^{13}$C NMR signals resulting from that insertion. Polymers were computer generated by repeating this process for 10,000 or more monomer insertions, and the resulting calculated $^{13}$C NMR spectrum was compared to actual experimental $^{13}$C NMR spectra for pseudo-random ethylene/styrene copolymers of the invention.

Computer simulations of the polymer and resulting $^{13}$C NMR spectra of the calculated pseudo-random ethylene/styrene copolymers were performed using the constraint that if styrene monomer were inserted into the growing polymer chain, the next monomer inserted must be ethylene or a styrene which is inserted in an inverted or "tail-to-tail" fashion. Optimum fits between experimental and calculated spectra were obtained if approximately 15% of the styrene insertions are in the "tail-to-tail" manner. The observed and calculated $^{13}$C NMR spectra for such pseudo-random ethylene/styrene copolymers containing 1.4, 4.8, 9.0, 13, 37, and 47 mole percent styrene are shown in FIGS. 8–13. In each case, the observed and calculated spectra are in excellent agreement.

Figure 14:
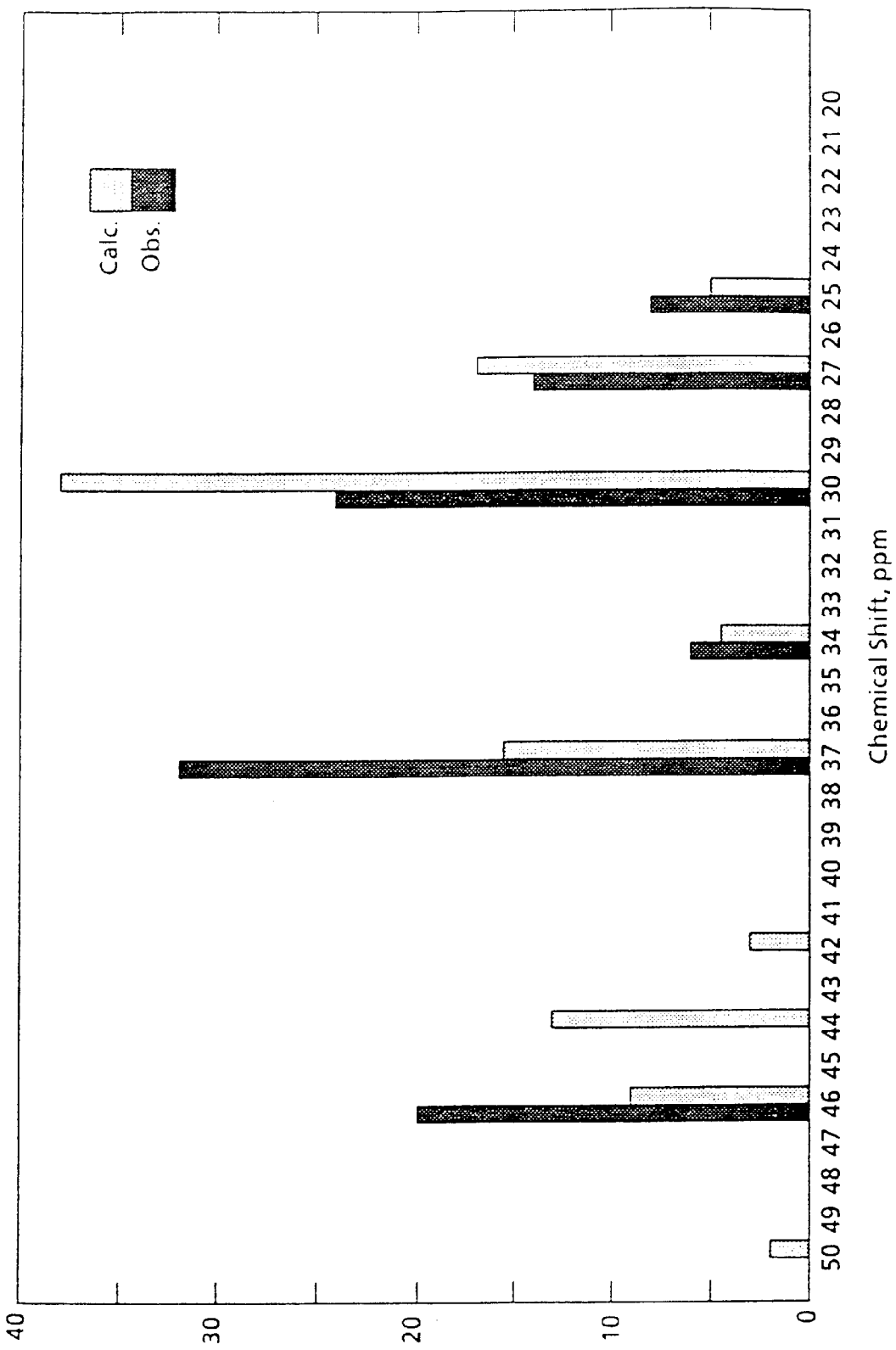
FIG. 14 illustrates lack of agreement between calculated and observed distribution of styrene, ethylene and reversed styrene units in ethylene/styrene copolyers if completely random incorporation rules are followed.

Computer simulation of the polymer and resulting $^{13}$C NMR spectra of completely random α-olefin/hindered monomer copolymers were then performed using no constraints on hindered monomer insertion. In other words, the hindered monomer was allowed to insert into the growing polymer chain after a previous hindered monomer insertion if the random number generator selected hindered monomer as the next monomer to be inserted. The calculated spectra for these completely random copolymers do not agree with the observed $^{13}$C NMR spectra, as shown in FIG. 14 for a 37 mole % styrene containing ethylene/styrene copolymer.

Prior to polymerization according to the present process the monomers and solvents, if any, may be purified by vacuum distillation, and/or contacted with molecular sieves, silica, or alumina to remove impurities. In addition, reactive blanking agents, such as trialkylaluminum compounds, alkali metals and metal alloys, especially Na/K, may be used to remove impurities.

Suitable vinylidenearomatic monomers which may be employed according to the present invention include styrene as well as α-methyl styrene, the lower alkyl- or phenyl-ring substituted derivatives of styrene, such as ortho-, meta-, and para-methylstyrene, or mixtures thereof, the ring halogenated styrenes, vinylbenzocyclobutanes, and divinylbenzene. A preferred vinylidenearomatic monomer is styrene.

In the polymerization of vinylidenearomatic monomers or hindered aliphatic vinylidene compounds and olefins the monomers are preferably combined in a proportion so as to achieve a vinylidenearomatic monomer (or hindered aliphatic vinylidene compound) content of at least 1.0 mole percent in the resulting polymer more preferably from 1.5 to less than 50 mole percent, highly preferably 5.0 to 48 mole percent, and most preferably from more than 8.0 up to 47 mole percent. Preferred operating conditions for such polymerization reactions are pressures from atmospheric to 1000 atmospheres and temperatures from 30° C. to 200° C. Polymerizations at temperatures above the autopolymerization temperature of the respective monomers may contain small amounts of homopolymer polymerization products resulting from free radical polymerization.

Certain of the polymers prepared according to the present invention, especially copolymers of ethylene and an α-olefin other than ethylene, are characterized by unique rheological properties. In particular, it has been found that the polymers (hereinafter called Elastic Polyethylenes or ElPEs) are less Newtonian than onventionally prepared linear polyethylene resins of similar olefin content. The polymers also have higher elastic modulus particularly at high melt indices compared to such conventional polymers. This property makes the resin especially useful in the formation of films, foams and fabricated articles, for example by blow molding techniques. The above phenomenon is more particularly defined by reference to FIG. 16 wherein complex viscosity, $\eta^*$ measured in poise at 190° C., is plotted as a function of shear rate, ω, measured in radians per second for a typical ElPE copolymer of ethylene and 1-octene according to the invention. The slope of this curve indicates the melt is highly non-Newtonian. The actual values of $\eta^*$ and ω utilized in the graph are:

| $\eta^*$ | ω | $\eta^*$ | ω | $\eta^*$ | ω |
|---|---|---|---|---|---|
| $1.962 \times 10^5$ | 0.01000 | $3.230 \times 10^4$ | 0.2512 | $1.088 \times 10^4$ | 6.310 |
| $1.511 \times 10^5$ | 0.01585 | $2.713 \times 10^4$ | 0.3981 | $9.336 \times 10^3$ | 10.000 |
| $1.115 \times 10^5$ | 0.02512 | $2.293 \times 10^4$ | 0.6310 | $7.964 \times 10^3$ | 15.850 |
| $8.292 \times 10^4$ | 0.03981 | $1.966 \times 10^4$ | 1.0000 | $6.752 \times 10^3$ | 25.120 |
| $6.322 \times 10^4$ | 0.06310 | $1.701 \times 10^4$ | 1.5850 | $5.677 \times 10^3$ | 39.810 |
| $4.920 \times 10^4$ | 0.10000 | $1.464 \times 10^4$ | 2.5120 | $4.721 \times 10^3$ | 63.100 |
| $3.956 \times 10^4$ | 0.15850 | $1.265 \times 10^4$ | 3.9810 | $3.854 \times 10^3$ | 100.000 |

Figure 15:
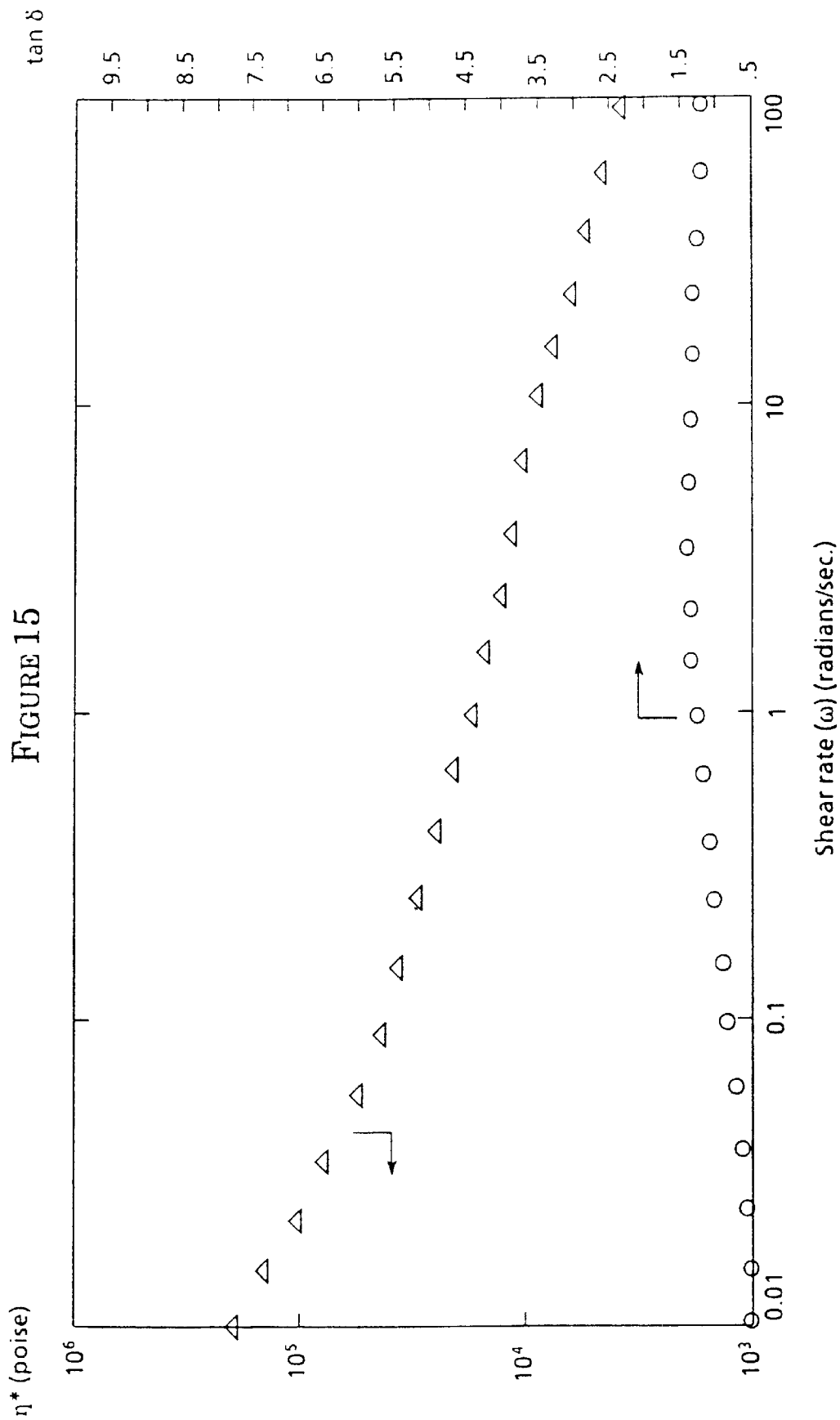
FIG. 15 shows typical rheology curves of a ElPE resin according to the present invention. Shown are complex viscosity, $\eta^*$, and tan $\delta$ curves as a function of shear rate, for the resin.

Also plotted in FIG. 15 is the tan δ value of the same ElPE polymer. This value is unitless and is calculated by dividing the viscous modulus value by the elastic modulus. The actual values of tan δ and ω utilized in the graph are:

| tan δ | ω | tan δ | ω | tan δ | ω |
|---|---|---|---|---|---|
| 0.5526 | 0.01000 | 1.243 | 0.2512 | 1.718 | 6.310 |
| 0.5231 | 0.01585 | 1.381 | 0.3981 | 1.677 | 10.000 |
| 0.5771 | 0.02512 | 1.543 | 0.6310 | 1.620 | 15.850 |
| 0.6597 | 0.03981 | 1.615 | 1.0000 | 1.552 | 25.120 |
| 0.7971 | 0.06310 | 1.690 | 1.5850 | 1.475 | 39.810 |
| 0.9243 | 0.10000 | 1.729 | 2.5120 | 1.398 | 63.100 |
| 1.080 | 0.15850 | 1.737 | 3.9810 | 1.315 | 100.000 |

For improved performance in melt blowing applications preferably the tan δ value is from 0.1 to 3.0 for shear rates between 0.01–100 radian/sec.

Figure 16:
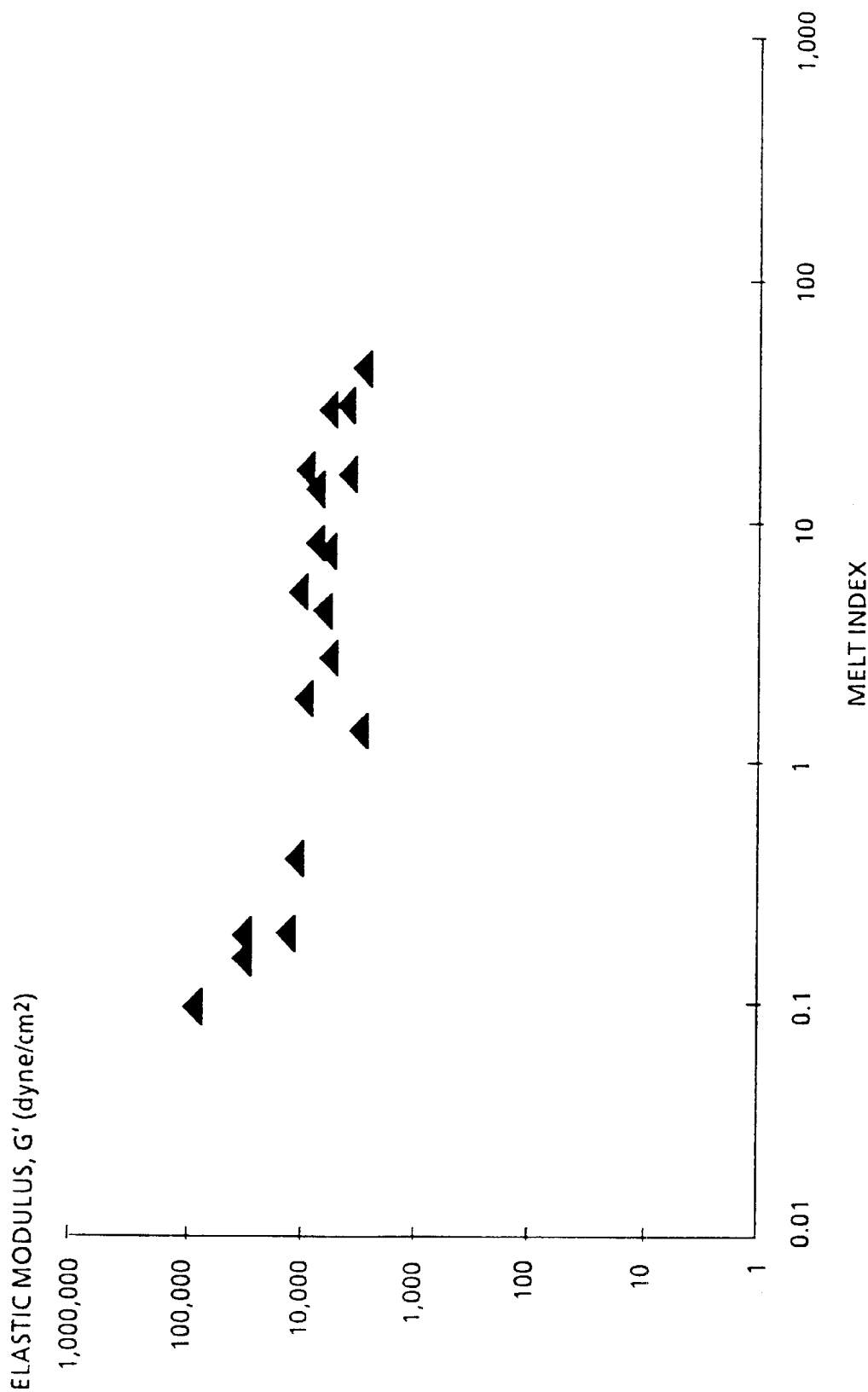
FIG. 16 shows a typical curve of elastic modulus versus melt index for the ElPE resins of the present invention.

A further property of ElPE polymers is illustrated by reference to FIG. 16. The elastic modulus in dynes/cm², G', at 0.1 radian/sec., and 190° C. for several ethylene/1-octene ElPE resins is plotted as a function of melt index. The resins utilized include those of Examples 11, 12, 14–16, 18–22, 24–26, 30 and 31.

The values of melt index and elastic modulus utilized in the graph are as follows:

| Melt Index | Elastic Modulus | Melt Index | Elastic Modulus | Melt Index | Elastic Modulus |
|---|---|---|---|---|---|
| 0.10 | 98760 | 3.34 | 4381 | 18.42 | 9669 |
| 0.15 | 35220 | 5.34 | 5858 | 31.2 | 4516 |
| 0.18 | 35920 | 6.38 | 10480 | 31.53 | 5012 |
| 0.22 | 14270 | 10.12 | 5276 | 31.69 | 3238 |
| 0.45 | 11140 | 10.66 | 6222 | 41.02 | 2972 |
| 1.72 | 3003 | 16.28 | 2697 | | |
| 2.46 | 10620 | 16.32 | 6612 | | |

Figure 17:
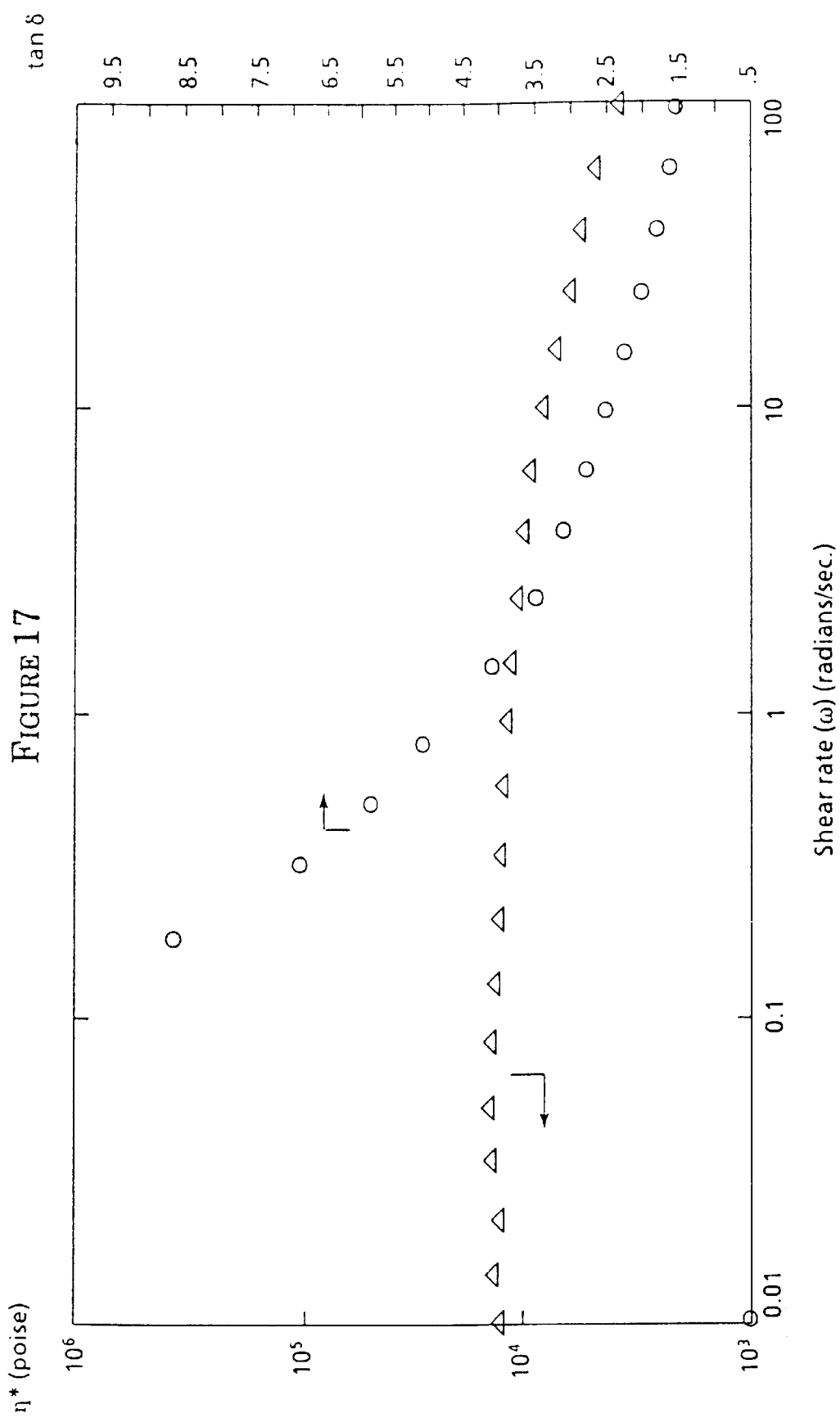
FIG. 17 shows typical rheology curves of a conventionally prepared polyethylene resin. Shown are complex viscosity, $\eta^*$, and tan $\delta$ curves as a function of shear rate, for the resin.

Typical properties of $\eta^*$ and co for a conventionally prepared polyethylene resin are provided in FIG. 17 for comparison purposes.

It is readily seen that ElPE resins are characterized by high elastic modulus in the melt. In particular, ElPE resins have a melt index (($I_2$), ASTM D-1238 Procedure A, condition E), less than 200, preferably less than 125, most preferably less than 50 and an elastic modulus greater than 1000 dyne/cm², more preferably greater than 2000 dyne/cm². All of the foregoing rheological measurements are performed by standard techniques such as are disclosed in H. A. Barnes et al., Introduction to Rheology, Elsevier, publishing, Inc., 1989. Densities normally range from 0.85 to 0.97, preferably from 0.89–0.97. Molecular weight distributions (Mw/Mn) are greater than 2.0, preferably from 3.0–10.0. Typically melting points range from 50° C. to 135° C.

Preferred polymers additionally demonstrate properties of substantially homogeneous polymers as defined in U.S. Pat. No. 3,645,992, the teachings of which are herein incorporated in their entirety by reference thereto. Polymers produced at elevated polymerization temperatures, especially temperatures greater than 130° C., may exhibit a heterogeneous melt curve. The polymers of the invention are further marked by high clarity. In particular the polymers have better optical properties, especially lower haze than typical ethylene polymers, making them especially well suited for film and injection molding aplications.

In addition those polymers comprising an olefin and a vinylidene aromatic monomer, especially ethylene and styrene, have surprisingly been found to possess elastomeric properties. Thus, such polymers are uniquely suited for use in applications for thermoplastic elastomers such as impact modification of thermoplastic and thermosetting polymers including bitumens; adhesives; elastomeric moldings; etc.

The polymers of the invention may be modified by typical grafting, crosslinking, hydrogenation, functionalizing, or other reactions well known to those skilled in the art. With particular regard to the polymers comprising vinylidene aromatic, vinylcyclohexene, or 1,4-hexadiene functionality, the same may be readily sulfonated or chlorinated to provide functionalized derivatives according to established techniques. Additionally, the vinylcyclohexene based polymers are readily crosslinkable by reaction of the unsaturated ring functionality.

The polymers of the present invention, whether or not further modified, may be blended with synthetic polymers to provide blends having desirable properties. In particular polyethylene, ethylene/α-olefin copolymers, polypropylene, polystyrene, styrene/acrylonitrile copolymers (including rubber modified derivatives thereof), syndiotactic polystyrene, polycarbonate, polyamide, aromatic polyester, polyisocyanate, polyurethane, polyacrylonitrile, silicone, and polyphenyleneoxide polymers may be blended with the polymeric compositions of the present invention.

In a highly preferred embodiment of the invention the polymers containing ethylene and styrene are elastomeric as defined in the definition of an elastomeric substance by ASTM Special Technical Bulletin No. 184 as a substance that can be stretched at room temperature to twice its length and will return to its original length upon release.

In addition to modification of synthetic thermoplastics the present polymers are also usefully employed as modifiers for asphalt or bitumen compositions. Desirably the polymers of styrene/ethylene are utilized in this manner.

The term "bitumen" can generally be defined as mixtures of hydrocarbons of natural or pyrogenous origin or combinations of both, frequently accompanied by their non-metallic derivatives, which may be gaseous, liquid, semi-solid or solid, and which are usually soluble in carbon disulfide. For the purposes of the present invention, bitumen of a liquid, semi-solid or solid nature may be utilized. From a commercial standpoint, bitumen is generally restricted to asphalts and tars and pitches. A listing of various bituminous materials which can be utilized in the present invention include the following:

I. Asphalts
  1. Petroleum Asphalts
    A. Straight-reduced asphalts
      1. Atmospheric or reduced-pressure reduction
      2. Solvent precipitated, as with propane
    B. Thermal asphalts, as residues from cracking operations on petroleum stocks
    C. Air-blown asphalts
      1. Straight-blown
      2. "Catalytic"-blown
  2. Native Asphalts
    A. With mineral content below 5 percent
      1. Asphaltites such as gilsonite, graphamite, and glance pitch
      2. Bermudez and other natural deposits
    B. With mineral content over 5 percent
      1. Rock asphalts
      2. Trinidad and other natural deposits
II. Tars and Derivatives
  1. Residua from coke-oven-dried coal tars
    A. Coal tars reduced to float grades, as RT (road tar) grades for paving purposes
    B. Coal-tar pitches, with reduction carried out to softening-point grades
  2. Residua from other pyrogenous distillates as from water-gas, wood, peat, bone, shale, rosin, and fatty acid tars.

As can be readily appreciated by those skilled in the art, the weight average molecular weight of the various bitumens can vary over a very wide range, for example such as from about 500 to about 10,000. Additionally, the softening point of the various types of asphalt will also vary such as from about 50° F. to about 400° F.

Of the many types of asphalts which may be utilized, petroleum, and native are desired, with petroleum being preferred. Of the petroleum asphalts, the thermal asphalts are preferred.

The amount of bitumen utilized in the compositions of the invention may range from about 65 to about 99 parts by weight with preferred amounts ranging from about 80 to about 98 parts by weight.

Having described the invention the following examples are provided as further illustrative and are not to be construed as limiting. Unless stated to the contrary parts and percentages are based on weight.

EXAMPLE 1

Preparation of (tert-Butylamido)dimethyl (tetramethyl-$\eta^5$-cyclopentadienyl)silane Zirconium Dichloride To 0.443 g (1.90 mmol) $ZrCl_4$ in a flask was added 8 mL diethyl ether, then 15 mL tetrahydrofuran (THF). To the resulting slurry was slowly added a solution of 0.500 g (1.90 mmol) dilithium (tert-butylamido)dimethyl (tetramethylcyclopentadienyl)silane in 15 mL THF. The resulting yellow solution was stirred for several days. The solvent was removed to give a gummy residue, which was extracted with 5/1 (volume) diethyl ether/pentane and filtered from a white solid. The solvent was removed from the yellow filtrate to give a light-yellow powder. Recrystallization from ether/pentane (5/1) yielded the product ($C_5Me_4$($Me_2Si$—N-tert-Bu)$ZrCl_2$) as an off-white crystalline solid. The yield was 0.2207 g (28.2%). Identification was made by $^{13}C$ and $^1H$ NMR.

Polymerization

A. Five mL of a 1.009 M solution of methyl aluminoxane (MAO) in toluene was added to a shot tank containing 25 mL of 4-methyl-1-pentene. The catalyst solution was prepared by adding 500 μL of a 0.01172 M solution of $C_5Me_4$($Me_2SiTert$-Bu)$ZrCl_2$ in toluene to 2 mL of toluene in a second shot tank. Both shot tanks were sealed, removed from the glove box, and attached to a 600 mL stainless steel pressure vessel. The pressure vessel was evacuated and purged with argon.

The 4-methyl-1-pentene/toluene/MAO solution was added to the pressure vessel and warmed to 89° C. under 620 kPa (90 psig) ethylene with stirring. Upon addition of the catalyst solution to the 4-methyl-1-pentene/MAO/ethylene mixture, the ethylene pressure was increased to 1240–1275 kPa (180–185 psig). After 2 hours the solution was cooled to 30° C. and vented. The yield of polymer obtained after drying under reduced pressure at 100° C. overnight was 10.0 g. $^{13}C$ NMR analysis of the polymer showed it to be a random copolymer of ethylene with 4-methyl-1-pentene.

B. The polymerization procedure of Polymerization A was essentially repeated except that 50 mL of 1-hexene was used instead of 4-methyl-1-pentene and the catalyst concentration was 0.01012 M in toluene. The catalyst solution was added to the 1-hexene/MAO/ethylene mixture and the ethylene pressure was increased to 1240–1275 kPa (180–185 psig). When the catalyst solution was added the temperature of the reaction climbed to 139° C. After 30 minutes the solution had cooled to 100° C. Heating and ethylene feed were discontinued and the reactor was cooled and vented. The yield of polymer obtained after drying under reduced pressure at 100° C. overnight was 36.8 g. $^{13}$C NMR analysis of the polymer showed it to be a random copolymer of ethylene with 1-hexene (8% on a mole basis).

C. The polymerization procedure of Polymerization A was essentially repeated except that 213 µL of the catalyst solution (0.01172 M in toluene) was used, and 143 mg of solid MAO was used. No additional olefin was added. When the catalyst solution was added to the reactor the temperature increased to 109° C. due to the exothermic polymerization reaction. The reaction was halted after 1 hour by cooling and venting the reactor. The yield of polyethylene obtained after drying under reduced pressure at 100° C. overnight was 11.0 g.

D. 150 mL of toluene was added to the pressure vessel employed in Polymerization A, followed by 100 g of propylene. A solution of 0.828 g of MAO in 8 mL of toluene was added, followed by 2130 µL of the catalyst solution. The mixture was allowed to react for 3.0 hr at 8° C. The reaction mixture was quenched with acidic methanol, and 0.38 g of a white, tacky material was obtained. $^{13}$C NMR analysis of the polymer showed it to be atactic polypropylene.

EXAMPLE 2

Preparation of (tert-Butylamido)dimethyl (tetramethyl-η-cyclopentadienyl)silanetitanium Dichloride Preparation 1

(Chloro)(dimethyl)(tetramethylcyclopentadi-2,4-enyl) silane

To a solution of 21.5 g (167 mmol) dimethyldichlorosilane in 150 mL THF cooled to −40° C. was slowly added a solution of 8.00 g (55.6 mmol) sodium 1,2,3,4-tetramethylcyclopentadienide in 80 mL THF. The reaction mixture was allowed to warm to room temperature and was stirred overnight. The solvent was removed, the residue was extracted with pentane and filtered. The pentane was removed under reduced pressure to give the product as a light-yellow oil. The yield was 10.50 g (88.0%). $^1$H NMR ($C_6D_6$) δ 2.89 (s, 1H), 1.91 (s, 6H), 1.71 (s, 6H), 0.14 (s, 6H); $^{13}$C NMR ($C_6D_6$) δ 137.8, 131.5, 56.6, 14.6, 11.4, 0.81.

(tert-Butylamino)(dimethyl)(tetramethylcyclopentadi-2,4-enyl)silane

A solution of 11.07 g (151 mmol) t-butyl amine in 20 mL THF was added during 5 minutes to a solution of 13.00 g (60.5 mmol) (chloro)(dimetnyl)(tetramethylcyclopentadienyl)silane in 300 mL THF. A precipitate formed immediately. The slurry was stirred for 3 days, then the solvent was removed, the residue was extracted with pentane and filtered. The pentane was removed under reduced pressure to give the product as a light-yellow oil. The yield was 14.8 g (97.2%). MS: 251 $^1$H NMR ($C_6D_6$) δ 2.76 (s, 1H), 2.01 (s, 6H), 1.84 (s, 6H), 1.09 (s, 9H), 0.10 (s, 6H); $^{13}$C NMR ($C_6D_6$) δ 135.4, 133.2, 57.0, 49.3, 33.8, 15.0, 11.2, 1.3.

Dilithium (tert-butylamido)(dimethyl) (tetramethylcyclopentadienyl)silane

To a solution of 3.000 g (11.98 mmol) (tert-butylamino) (dimethyl)(tetramethylcyclopentadienyl)silane in 100 mL ether was slowly added 9.21 mL of 2.6 M (23.95 mmol) butyl lithium in mixed $C_6$ alkane solvent. A white precipitate formed and the reaction mixture was stirred overnight, then filtered. The solid was washed several times with ether then dried under reduced pressure to give the product as a white powder. The yield was 3.134 g (99.8%).

(tert-Butylamido)dimethyl(tetramethyl-η$^5$-cyclopentadienyl)silane Titanium Dichloride 0.721 g (3.80 mmol) Of $TiCl_4$ was added to 30 mL frozen (−196° C.) THF. The mixture was allowed to warm to −78° C. (dry ice bath). To the resulting yellow solution was slowly added a solution of 1.000 g (3.80 mmol) dilithium (tert-butylamido)(dimethyl)tetramethylcyclopentadienyl)silane in 30 mL THF. The solution was allowed to warm to room temperature while stirring overnight. The solvent was removed from the resulting very dark solution. The residue was extracted with pentane and filtered. Cooling in a freezer caused the separation of a very soluble dark reddish-brown material from a light yellow-green crystalline solid. The solid was filtered out and recrystallized from pentane to give the olive-green product. The yield was 0.143 g, 10.2%. $^1$H NMR ($C_6D_6$) δ 2.00 (s, 6H), 1.99 (s, 6H), 1.42 (s, 9H), 0.43 (s, 6H); $^{13}$C NMR ($C_6D_6$) δ 140.6, 137.9, 104.0, 62.1, 32.7, 16.1, 13.0, 5.4.

Preparation 2

In a drybox, 4.0 mL of 2.0 M isopropylmagnesium chloride in diethyl ether was syringed into a 100 mL flask. The ether was removed under reduced pressure to leave a colorless oil. 20 mL of a 4:1 (by volume) toluene:THF mixture was added followed by 0.97 g of (tert-butylamino) dimethyl(tetramethylcyclopentadienyl)silane. The solution was heated to reflux. After 8–10 hours, a white precipitate began to form. After refluxing for a total of 27 hours, the solution was cooled and the volatile materials were removed under reduced pressure. The white solid residue was slurried in pentane and filtered to leave a white powder (1.23 g, 62% yield) of $Me_4C_5SiMe_2N$-t-$BuMg_2Cl_2(THF)_2$.

In the drybox, 0.50 g of $TiCl_3(THF)_3$ was suspended in 10 mL of THF. 0.69 g of solid $Me_4C_5SiMe_2N$-t-$BuMg_2Cl_2$ $(THF)_2$ was added, resulting in a color change from pale blue to deep purple. After 15 minutes, 0.35 g of AgCl was added to the solution. The color immediately began to lighten to a pale green-yellow. After 1½ hours, the THF was removed under reduced pressure to leave a yellow-green solid. Toluene (20 mL) was added, the solution was filtered, and the toluene was removed under pressure to leave a yellow-green microcrystalline solid, 0.51 g (quantitative yield ). The product's identity was confirmed as (tert-butylamido)dimethyl-(tetramethyl-η$^5$-cyclopentadienyl) silanetitanium dichloride by $^1$H NMR, ($C_6D_6$): δ 1.992 (s), 1.986 (s), 1.414 (s), 0.414 (s).

Preparation 3

$TiCl_4$, 0.72 g (3.80 mmol) was added to 35 mL of frozen THF (−196° C.) in a flask. The mixture was warmed to −78° C. A solution of 1.0 g (3.80 mmol) dilithium (tert-butylamido)dimethyl(tetramethylcyclopentadienyl)silane in THF was slowly added. The resulting yellow solution was warmed to room temperature and stirred overnight. The solvent was removed to give a dark residue which was extracted with pentane and filtered. The product ($C_5Me_4$ ($Me_2SiN$-t-Bu)$TiCl_2$) was obtained as a dark greenish-yellow crystalline material after being recrystallized twice from pentane at −35 to −40° C. Identification was confirmed by $^{13}$C and $^1$H NMR.

Preparation 4

In the drybox, $TiCl_3(THF)_3$ (2.0 g, 5.40 mmol) was suspended in 40 mL of THF. Dilithio (tert-butylamido) dimethyl(tetramethylcyclopentadienyl)silane (1.42 g, 5.39 mmol ) was then added, resulting in an immediate darkening of the color, eventually to a deep blue. After 1½ hours of stirring, AgCl (0.84 g, 5.86 mmol) was added. The color immediately began to lighten to a red/orange. After 1½ hours of stirring, the THF was removed under reduced pressure. Diethyl ether (50 mL) was added, the solution was filtered, and the volatile materials were removed under reduced pressure. This yielded 1.91 g of the product (tert-butylamido)dimethyl(tetramethyl-$\eta^5$-cyclopentadienyl)silanetitanium dichloride. $^1$H NMR (C$_6$D$_6$): δ 1.992 (s), 1.987 (s), 1.415 (s), 0.415 (s).

Polymerization

Polymerization of a styrene/ethylene mixture was accomplished by combining 1.65 mL of a 10% solution of MAO in toluene with a solution of 45 mL of toluene and 50 mL styrene in a stainless steel shot tank. 250 μL of a 0.010 M solution of (tert-butylamido)dimethyl-(tetramethyl-$\eta^5$-cyclopentadienyl)silanetitanium dichloride was added to 2.5 mL of toluene in a second shot tank. Both shot tanks were sealed, removed from the glove box, and attached to a 600 mL stainless steel pressure vessel. The pressure vessel was evacuated and purged with argon.

The styrene/toluene/MAO solution was added to the pressure vessel and warmed to 89° C. under 620 kPa (90 psig) ethylene with stirring. At this time the catalyst solution was added and the pressure was increased to 1275 kPa (185 psig) and regulated between 1240–1275 Kpa (180–185 psig). An exotherm raised the temperature to 95° C. The temperature was lowered to 90° C. and was then regulated between 90–92° C. for the remainder of the reaction.

After 1.0 hr. the ethylene feed was discontinued. The reaction was vented to the atmosphere and cooled to 30° C. at which time methanol was added. The product was collected, washed with methanol and residual solvents were removed under reduced pressure at 120° C. which resulted in 9.02 g of material. $^{13}$C NMR analysis of this material showed it to be a random copolymer of styrene (15.2% on a molar basis) and ethylene, free of peaks attributed to polystyrene.

EXAMPLE 3

Olefin Polymerization

Ethylene was polymerized by combining 5 mL of a 1 M solution of triethyl aluminum in mixed C$_6$ alkane solvent and 0.5 mL of a 0.01 M solution of (tert-butylamido)dimethyl(tetramethyl-$\eta^5$-cyclopentadienyl)silanetitanium dichloride in toluene in a stainless steel (SS) shot tank. The titanium catalyst and triethyl aluminum cocatalyst solution was then added under pressure to a 3 L SS pressure vessel containing 2 L of mixed alkane solvent (Isopar™ E, available from Exxon Chemicals, Inc.) under 3100 kPa (450 psig) ethylene at 150° C. The reaction temperature was maintained at 150° C. for 10 minutes. The ethylene pressure was held constant, and a mass-flow meter measured the uptake of ethylene to be 15.7 g. The polymer solution was then removed from the pressure vessel and the polyethylene was recovered after drying under reduced pressure at 90° C. overnight. Yield was 15.7 g.

EXAMPLE 4

Olefin Copolymer Polymerization

In a glove box under argon atmosphere, 5.0 mL of 1.0 M solution of methylaluminoxane (MAO) in toluene was combined with 50 mL of 1-octene in a stainless steel (SS) shot tank fitted with ball valves on both ends. In another SS shot tank 500 μL (5.06 μmol) of a 0.0101 M solution of (tert-butylamido)dimethyl(tetramethyl-$\eta^5$-cyclopentadienyl)silanezirconium dichloride in toluene was added to 2 mL toluene.

The shot tanks were sealed, removed from the glove box and attached to a 600 mL SS pressure vessel. The pressure vessel was evacuated and purged with argon. The solution of 1-octene and MAO was added to the pressure vessel. The solution was warmed to 89° C. under 620 kPa (90 psig) ethylene with stirring. At this time the catalyst solution was added. An exothermic reaction occurred which raised the temperature to 142° C. The ethylene pressure was maintained between 1327–1362 kPa (190–195 psig).

After 0.5 hour the ethylene feed was discontinued. The reactor was cooled to 30° C., vented to the atmosphere, and the reaction was quenched with methanol. The product was collected on a fritted filter and washed with methanol. Residual solvents were removed under reduced pressure at 110° C. which resulted in 35 g of material. $^{13}$C NMR analysis indicated that 1-octene was incorporated into the polymer in an amount of 7.8 mole percent. Differential Scanning Calorimetry (DSC) indicated a Tm of 100° C. Density 0.895 g/mL, Mw=44,000, Mw/Mn=6.8.

EXAMPLE 5

Olefin Copolymer Polymerization

The procedure of Example 4 was substantially repeated excepting that 50 mL of 1-hexene was used instead of 1-octene. The temperature of the reaction was maintained at 133–140° C. Polymer yield was 37 g. Incorporation of 1-hexene was 8 percent on a molar basis, 21% by weight.

EXAMPLE 6

α-Olefin Homopolymerization

A. 4-Methyl-1-pentene (6.0 mL, 4.0 g) was added to 1.0 mL of a 1.0 M MAO solution in toluene in a 20 mL crimp-top vial. To this was added 100 μL of a 0.01172 M toluene solution of the zirconium complex catalyst of Example 4. The vial was sealed, shaken, and allowed to stand at room temperature (ca. 20° C.) for 16 hours, then heated to 48° C. for an additional 24 hours. The viscous polymer solution was precipitated by the addition of methanol. The resulting polymer was collected and the volatile components removed under reduced pressure for four hours at 100° C. to give 3.8 g of a clear polymer (95 percent yield). $^{13}$C NMR analysis indicated that the polymer was atactic poly-4-methyl-1-pentene.

B. The procedure of Polymerization A was essentially repeated. 3.4 g of 1-hexene, 1.0 mL of MAO solution, and 100 μL of the catalyst solution were added to a 20 mL crimp-top vial in an argon-filled drybox. The vial was sealed and heated at 50° C. overnight. After quenching with acidified ethanol and drying there was obtained 3.0 g of poly(1-hexene).

EXAMPLE 7

Ethylene Homopolymerization

A SS shot tank was charged with 500 μL (5.0 μmol) of a 0.010 M toluene solution of (tert-butylamido)dimethyl (tetramethyl-$\eta^5$-cyclopentadienyl)silanetitanium dichloride and 2.5 mL of toluene in an argon filled glove box. In a second SS shot tank, 5.0 mL of a 1.0 M solution of MAO in toluene was added to 92 mL of toluene. Both shot tanks were sealed, removed from the glove box and attached to a 600 mL pressure vessel. The pressure vessel was evacuated and flushed with argon and then flushed with ethylene. The cocatalyst solution was added to the pressure vessel and heated to 89° C. under an ethylene pressure of 620 kPa (90 psig). The catalyst solution was added to the reactor at this time. The temperature rose to 109° C. within seconds as a result of an exothermic reaction. The ethylene pressure was regulated between 1241–1275 kPa (180–185 psig). After about 0.5 hours the reactor temperature had increased to about 110° C. and the uptake of ethylene increased. After 1.0 hours ethylene feed was discontinued, the reactor was vented to the atmosphere, and allowed to cool. The pressure vessel was opened, quenched with methanol, and the polymer was isolated. After removing the volatile components, the yield of polyethylene was 24 g.

EXAMPLE 8

Hindered Vinyl Aliphatic Monomer Polymerization 4-vinylcyclohexene was purified by vacuum distillation from Na/K alloy. In a glove box, 50 mL of 4-vinylcyclohexene was combined with 5.0 mL of a solution of 1.0 M methylaluminoxane (MAO) cocatalyst in toluene in a stainless steel (SS) shot tank fitted with ball valves on both ends. 500 μL of a 0.010 M solution of (tert-butylamido) dimethyl(tetramethyl-$\eta^5$-cyclopentadienyl)silanezirconium dichloride in toluene was added to 2 mL toluene in a similarly fitted SS shot tank.

The shot tanks were sealed, removed from the glove box and attached to a 600 mL SS pressure vessel. The pressure vessel was evacuated and purged with argon. The solution of 4-vinylcyclohexene and MAO was added to the pressure vessel. The solution was warmed to 89° C. under 620 kPa (90 psig) ethylene with stirring. At this time the catalyst solution was added. An exothermic reaction occurred which raised the temperature to 114° C. The ethylene pressure was maintained between 1327–1362 kPa (190–195 psig).

After 1 hour the ethylene feed was discontinued. The reactor was cooled to 30° C., vented to the atmosphere, and the reaction was quenched with acidified methanol. The product was collected on a fritted filter and washed with methanol. Residual solvents were removed under reduced pressure at 110° C. which resulted in 12.6 g of material. $^{13}$C NMR analysis indicated that vinylcyclohexene was incorporated into the polymer in an amount of about 1.5 mole percent.

EXAMPLE 9

Ethylene/Styrene Copolymerization

The above polymerization procedure was substantially followed except that the reaction temperature was 90° C. The reactor was filled with 150 mL of mixed alkane solvent, 500 mL of styrene and 8 mL of 15 percent MAO in toluene (1000 Al:Ti). The reactor was saturated with 180 psig of ethylene, and 20 micromoles of [($C_5Me_4$)$SiMe_2$(N-phenyl)] $TiCl_2$ was added to begin the polymerization. Ethylene was provided on demand at 3102 kPa (450 psig). After 60 minutes, the solution was drained from the reactor into a container which had a small amount of antioxidant. The polymer was dried under vacuum. The polymer yield was 26.6 g, melt index ($I_2$)=26.6. $^{13}$C NMR NMR analysis indicated the polymer was 47 mole percent styrene (76 weight percent). No isotactic, atactic, or syndiotactic sequences were observed.

EXAMPLE 10

Ethylene/Styrene Copolymerization

The reaction conditions of Example 9 are substantially repeated to prepare styrene/ethylene copolymers having differing styrene content. The catalyst was (tert-butylamido) dimethyl(tetramethyl-$\eta^5$-cyclopentadienyl)silanetitanium dichloride except where noted. MAO cocatalyst was employed in an amount to provide an Al:M atomic ratio of 1000:1. Reaction conditions are contained in Table I.

TABLE I

| Run | mg (complex) | T (° C.) | Solvent, amt. (mL)[b] | Ethylene Pressure (kPa) | Styrene (mL) | Time (hr) | Yield (g) | mol % Styrene | Mw | Mw/Mn |
|---|---|---|---|---|---|---|---|---|---|---|
| 1 | 0.92 | 90 | T,50 | 1241 | 50 | 1.0 | 9 | 15.2 | 147,000 | 2.5 |
| 2 | 2.50 | 90 | T,138 | " | 138 | 2.0 | 29 | 18.4 | 65,100 | 2.7 |
| 3 | 2.20 | 90 | T,160 | " | 80 | 2.0 | 27 | 11.7 | 70,100 | 2.6 |
| 4 | 2.20 | 90 | T,204 | " | 36 | 2.0 | 30 | 8.1 | 72,300 | 2.5 |
| 5 | 3.70 | 90 | I,350 | 1517 | 350 | 1.0 | 57 | 10.3 | 121,000 | 2.8 |
| 6 | 3.70 | 90 | I,525 | " | 175 | 0.75 | 70 | 6.8 | 304,000 | 2.6 |
| 7 | 3.70 | 90 | I,600 | " | 100 | 0.33 | 46 | 4.8 | 180,000 | 2.6 |
| 8 | 3.70 | 90 | I,440 | " | 260 | 0.33 | 43 | 9.0 | 172,000 | 2.5 |
| 9 | 1.90 | 90 | I,650 | " | 50 | 0.5 | 12 | 2.5 | 113,000 | 3.2 |
| 10 | 1.90 | 90 | I,650 | " | 50 | 0.5 | 40 | 2.8 | 154,000 | 2.6 |
| 11 | 2.20 | 90 | T,180 | 1241 | 60 | 2.0 | 30 | 13.3 | 78,600 | 3.1 |
| 12[a] | 2.30 | 90 | T,180 | " | 60 | 2.0 | 11 | 37.0 | — | — |

[a]catalyst was (phenylamido)dimethyl(tetramethyl-$\eta^5$-cyclopentadienyl)silanetitanium dichloride
[b]T = tolene, I = mixed alkanes

EXAMPLES 11–32

In these examples, a 4 liter autoclave was charged with 2000 mL of mixed alkane solvent followed by various amounts of 1-octene. The catalyst was (tert-butylamido) dimethyl(tetramethyi-$\eta^5$-cyclopentadienyl)silanetitanium dichloride, dissolved in toluene. The cocatalyst was a 10% solution of MAO in toluene. Hydrogen, if desired, was added by expansion from a 100 mL vessel at a pressure indicated above the operating pressure of the reactor. The reactor was filled with solvent, 1-octene and MAO, heated to the reaction temperature, then pressurized to 3102 kPa (450 psig) with ethylene until the solution was satuated. The hydrogen (if any) was expanded into the reactor, followed by the addition of the catalyst solution. After 10 minutes, the solution was drained from the reactor into a container which had a small amount of antioxidant (Irganox 1010®, available from Ciba-Geigy). The polymer was dried under vacuum. Results are contained in Table II.

TABLE II

| Example | Reactor Temp (° C.) | Octene (mL) | ΔH$_2$ (kPa)[a] | Catalyst mmoles | Al:Ti[b] | Polymer Yield (g) | Mw | Mn | Mw/Mn | Melt Point ° C. | Density g/mL | Melt Index[c] |
|---|---|---|---|---|---|---|---|---|---|---|---|---|
| 11 | 140 | 300 | 0 | 0.02 | 500:1 | 182 | — | — | — | 91 | 0.9063 | 1.72 |
| 12 | 160 | 300 | 0 | 0.02 | " | 61 | 50,900 | 12,800 | 3.98 | 95[d] | 0.9177 | 16.28 |
| 13 | 140 | 300 | 689 | 0.02 | " | 157 | 57,500 | 14,900 | 3.86 | 96 | 0.9175 | 7.91 |
| 14 | 160 | 300 | " | 0.02 | " | 58 | 38,500 | 10,700 | 3.60 | 100[d] | 0.9230 | 31.69 |
| 15 | 140 | 150 | 345 | 0.02 | " | 128 | 66,500 | 17,400 | 3.82 | 105 | 0.9174 | 3.34 |
| 16 | 160 | 150 | " | 0.02 | " | 90 | 53,000 | 13,400 | 3.96 | 106[d] | 0.9317 | 10.66 |
| 17 | 140 | 450 | " | 0.02 | " | 148 | 71,700 | 17,100 | 4.19 | 86 | 0.9010 | 3.84 |
| 18 | 160 | 450 | " | 0.02 | " | 55 | 42,500 | 11,400 | 3.73 | 90[d] | 0.9045 | 31.20 |
| 19 | 150 | 150 | 0 | 0.02 | " | 75 | 71,700 | 16,500 | 4.35 | 108 | 0.9276 | 2.46 |
| 20 | 150 | 150 | 689 | 0.02 | " | 85 | 44,900 | 13,400 | 3.35 | 108 | 0.9261 | 18.42 |
| 21 | 150 | 450 | 0 | 0.02 | " | 107 | 62,500 | 14,800 | 4.22 | 92[d] | 0.9090 | 5.34 |
| 22 | 150 | 450 | 689 | 0.02 | " | 85 | 58,200 | 12,900 | 4.51 | 124 | 0.9516 | 6.38 |
| 23 | 150 | 300 | 345 | 0.02 | " | 100 | 51,000 | 14,000 | 3.64 | 95[d] | 0.9130 | 13.62 |
| 24 | 150 | 300 | " | 0.02 | " | 93 | 53,700 | 14,700 | 3.65 | 96[d] | 0.9121 | 10.12 |
| 25 | 150 | 300 | 689 | 0.02 | " | 115 | 43,000 | 14,200 | 3.03 | 95[d] | 0.9118 | 31.53 |
| 26 | 130 | 150 | 345 | 0.02 | " | 166 | 105,000 | 23,200 | 4.53 | 109 | 0.9198 | 0.18 |
| 27 | 130 | 150 | " | 0.02 | 250:1 | 147 | 136,000 | 29,400 | 4.63 | 110 | 0.9197 | 0.15 |
| 28 | 130 | 150 | " | 0.02 | 100:1 | 83 | 146,000 | 26,300 | 5.55 | 105 | 0.9153 | 0.15 |
| 29 | 110 | 150 | " | 0.01 | 250:1 | 98 | 161,000 | 42,000 | 3.83 | 106 | 0.9140 | 0.15 |
| 30 | 120 | 300 | " | 0.02 | " | 123 | 112,000 | 28,500 | 3.93 | 89 | 0.9016 | 0.45 |
| 31 | 110 | 450 | " | 0.02 | " | 145 | 130,000 | 37,400 | 3.48 | 76 | 0.9000 | 0.22 |
| 32 | 110 | 300 | " | 0.02 | " | 160 | 141,000 | 35,600 | 3.96 | 82 | 0.9000 | 0.15 |

[a]hydrogen partial pressure
[b]equivalent ratio assuming 58 MW for MAO
[c]I$_2$, ASTM D-1238 Procedure A, condition E.

EXAMPLES 33–42

The procedure of examples 11–32 was substantially repeated, except that the catalyst was (tert-butylamido)dimethyl(tetramethyl-η$^5$-cyclopentadienyl)silanezirconium dichloride. Results are contained in Table III.

TABLE III

| Example | Temp ° C. | mL Octene | ΔH$_2$ (kPa) | Zr (mmole) | Al:Zr[a] | Zr eff × 10$^{-3b}$ |
|---|---|---|---|---|---|---|
| 33 | 150 | 300 | 345 | 0.02 | 500 | 50 |
| 34 | 140 | 300 | " | 0.01 | 500 | 122 |
| 35 | 130 | 300 | " | 0.005 | 500 | 285 |
| 36 | 130 | 450 | " | 0.005 | 500 | 302 |
| 37 | 130 | 150 | " | 0.005 | 500 | 230 |
| 38 | 130 | 150 | " | 0.01 | 250 | 158 |
| 39 | 130 | 150 | " | 0.02 | 100 | 104 |
| 40 | 130 | 300 | " | 0.01 | 100 | 154 |
| 41 | 140 | 450 | 0 | 0.015 | 200 | 84 |
| 42 | 140 | 450 | 689 | 0.02 | 200 | 101 |

[a]equivalent ratio, assuming 58 Mw for MAO
[b]catalyst efficiency, g polymer/1 g metal

EXAMPLES 43–57

The procedure of Examples 11–32 was substantially followed except that a 2000 mL reactor was used. The catalyst was (tert-butylamido)dimethyl(tetramethyl-η$^5$-cyclopentadienyl)silanetitanium dichloride (2 mL of a 0.005 M solution in toluene, 10 μmoles). The cocatalyst was 15% MAO in toluene (2 mL, 500 Al:Ti). Results are contained in Table IV.

TABLE IV

| Example | Temp, ° C. | ΔH$_2$ (kPa)[a] | 1-Octene mole | g Polymer | Melt Index[b] | Density |
|---|---|---|---|---|---|---|
| 43 | 100 | 172 | 1.59 | 70.0 | <.1 | 0.8700 |
| 44 | 80 | " | 1.59 | 67.0 | <.1 | 0.8672 |
| 45 | 90 | " | 1.85 | 98.2 | | 0.8582 |
| 46 | 100 | " | 2.12 | 118.3 | 0.96 | 0.8575 |
| 47 | 100 | 345 | 1.85 | 131.9 | 7.48 | 0.8552 |
| 48 | 80 | 172 | 2.12 | 139.3 | 0.93 | 0.8528 |
| 49 | 90 | 0 | 1.59 | 104.4 | 0.25 | 0.8594 |
| 50 | 90 | 345 | 2.12 | 133.1 | | 0.8556 |
| 51 | 90 | 172 | 1.85 | 130.2 | | 0.8550 |
| 52 | 100 | 0 | 1.85 | 110.0 | 0.66 | 0.8570 |
| 53 | 90 | 172 | 1.85 | 141.0 | | 0.8545 |
| 54 | 80 | 345 | 1.85 | 161.2 | 5.44 | 0.8525 |
| 55 | 80 | 0 | 1.85 | 118.1 | 0.48 | 0.8536 |
| 56 | 90 | 0 | 2.12 | 150.8 | 3.12 | 0.8516 |
| 57 | 90 | 345 | 1.59 | 136.7 | 3.43 | 0.8578 |

[a]hydrogen partial pressure
[b]I$_2$, ASTM D-1238 Procedure A, condition E.

EXAMPLES 58–77

Olefin Polymerization

Ethylene and/or ethylene/1-octene were respectively polymerized as a homopolymer or copolymer by adding a solution of the appropriate catalyst in combination with MAO or triethyl aluminum cocatalyst to a 3 L SS pressure vessel containing mixed C$_6$ alkane solvent/1-octene (with varying ratios) under 3100 kPa (450 psig) of ethylene at 150° C. (or 175° C. where indicated) for 10 minutes. The ethylene pressure was held constant and a mass flow meter measured the uptake of ethylene. The consequent polymer was then removed from the pressure vessel and dried under reduced pressure at 90° C. overnight. Results are contained in Table V.

TABLE V

| Example | Catalyst[a,b] | Solvent/Octene[c] | Wt. of polymer (g) | Melt Index ($I_2$) | Mw | Mn | Mw/Mn |
|---|---|---|---|---|---|---|---|
| 58 | Ti | 1/1 | 61.1 | 79.0 | 45,600 | 9100 | 5.01 |
| 59 | Ti | 2/0.3 | 48.7 | 1.7 | 88,300 | 10100 | 8.74 |
| 60 | Ti | 1/1 | 41.5 | 137.6 | 36,300 | 9950 | 3.68 |
| 61 | Zr | 1/1 | 55.2 | 1324.9 | — | — | — |
| 62 | Zr | 2/0.15 | 33.3 | 10.3 | — | — | — |
| 63 | Zr | 2/0 | 25.8 | 8.8 | 58,400 | 5310 | 10.90 |
| 64 | Zr | 0/2 | 102.9 | 168.1 | 30,900 | 8150 | 3.79 |
| 65[d] | Zr | 2/0 | 17.8 | 147.1 | — | — | — |
| 66 | Zr | 2/0 | 25.3 | 240.8 | — | — | — |
| 67 | Ti | 2/0 | 15.6 | 4.4 | — | — | — |
| 68 | Zr | 2/0 | 20.6 | 2.8 | 101,000 | 7700 | 13.10 |
| 69 | Zr | 2/0.3 | 44.0 | 17.1 | 47,300 | 6550 | 7.22 |
| 70 | Zr | 0/2 | 96.6 | 149.2 | 43,500 | 4710 | 5.87 |
| 71 | Ti | 1/1 | 47.5 | 25.8 | 54,000 | 10800 | 5.00 |
| 72 | Ti | 2/0.3 | 74.5 | 56.3 | 44,400 | 12100 | 3.67 |
| 73 | Ti | 2/0.3 | 75.0 | 56.9 | 44,700 | 9800 | 4.56 |
| 74 | Ti | 2/0 | 15.6 | — | — | — | — |
| 75[e] | Ti | 2/0.15 | 19.9 | — | — | — | — |
| 76 | Ti | 2/0.15 | 34.5 | 1.0 | — | — | — |
| 77 | Zr | 0/2 | 88.3 | 111.7 | 35,100 | 6440 | 545 |

[a]Ti = (tert-butylamido)dimethyl(tetramethyl-$\eta^5$-cyclopentadienyl)silanetitantium dichloride
Zr = (tert-butylamido)dimethyl(tetramethyl-$\eta^5$-cyclopentadienyl)silanezirconium dichloride
[b]Metal/Al ratio = 1/1000 assuming 58 MW for MAO
[c]liters of each
[d]Run at 175° C.
[e]Used triethylaluminum as cocatalyst; metal/Al was 1:1000

EXAMPLE 78

Preparation of Supported (tert-Butylamido)dimethyl (tetramethyl-$\eta^5$-cyclopentadienyl)silanetitanium Dichloride 0.100 g of dehydroxylated silica (—OH concentration≈1 mmol/g $SiO_2$) was slurried in 20 mL of mixed $C_6$ alkane solvent under a nitrogen atmosphere in a dri-box, with stirring in a 50 mL Erlenmeyer flask. From this slurry 1.0 mL was removed by syringe and combined with 1.10 mL of a 0.011 M toluene solution of (tert-butylamido)dimethyl (tetramethyl-$\eta^5$-cyclopentadienyl)silanetitanium dichloride in a 5 mL rounded-bottomed flask and stirred for 12 h. After this period 6.7 mL of a 10 percent (w/w) solution of methyl aluminoxane (MAO) in toluene was added to the silica containing solution.

Polymerization

The polymerization was conducted by adding under pressure the above titanium/silica/MAO slurry in a 3 L SS pressure vessel containing 2 L of mixed alkane solvent under 3100 kPa (450 psig) of ethylene at 150° C. for 10 minutes. The ethylene pressure was held constant and a mass flow meter measured the uptake of ethylene to be 26.7 g. The polymer solution was then removed from the pressure vessel and the polyethylene was recovered after drying under reduced pressure at 90° C. overnight. Yield was 30.0 g.

EXAMPLE 79

Preparation of (2-Methoxyphenylamido)dimethyl (tetramethyl-$\eta^5$-cyclopentadienyl)silanetitanium Dichloride ((Tetramethylcyclopentadienyl)dimethylsilyl)(2-methoxyphenyl)amine To 1.3 g (5.9 mmol) ((tetramethylcyclopentadienyl) dimethylsilyl)chloride in 50 mL tetrahydrofuran (THF) was added 0.86 g (5.9 mmol) sodium 2-methoxyanilide. The mixture was stirred overnight. The solvent was removed under reduced pressure and the residue extracted with pentane. The pentane extracts were filtered, combined, and concentrated to give a pale yellow liquid. Yield 1.4 g (79%). $^1$H NMR (benzene-$d_6$) δ 6.91 (m, 2.2), 6.74 (m, 1.1), 6.57 (d, 1.1, J=9), 4.25 (s, 1), 3.32 (s, 3.7), 1.93 (s, 6.7), 1.80 (s, 6.8), 0.13 (s, 6.3).

Dilithium ((tetramethylcyclopentadienyl)dimethylsilyl) (2-methoxyphenyl)amide.

To 1.4 g (4.6 mmol) ((tetramethylcyclopenta-dienyl) dimethylsilyl)(2-methoxyphenyl)amine in diethyl ether was added dropwise 3.9 mL of 2.5 M butyl lithium (9.8 mmol) in hexane solvent. A white precipitate formed. Pentane was added to the mixture. The slurry was filtered and the solids washed with pentane.

(2-Methoxyphenylamido)dimethyl(tetramethyl-$\eta^5$-cyclopentadienyl)silanetitanium Dichloride To 1.6 g of dilithium ((tetramethylcyclopentadienyl) dimethylsilyl)(2-methoxyphenyl)amide slurried in toluene was added 0.85 g $TiCl_4$. The mixture was stirred for three days, filtered, and the solvent was removed under reduced pressure. The residue was slurried in pentane and filtered to give a dark powder. Yield 0.77 g (41%). $^1$H NMR (benzene-$d_6$) δ 4.10 (s, 3), 2.20 (s, 6.4), 1.99 (s, 6.6), 0.40 (s, 6.3).

EXAMPLE 80

Preparation of (4-Fluorophenylamido)dimethyl (tetramethyl-$\eta^5$-cyclopentadienyl)silanetitanium Dichloride ((Tetramethylcyclopentadienyl)dimethylsilyl)(4-fluorophenyl)amine Equimolar quantities of ((tetramethylcyclopentadienyl) dimethylsilyl)chloride and lithium 4-fluoro anilide were combined in THF and the mixture stirred overnight. The solvent was removed under reduced pressure. $^1$H NMR (benzene-$d_6$) δ 6.79 (m, 2.5), 6.33 (m, 2.4), 2.95 (s,1), 2.90 (s, 1), 1.87 (s, 6.9), 1.79 (s, 6.9), 0.02 (s, 5.8).

Dilithium ((Tetramethylcyclopentadienyl)dimethylsilyl) (4-fluorophenyl)amide ((Tetramethylcyclopentadienyl)dimethylsilyl)(4-fluorophenyl)amine in diethyl ether solvent and butyl lithium 2.5 M in hexane solvent were combined in equivalent amounts. A white precipitate formed. Pentane was added to the slurry. The precipitate was filtered, washed with pentane and dried. $^1$H NMR (THF-d$_8$) δ 7.28 (m, 2.0), 6.77 (m, 2), 3.27 (s, 2.7), 2.05 (s, 5.2), 2.01(s, 5.2), 0.44 (s, 4.6)

(4-Fluorophenylamido)dimethyl(tetramethyl-η$^5$-cyclopentadienyl)silane Titanium Dichloride To 0.59 g (1.6 mmol) TiCl$_3$.3THF in 50 mL THF was added 0.50 g (1.7 mmol) dilithium ((tetramethylcyclopentadienyl)dimethylsilyl)(4-fluorophenyl)amide. After 0.5 hr, 0.25 g (1.8 mmol) AgCl was added. After 2 hr the solvent was removed under reduced pressure. The residue was extracted with diethyl ether. The ether extracts were filtered, combined, and concentrated under reduced pressure to give a red glassy solid. Dissolution into toluene and reconcentration produced a waxy solid. This solid was extracted into pentane. The pentane extracts were filtered, combined, and concentrated to produce a waxy solid. This was slurried with a small amount of pentane (2 mL) and filtered to give a red powder. The yield was 0.18 g (28%). $^1$H NMR (benzene-d$_6$) δ 7.10 (t), 6.80 (t), 2.00 (s), 1.97 (s), 0.35 (s).

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 450 psig of ethylene, and a 75 mL tank of hydrogen was pressurized to 500 psig to give a delta pressure of 50 psi. The hydrogen was expanded into the reactor, and 10 micromoles of the above complex was added to begin the polymerization. Ethylene was provided on demand at 450 psig. After 10 minutes, the solution was drained from the reactor into a container which had a small amount of antioxidant. The polymer was dried under vacuum. The polymer yield was 12.8 g, Mw=103,000, Mw/Mn=4.77, density=0.9387, melt index=6.37.

EXAMPLE 81

Preparation of ((2,6-di(1-Methylethyl)phenyl)amido)dimethyl(tetraethyl-η$^5$-cyclopentadienyl) silane Titanium Dichloride Dilithium ((tetramethylcyclopentadienyl)dimethylsilyl)(2,6-di(1-methylethyl)phenyl)amide was prepared in a manner analogous to Example 80.

To 1.5 g (4 mmol) TiCl$_3$.3THF in 25 mL THF was added 1.5 g (4 mmol) dilithium ((tetramethylcyclopentadienyl)dimethylsilyl)(2,6-di(1-methylethyl)phenyl)amide. After 0.5 hr 0.63 g (4 mmol) AgCl was added. After 1.5 hr the solvent was removed under reduced pressure. The residue was extracted with pentane (3×8 mL). The pentane insoluble residue was extracted with diethyl ether. The ether extract was filtered and evaporated to dryness to give a yellow crystalline solid. $^1$H NMR (benzene-d6) d 3.04 (heptet, 2, J=6.7), 2.18 (s, 5.8), 1.98 (s, 5.8), 1.49 (d, 5.8, J=6.5), 1.12 (d, 6.2, J=6.8), 0.48 (s, 5.2).

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 450 psig of ethylene, and a 75 mL tank of hydrogen was pressurized to 500 psig to give a delta pressure of 50 psi. The hydrogen was expanded into the reactor, and 10 micromoles of the above complex was added to begin the polymerization. Ethylene was provided on demand at 450 psig. After 10 minutes, the solution was drained from the reactor into a container which had a small amount of antioxidant. The polymer was dried under vacuum. The polymer yield was 14.7 g.

EXAMPLE 82

Preparation of (4-Methoxyphenylamido)dimethyl (tetramethyl-η$^5$-cyclopentadienyl)silanetitanium Dichloride To 0.73 g TiCl$_4$.2THF in 30 mL toluene was added 0.7 g of dilithium ((tetramethylcyclopentadienyl)dimethylsilyl)(4-methoxyphenyl)amide (prepared in a method analogous to Example 81. The mixture was stirred for two days, filtered, and concentrated under reduced pressure. The residue was slurried in pentane and filtered to give a brick red powder. Yield 0.61 g (67%). $^1$H NMR (benzene-d$_6$) δ 7.28 (d, 2, J=8.8), 6.78 (d, 2, J=8.9), 3.27 (s, 2.8), 2.05 (s, 5.6), 2.01 (s, 5.6), 0.44 (s, 4.8).

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 450 psig of ethylene, and a 75 mL tank of hydrogen was pressurized to 500 psig to give a delta pressure of 50 psi. The hydrogen was expanded into the reactor, and 10 micromoles of the above complex was added to begin the polymerization. Ethylene was provided on demand at 450 psig. After 10 minutes, the solution was drained from the reactor into a container which had a small amount of antioxidant. The polymer was dried under vacuum. The polymer yield was 7.2 g, Mw=79,800, Mw/Mn=21.5, melt index=2.90.

EXAMPLE 83

Preparation of (Tetramethyl-η$^5$-cyclopentadienyl) dimethyl(1-methylethoxy)silanetitanium Trichloride (Tetramethylcyclopentadienyl)dimethyl(1-methylethoxy) silane To 1.0 g (4.8 mmol) (tetramethylcyclopentadiene) dimethylsilyl chloride in 10 mL toluene was added 0.38 mL (5.0 mmol) 2-propanol followed by 0.66 mL (4.7 mmol) triethylamine. The mixture was filtered and the solids washed with mixed C$_6$ alkane solvent. The wash and the filtrate were combined and concentrated under reduced pressure to give a pale yellow liquid. $^1$H NMR (benzene-d$_6$) δ 3.85 (heptet, 1, J=6.0), 2.9 (s, 1.1), 2.03 (s, 5.7), 1.8 (s, 6.3), 1.10 (d, 6.3, J=6.0), −0.02 (s, 5.0).

Potassium (Dimethyl (1-methylethoxy)silyl) tetramethylcyclopentadienide)

To 0.51 g (2.1 mmol) (tetramethylcyclopentadienyl) dimethyl(1-methylethoxy)silane in toluene was added 0.33 g (2.5 mmol) potassium benzide. The solution was filtered after 3 days and the solvent was removed under reduced pressure to give an oil. The oil was washed with pentane. Residual pentane was removed under reduced pressure to give an orange glassy solid. $^1$H NMR THF-d$_8$) δ 3.89 (heptet. 1, J=6.1), 2.00 (s, 6.1), 1.87 (s, 5.7), 1.05 (d, 5.1, J=6.1), 0.22 (s, 4.4).

(Tetramethyl-η$^5$-cyclopentadienyl)dimethyl(1-methylethoxy)silanetitanium Trichloride To 0.42 g (1.1 mmol) TiCl$_3$·3THF in 50 mL THF was added dropwise 0.83 mmol potassium (dimethyl(1-methylethoxy)silyl)tetramethylcyclopentadienide) in 15 mL THF. One hour after addition was complete 0.2 g (1.3 mmol) AgCl was added. The resulting mixture was stirred for 18 hr. The solvent was removed under reduced pressure and the residue extracted with pentane. The pentane extracts were filtered, combined, and evaporated to a red oil. The red oil was slurried in pentane and the mixture was filtered. The filtrate was stored art −30° C. for 3 weeks which resulted in the precipitation of an orange solid. The solution was decanted from the solid. $^1$H NMR (benzene-d$_6$) δ 3.8(heptet, 1, J=6.0), 2.35 (s, 6.9), 1.86 (s, 7.4), 1.04 (d, 7.1, J=6.0), 0.45 (s, 6.7) 0.00 (s), 1.97 (s), 0.35 (s).

EXAMPLE 84

Preparation of 1-(tert-Butylamido)-2-(tetramethyl-η$^5$-cyclopentadienyl)-1,1,2,2-tetramethyldisilanetitanium Dichloride 1-Chloro-2-(tetramethylcyclopentadienyl)-1,1,2,2-tetramethyldisilane To a solution of 4.802 g (25.7 mmol) 1,2-dichloro-1,1,2,2-tetramethyldisilane in 50 mL dimethylether was slowly added a solution of 2.285 g (12.8 mmol) sodium 1,2,3,4-tetramethylcyclopentadienide in 30 mL dimethylether. The reaction mixture was stirred several hours, then the solvent was removed, the residue was extracted with pentane and filtered. The pentane was removed under reduced pressure to give the product as a light-yellow oil. Mass spec: m/e 272 (8%). $^1$H NMR (C$_6$D$_6$) δ 2.70 (s, 1H), 1.83 (s, 6H), 1.69 (s, 6H), 0.28 (s, 6H), 0.23 (s, 6H); $^{13}$C NMR (C$_6$D$_6$) δ 135.8, 134.0, 54.4, 14.6, 11.4, 3.2, −2.4.

1-(tert-Butylamino)-2-(tetramethylcyclopentadienyl)-1,1,2,2-tetramethyldisilane

To a solution of 3.000 g (11.0 mmol) 1-chloro-2-(tetramethylcyclopentadienyl)-1,1,2,2-tetramethyldisilane in 50 mL ether was added 2.422 g (33.1 mmol) tert-butylamine. Precipitate formed rapidly. The slurry was stirred for several days at room temperature, then was gently heated to drive the reaction to completion. The solvent was removed, the residue was extracted with pentane, the amine hydrochloride was filtered and the pentane was removed under reduced pressure to give the product as a yellow oil. The yield was 3.150 (92.5%). Mass spec: m/e 309. $^1$H NMR (C$_6$D$_6$) δ 2.75 (s, 1H), 1.95 (s, 6H), 1.82 (s, 6H), 1.08 (s, 9H), 0.51 (s, 1H), 0.24 (s, 6H), 0.16 (s, 6H); $^{13}$C NMR (C$_6$D$_6$) δ 135.2, 134.4, 55.2, 50.3, 34.1, 14.9 11.6, 3.3, −1.4.

Dilithium 1-(tert-Butylamido)-2-(tetramethyl-cyclopentadienyl)-1,1,2,2-tetramethyldisilane To a solution of 3.00 g (9.72 mmol) 1-(tert-butylamino)-2-(tetramethylcyclopentadienyl)-1,1,2,2-tetramethyldisilane in 100 mL ether was slowly added 7.70 mL of 2.60 M (20.2 mmol) butyl lithium in mixed C6 alkane solvent. The resulting slurry was stirred several hours, then filtered and washed with ether, then dried under reduced pressure to give the product as a white powder. The yield was 2.918 g (93.4%). $^1$H NMR THF d-8) δ 2.05 (s, 6H), 1.91 (s, 6H),0.87 (s, 9H), 0.25 (s, 6H), −0.03 (3, 6H); $^{13}$C NMR (THF d-8) δ 117.3, 113.6, 53.5, 38.4, 34.1, 14.2 11.3, 8.4, 2.2.

1-(tert-Butylamido)-2-(tetramethyl-η$^5$-cyclopentadienyl)-1,1,2,2-tetramethyldisilane Titanium Dichloride A slurry of 0.7500 g (2.333 mmol)dilithium 1-(tert-butylamido)-2-(tetramethylcyclopentadienyl)-1,1,2,2-tetramethyldisilane and 0.7790 g (2.333 mmol) TiCl$_4$(THF)$_2$ in 50 mL toluene was stirred for several days. The red-orange reaction mixture was filtered and the solvent was removed to give a sticky red solid. This was extracted with pentane and filtered. After concentration and cooling at −35° C. in a freezer, the shiny microcrystalline red product was collected on a frit and washed with cold pentane to remove a dark red oily material. Yield: 0.3643 g, 36.6%. $^1$H NMR (C$_6$D$_6$) δ 2.20 (s, 6H), 1.94 (s, 6H), 1.48 (s 9H), 0.44. (s, 6H), 0.43 (s, 6H). $^{13}$C NMR (C$_6$D$_6$) δ 137.7, 135.5, 112.7, 65.9, 35.4, 16.6, 12.5, 2.8, −2.1.

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 12.1 g, Mw=62, 400, Mw/Mn=8.45, melt index=6.14, density=0.9441.

EXAMPLE 85

Preparation of 1-(tert-Butylamido)-2-(tetramethyl-η$^5$-cyclopentadienyl)-1,1,2,2-tetramethyldisilanezirconium Dichloride A slurry of 0.7500 g (2.333 mmol) dilithium 1-(tertbutylamido)-2-(tetramethylcyclopentadienyl)-1,1,2,2-tetramethyl-disilane (prepared according to the technique of Example 84) and 0.5436 g (2.333 mmol) ZrCl$_4$ in 75 mL toluene was stirred for several days. The pale yellow reaction mixture was filtered and the solvent was removed. The residue was extracted with pentane and filtered. After concentration and cooling at −35° C. in a freezer, the product as colorless crystals was collected on a frit. Yield: 0.6720 g, 61.3%. $^1$H NMR (C$_6$D$_6$) δ 2.14 (s, 6H), 1.94 (s, 6H), 1.49 (s, 9H), 0.36 (s, 6H), 0.34 (s, 6H). $^{13}$C NMR (C$_6$D$_6$) δ 134.1, 131.0, 119.1, 58.4, 34.2, 15.1, 11.8, 4.7, −2.1.

EXAMPLE 86

Preparation of (tert-Butylamido)(dimethyl)(tetramethyl-η$^5$-cyclopentadienyl)silanezirconium Dimethyl A solution of 0.5000 g (1.215 mmol) (tert-butylamido)(dimethyl)(tetramethylcyclopentadienyl)silanezirconium dichloride in 35 mL ether was cooled to −40° C. To this was slowly added 1.41 mL methyl lithium solution (1.72 M, 2.43 mmol). The reaction mixture was allowed to stir at room temperature for several hours. The solvent was removed and the residue was extracted with pentane and filtered. The filtrate was concentrated and chilled to −40° C. The colorless crystals which formed were isolated by decanting away the supernatant. Yield: 0.2215 g, 49.2% $^1$H NMR (C$_6$D$_6$) δ 1.97 (s, 6H), 1.91 (s, 6H), 1.40 (s, 9H), 0.46 (s, 6H), 0.00 (s, 6H). $^{13}$C NMR (C$_6$D$_6$) δ 130.2, 125.3, 95.7, 54.7, 35.4, 34.0, 13.9, 10.9, 6.2.

EXAMPLE 87

Preparation of Preparation of (tert-Butylamido)dimethyl($\eta^5$-cyclopentadienyl)silanetitanium Dichloride (Chloro)(cyclopentadienyl)(dimethyl)silane A solution of 149 g (1.16 mol) Me$_2$SiCl$_2$ in 750 mL diethyl ether was cooled to −78° C. Solid sodium cyclopentadienide (30 g, 0.341 mol) was added via a powder addition funnel over a period of 1.5 hours. The reaction mixture was allowed to warm to room temperature and was stirred for 16 hours. The ether and some Me$_2$SiCl$_2$ were distilled out, then exhaustive vacuum distillation removed the remaining ether, Me$_2$SiCl$_2$ and the product from the NaCl formed in the reaction. The product after fractionation was obtained in good yield as a light-yellow oil. Mass spec: m/e 158 (16%).

(tert-Butylamino)(cyclopentadienyl)(dimethyl)silane

To a solution of 3.69 g (50.4 mmol) tert-butyl amine in 45 mL THF was added 2.00 g (12.6 mmol) (chloro)(cyclopentadienyl)(dimethyl)silane. Precipitate formed quickly. The slurry was stirred for several days, then the amine hydrochloride was filtered off and the solvent was removed under reduced pressure to give the product as a very pale yellowish oil. The yield was 2.069 g (84.2%). Mass spec: m/e 195 (6%). $^1$H and $^{13}$C NMR show the presence of several cyclopentadiene isomers.

Dilithium (tert-Butylamido)(cyclopentadienyl)(dimethyl)silane

To a solution of 1.500 g (7.69 mmol) (tertbutylamido)(cyclopentadienyl)(dimethyl)silane in 60 mL ether was slowly added 6.21 mL of a 1.72 M (10.68 mmol) ether solution of methyllithium, then 1.81 mL of 2.6 M (4.706 mmol) butyllithium in mixed alkane solvent (15.39 mmol total alkyllithiums). The resulting slurry was stirred overnight, then filtered and washed with pentane, then dried under reduced pressure to give the product as a white powder. The yield was 1.359 g (85.2%). $^1$H NMR (THF d-8) δ 5.96 (t, 2H), 5.87 (t, 2H), 1.10 (s, 9H), 0.05 (s, 6H). $^{13}$C NMR (THF d-8) d 114, 105.2, 103.5, 52, 38.3, 7.3.

(Tertbutylamido)dimethyl($\eta^5$-cyclopentadienyl)silane Titanium Dichloride 0.7000 g (3.38 mmol) Dilithium (tertbutylamido)(cyclopentadienyl)(dimethyl)silane and 1.128 g (3.38 mmol) TiCl$_4$.(THF)$_2$ were combined in a flask with 75 mL toluene. The resulting yellow slurry turned muddy red-brown within a few hours. The reaction mixture was stirred for several days then the red solution was filtered and the solvents removed under reduced pressure. The crystalline material formed was slurried with pentane and filtered to remove the soluble red impurity from the brown product. The yield was 0.5369 g (50.9%). $^1$H NMR (C$_6$D$_6$) δ 6.60 (t, 2H), 6.07 (t, 2H), 1.38 (s, 9H), 0.18 (s, 6H). $^{13}$C NMR (C$_6$D$_6$) δ 126.3, 125.6., 110.0,63.7, 32.2, −0.2.

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 28.1 g, Mw=108,000, Mw/Mn=3.22, density=0.9073, melt index= 2.92.

EXAMPLE 88

Preparation of (tert-Butylamido)dimethyl($\eta^5$-cyclopentadienyl)silane Zirconium Dichloride To 0.6747 g (2.90 mmol) ZrCl$_{14}$ in a flask was slowly added 4 mL diethyl ether, then 4 mL THF. The excess solvents were removed under vacuum to yield a solid which was broken up to a powder. The solid was combined with 0.6008 g (2.90 mmol) dilithium (tertbutylamido)(cyclopentadienyl)(dimethyl)silane (prepared according to the technique of Example 87 and 75 mL toluene. The resulting slurry was stirred for several days after which the colorless solution was filtered, the solvent removed under reduced pressure and the residue was slurried in pentane. The product was collected on a frit and dried under reduced pressure. Yield was 0.6186 g (60.0%). $^1$H NMR (C$_6$D$_6$) δ 6.43 (t, 2H), 6.08 (t, 2H), 4.17 (br s, 6H), 1.27 (s, 9H), 1.03 (br s, 6H), 0.22 (s, 6H). $^{13}$C NMR (C$_6$D$_6$) δ 122.0, 121.4, 109.5, 78, 57.2, 32.8, 25.2, 0.7. The structure was shown by x-ray crystallography to be dimeric (bridging chlorides) in the solid state.

Example 89

Preparation of (Anilido)(dimethyl)(tetramethyl-$\eta^5$-cyclopentadienyl)silanetitanium Dichloride (Anilido)(dimethyl)(tetramethylcyclopentadienyl)silane To a solution of 1.500 g (6.98 mmol) (chloro)(dimethyl)(tetramethylcyclopentadienyl)silane in 50 mL THF was slowly added 0.6911 g (6.98 mmol) lithium anilide. Monitoring by GC indicated the reaction was incomplete. Additional lithium anilide (0.08 g, 7.78 mmol total) was added. The reaction mixture was stirred overnight. The solvent was removed, the residue was extracted with pentane and filtered. The pentane was removed under reduced pressure to give the product as a pale yellow oil. The yield was 1.875 g (99.2%). Mass spec. m/e 271 (13%). $^1$H NMR (C$_6$D$_6$) δ 7.14 (m, 2H), 6.76 (t, 1H), 6.60 (d, 2H), 3.08 (s, 1H), 3.04 (s, 1H), 1.89 (s, 6H), 1.79 (s, 6H), 0.07 (s, 6H). $^{13}$C NMR (C$_6$D$_6$) δ 147.5, 136.3, 132.6, 129.6, 118.2, 116.9, 55.0, 14.3, 11.3, −2.2.

Dilithium (Anilido)(dimethyl)(tetramethylcyclopentadienyl)silane

To a solution of 1.875 g (6.91 mmol) (anilido)(dimethyl)(tetramethylcyclopentadienyl)silane in 50 mL ether was slowly added 5.31 mL of 2.60 M (13.8 mmol) butyllithium in hexane solvent. A small amount of precipitate formed, but then dissolved. The reaction mixture was stirred overnight. The product appeared to have collected as a thick viscous oil in the ether solution The solvent was removed under reduced pressure. The resulting white solid was slurried in pentane, collected on a frit, washed with pentane and dried under reduced pressure to give the product as a white powder. The yield was 1.943 g (99.3%).

(Anilido)(dimethyl)(tetramethyl-$\eta^5$-cyclopentadienyl)silanetitanium Dichloride A slurry of 0.8025 g (2.333 mmol) dilithium (anilido)(dimethyl)(tetramethylcyclopentadienyl)silane and 0.9871 g (2.333 mmol) TiCl$_4$(THF)$_2$ in 70 mL toluene was stirred for several days. The red-brown reaction mixture was filtered and the solvent was removed. The solid was triturated in pentane and the product was collected on a frit and washed with cold pentane to remove a dark red oily material to give the product as a yellow-beige powder. Yield: 0.6400 g, 55.8%. $^1$H NMR ($C_6D_6$) δ 7.32 (d, 2H), 7.18 (m, 2H), 6.85 (t, 1H), 2.02 (s, 6H), 1.99 (s, 6H), 0.42 (s, 6H). $^{13}$C NMR ($C_6D_6$) δ 152.4, 141.9, 137.8, 129.3, 124.4, 119.6, 105.3, 16.1, 13.0, 2.7.

Polymerization 1

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 12.8 g, Mw=103,000, Mw/Mn=4.77, density 0.9387, melt index= 6.37.

Polymerization 2 Ethylene/Styrene Copolymerization

The above polymerization procedure was substantially followed except that 900 mL of mixed alkane solvent, 184 mL of styrene, 345 kPa delta hydrogen, and 20 micromoles of [($C_5Me_4$)$SiMe_2$(tertbutyl)]$TiCl_2$ were used. The temperature of the reactor was 120° C. After 10 minutes, the contents were removed from the reactor, and 62.3 g of polymer was recovered. The melt index was 3.68.

EXAMPLE 90

Preparation of (Anilido)(dimethyl)(tetramethyl-$\eta^5$-cyclopentadienyl)silanezirconium Dichloride To 0.6905 g (2.963 mmol) $ZrCl_4$ in a flask was slowly added 3 mL diethyl ether, then 4 mL THF. The excess solvents were removed under vacuum to yield a solid which was broken up to a powder. The solid was combined with 0.8044 g (2.963 mmol) dilithium (anilido)(dimethyl)(tetramethyl-$\eta^5$-cyclopentadienyl)silane and 70 mL toluene. Within minutes the slurry color became pale yellow-green. The slurry was stirred for several days after which time the solution was filtered, the solvent removed under reduced pressure and the residue was slurried in pentane. The very pale yellowish product was collected on a frit and dried under reduced pressure. $^1$H NMR ($C_6D_6$) δ 7.21 (t, 2H), 7.1 (t, 1H), 6.97 (m, 2H), 2.50 (s, 3H), 2.46 (s, 3H), 1.87 (s, 3H), 1.85 (s, 3H), 0.53 (s, 3H), 0.40 (s, 3H).

EXAMPLE 91

Preparation of (p-Toluidino)(dimethyl)(tetramethyl-$\eta^5$-cyclopentadienyl)silanezirconium Dichloride (p-Toluidino)(dimethyl)(tetramethylcyclopentadienyl)silane To a solution of 2.000 g (9.302 mmol) (chloro)(dimethyl)(2,3,4,5-tetramethylcyclopentadienyl)silane in 70 mL THF was slowly added 1.259 g (9.302 mmol) lithium p-toluidide (0.3 ether adduct by $^1$H NMR). The reaction mixture was stirred overnight. Monitoring by GC indicated the reaction was incomplete. Additional lithium p-toluidide was added in small lots (0.725 g, 14.7 mmol total). The solvent was removed, the residue was extracted with pentane and filtered. The pentane was removed under reduced pressure to give the product as a yellow oil. The yield was 2.456 g (92.5%). Mass spec. m/e 285 (22%). $^1$H NMR ($C_6D_6$) δ 6.96 (d, 2H), 6.57 (d, 2H), 3.07 (s, 1H), 3.01 (s, 1H), 2.17 (s, 3H), 1.91 (s, 6H), 1.80 (s, 6H), 0.08 (s, 6H). $^{13}$C NMR ($C_6D_6$) δ 145.0, 136.2, 132.7, 130.2, 126.9, 116.9, 55.2, 20.5, 14.3, 11.3, −2.2.

Dilithium (p-Toluidino)(dimethyl)(tetramethylcyclopentadienyl)silane

To a solution of 2.233 g (7.82 mmol) (p-toluidino)(dimethyl)(tetramethylcyclopentadienyl)silane in 65 mL ether was slowly added 6.17 mL of 2.60 M (16.0 mmol) butyllithium in mixed $C_6$ alkane solvent. The precipitate-free reaction mixture was stirred overnight. The solvent was removed under reduced pressure. The resulting white solid was slurried in pentane, collected on a frit, washed with pentane and dried under reduced pressure to give the product as a white powder. The yield was 2.34 g (100%). $^1$H NMR (THF δ-8) d 6.42 (d, 2H), 6.18 (d, 2H), 2.09 (s, 6H), 2.01 (s, 3H), 1.94 (s, 6H), 0.36 (s, 6H). $^{13}$C NMR (THF δ-8) δ 160.8, 129.1, 121.3, 115.9, 115.2, 112.2, 106.2, 20.8, 14.7, 11.7, 5.2.

(p-Toluidino)(dimethyl)(tetramethyl-$\eta^5$-cyclopentadienyl)silanetitanium Dichloride A slurry of 1.000 g (3.363 mmol) dilithium (p-toluidino)(dimethyl)(tetramethyl-$\eta^5$-cyclopentadienyl)silane and 1.123 g (3.363 mmol) $TiCl_{14}(THF)_2$ in 70 mL toluene. The reaction mixture was stirred several days, then filtered and the solvent was removed. The resulting solid was slurried in pentane and the product was collected on a frit and dried under reduced pressure. The yield of olive-brown powder was 0.7172 g, 53.0%. $^1$H NMR ($C_6D6$) δ 7.26 (d, 2H), 7.01 (d, 2H), 2.08 (s, 3H), 2.04 (s, 6H), 2.00 (s, 6H), 0.45 (s, 6H). $^{13}$C NMR ($C_6D6$) δ 150.3, 141.7, 137.5, 133.9, 130.0, 129.7, 119.6, 21.0, 20.6, 16.4, 16.0, 13.3, 12.8, 2.8, 2.6.

(p-Toluidino)(dimethyl)(tetramethyl-$\eta^5$-cyclopentadienyl)silanezirconium Dichloride To 0.7836 g (3.363 mmol) $ZrCl_4$ in a flask was slowly added 3 mL diethyl ether, then 4 mL THF. The excess solvents were removed under vacuum to yield a solid which was broken up to a powder. The solid was combined with 1.000 g (3.363 mmol) dilithium (p-toluidino)(dimethyl)(tetramethyl-$\eta^5$-cyclopentadienyl)silane and 70 mL toluene. The slurry was stirred for several days. The initially yellowish slurry turned brownish. The yellow solution was filtered, the solvent removed under reduced pressure and the solid was slurried in pentane. The pale yellow product was collected on a frit and dried under reduced pressure. The yield was 0.8854 g (59.1%). $^1$H NMR ($C_6D_6$) δ 7.06 (d, 2H), 6.87 (d, 2H), 2.50 (s, 3H), 2.47 (s, 3H), 2.21 (s, 3H), 1.89 (s, 3H), 1.88 (s, 3H), 0.51 (s, 3H), 0.41 (s, 3H). The structure was shown by x-ray crystallography to be a LiCl-containing dimer with bridging chlorides.

EXAMPLE 92

Preparation of (Benzylamido)dimethyl(tetramethyl-$\eta^5$-cyclopentadienyl)silanetitanium Dichloride (Benzylamino)dimethyl(tetramethylcyclopentadienyl)silane To a solution of 1.000 g (4.651 mmol) (chloro)(dimethyl)(tetramethylcyclopentadienyl)silane in 70 mL ether was slowly added 0.526 g (4.651 mmol) lithium benzylamide. The reaction mixture was stirred overnight, then the solvent was removed, the residue was extracted with pentane and filtered. The pentane was removed under reduced pressure to give the product as a pale yellow oil. The yield was 1.234 g (93.3%). Mass spec. m/e 285 (18%). $^1$H NMR (C$_6$D$_6$) δ 7.0–7.24 (m, 5H), 3.71 (d, 2H), 2.73 (br s, 1H), 1.88 (s, 6H), 1.76 (s, 6H), 0.43 (br t, 1H), −0.07 (s, 6H). $^{13}$C NMR (C$_6$D$_6$) δ 144.5, 135.7, 132.0, 128.5, 127.3, 126.7, 56.7, 46.4, 14.6, 11.4, −2.3.

Dilithium (Benzylamido)dimethyl(tetramethylcyclopentadienyl)silane

To a solution of 1.091 g (3.836 mmol) (benzylamino)(dimethyl)(tetramethylcyclopentadienyl)silane in 70 mL ether was slowly added 3.1 mL of 2.60 M (8.06 mmol) butyl lithium in mixed C$_6$ alkane solvent. A pale pink color forms along with precipitate. The reaction mixture was stirred overnight. The solvent was removed under reduced pressure. The resulting solid was slurried in pentane, collected on a frit, washed with pentane and dried under reduced pressure to give the product as a very pale pink powder. The yield was 1.105 g (96.9%). $^1$H NMR (THF d-8) d 7.15 (m, 4H), 7.00 (t, 1H), 4.02 (s, 2H), 2.04 (s, 6H), 1.79 (s, 6H), −0.15 (s, 6H). $^{13}$C NMR (THF d-8) d 152.1, 128.1, 127.9, 125.0, 115.8, 111.9, 108.3, 54.0, 15.0, 11.2, 4.6.

(Benzylamido)dimethyl(tetramethyl-η$^5$-cyclopentadienyl)silanetitanium Dichloride A slurry of 0.5052 g (1.699 mmol) dilithium (benzylamido)(dimethyl)(tetramethyl-η$^5$-cyclopentadienyl)silane and 0.5673 g (1.699 mmol) TiCl$_4$(THF)$_2$ in 40 mL toluene was stirred for several days. The dark green-brown reaction mixture was filtered and the solvent was removed. The dark oily residue was slurried in pentane and the product was collected on a frit and washed with cold pentane to remove a dark oily material to give the product as a greenish yellow powder. Yield: 0.2742 g (40.1%). $^1$H NMR (C$_6$D$_6$) δ 7.19 (m, 2H), 7.02 (m, 3H), 5.37 (s, 2H), 1.99 (s, 6H), 1.98 (s, 6H), 0.03 (s, 6H). $^{13}$C NMR (C$_6$D$_6$) δ 141.4, 140.9, 135.8, 129.0, 128.8, 126.9, 126.6, 126.3, 111.6, 103.6, 59.3, 15.6, 12.4, 1.7.

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 14.4 g, Mw=Mw/Mn=5.0, melt index=251, density=0.9690.

EXAMPLE 93

Preparation of (Benzylamido)dimethyl(tetramethyl-η$^5$-cyclopentadienyl)silanezirconium Dichloride In a flask were combined 0.3930 g (1.687 mmol) ZrCl$_4$, 0.5015 g (1.687 mmol) dilithium (benzylamido)dimethyl (tetramethyl-η$^5$-cyclopentadienyl)silane and 40 mL toluene. The brownish yellow slurry was stirred for several days then filtered and the solvent was removed under reduced pressure. The moist tan residue was slurried in pentane and the product was collected on a frit and dried under reduced pressure. Yield of the off-white tan product: 0.2873 g (38.2%). $^1$H NMR (C$_6$D$_6$) δ 7.51 (d, 2H), 7.23 (t, 2H), 7.09 (t, 1H), 5.48 (d, 1H), 5.00 (d, 1H), 2.45 (s, 6H), 2.05 (s, 3), 2.01 (s, 3H), 0.34 (s, 3H), 0.20 (s, 3H). $^{13}$C NMR (C$_6$D$_6$) δ 145–2, 135.1, 132.2, 131.8, 129.4, 129.0, 128.9, 128.8, 127.0, 126.6, 126.3, 106.6, 57.2, 16.0, 15.6, 12.5, 11.8, 2.6.

EXAMPLE 94

Preparation of (Phenylphosphino)dimethyl (tetramethyl-η$^5$-cyclopentadienyl)silanetitanium Dichloride (Phenylphosphino)(dimethyl)(tetramethylcyclopentadienyl)silane To a solution of 1.500 g (6.983 mmol) (chloro)(dimethyl)(tetramethylcyclopentadienyl)silane in 55 mL THF was slowly added 1.1248 g (7.665 mmol, excess added as GC monitoring indicated 1:1 reaction was incomplete) lithium phenylphosphide (0.4 ether adduct by $^1$H NMR spectroscopy). The reaction mixture was stirred several days, then the solvent was removed, the residue was extracted with pentane and filtered. The pentane was removed under reduced pressure to give the product as a yellow oil. The yield was 1.985 g (98.5%).

Dilithium (Phenylphosphido)dimethyl(tetramethylcyclopentadienyl)silane

To a solution of 1.858 g (6.451 mmol) (phenylphosphino)(dimethyl)(tetramethylcyclopentadienyl) silane in 65 mL ether was slowly added 5.21 mL of 2.60 M (13.55 mmol) butyllithium in mixed C$_6$ alkane solvent with the formation of a yellowish precipitate. The reaction mixture was stirred overnight. The product was collected on a frit and washed with pentane, then dried under reduced pressure to give the product as a white powder. The yield (0.5 ether adduct by $^1$H NMR spectroscopy) was 2.0845 g (95.8%).

(Phenylphosphido)dimethyl(tetramethyl-η$^5$-cyclopentadienyl)silanetitanium Dichloride In a flask were combined 0.900 g (2.668 mmol) dilithium (phenylphosphido)(dimethyl)(tetramethyl-η$^5$-cyclopentadienyl)silane (0.5 ether adduct) and 0.8907 g (2.668 mmol) TiCl4(THF)2 with 75 mL toluene. The color instantly changed to deep green-black on addition of toluene. The reaction mixture was stirred for several days, then was filtered and the solvent was removed. The dark residue was extracted with pentane and filtered to leave a green-brown product on the frit (0.2477 g) and a black glassy product on removal of the pentane from the filtrate.

Polymerization

The polymerization procedure of Examples 11–33 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 14.4 g, Mw=27, 700, Mw/Mn=5.0, melt index=251, density=0.9690.

EXAMPLE 95

Preparation of (Phenylphosphido)dimethyl (tetramethyl-η$^5$-cyclopentadienyl)silanezirconium Dichloride To 0.6217 g (2.668 mmol) ZrCl$_4$ in a flask was slowly added 3 mL diethyl ether. The excess solvent was removed under vacuum to yield a solid which was broken up to a powder. The solid was combined with 0.9000 g (2.668 mmol) dilithium (phenylphosphido)dimethyl(tetramethyl-$\eta^5$-cyclopentadienyl)silane and 75 mL toluene. The color changed to deep red-orange on addition of toluene. The reaction mixture was stirred for several days, then the orange solution was filtered from a large quantity of dark insoluble material and the solvent was removed. The residue was slurried with pentane and filtered. A brown solid was collected on a frit and dried under reduced pressure.

EXAMPLE 96

Preparation of (tert-Butylamido)dimethyl(indenyl) silanetitanium Dichloride (tert-Butylamino)dimethyl(indenyl)silane To a solution of 5.255 g (71.8 mmol) tert-butyl amine in 75 mL ether was added 3.000 g (14.4 mmol) 9-(chlorodimethylsilyl)indene. Precipitate formed within a few minutes of the start of the addition. The slurry was stirred overnight, then the solvent was removed, the residue was extracted with pentane and filtered. The pentane was removed under reduced pressure to give the light-yellow oil product as a mixture of two isomers. The yield was 3.313 g, (93.9%).

Dilithium (tert-Butylamido)dimethyl(indenyl)silane

To a solution of 3.125 g (12.73 mmol) (tert-butylamino) dimethyl(indenyl)silane in 75 mL ether was slowly added 10.28 mL of 2.60 M (26.73 mmol) butyllithium in mixed $C_6$ alkane solvent. The color of the precipitate-free solution darkens slightly to beige-orange. The reaction mixture was stirred several days, then the solvent was removed. The fluffy, glassy material was slurried with pentane. The powder clumps together. The pentane was decanted and the washing procedure was repeated several times, then the solid was dried under reduced pressure. The yield was 2.421 g (73.9%).

(tert-Butylamido)dimethyl(indenyl)silanetitanium Dichloride

In a flask were combined 1.000 g (3.887 mmol) dilithium (tertbutylamido)(dimethyl)(indenyl)silane and 1.298 g (3.887 mmol) $TiCl_4(THF)_2$ with 70 mL toluene. A deep red color developed instantly. The reaction mixture was stirred three days, then filtered, and the solvent was removed. The residue was extracted with pentane and filtered to give the product as a red microcrystalline material. The yield was 0.4917 g (34.9%).

Polymerization

The polymerization procedure of Examples 11–32 was substantially followed. The reaction temperature was 130° C. The reactor was filled with 1000 mL of isopar-E, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 14.8 g.

EXAMPLE 97

Preparation of (tert-Butylamido)dimethyl(indenyl) silanezirconium Dichloride

To 0.9057 g (3.887 mmol) $ZrCl_4$ in a flask was slowly added 2 mL THE. The excess THF was removed under vacuum to yield a solid which was broken up to a powder. 1.000 g (3.887 mmol) dilithium (tertbutylamido)dimethyl (indenyl)silane was added along with 70 mL toluene. The resulting slurry was stirred for several days after which the solution was filtered and the solvent removed under reduced pressure. The residue was slurried in pentane, filtered and dried under reduced pressure. The yield of brown-biege product was 0.5668 g (36.0%).

EXAMPLE 98

Preparation of (Methylamido)dimethyl(tetramethyl-$\eta^5$-cyclopentadienyl)silanetitanium Dichloride (Methylamino)dimethyl(tetramethyl-$\eta^5$-cyclopentadienyl)silane To a solution of 1.900 g (8.845 mmol) (chloro)(dimethyl) (tetramethylcyclooentadienyl)silane in 75 mL THF was quickly added 0.3272 g (8.846 mmol) lithium methylamide. The clear solution was stirred overnight, then additional lithium methylamide (0.008 g, 9.062 mmol total) was added as gas chromatography (GC) indicated the reaction was incomplete and the solution was stirred overnight again. The solvent was removed, the residue was extracted with pentane and filtered, and the pentane was removed under reduced pressure to give the product as a very pale yellow oil. The yield was 1.698 g (91.7%). Mass spec. m/e 209 (13 percent). $^1$H NMR ($C_6D_6$): δ 2.82 (s, 1H), 2.33 (d, J=6.6 Hz, 3H), 1.95 (s, 6H), 1.83 (s, 6H), −0.04 (s, 6H). $^{13}$C NMR ($C_6D_6$): δ 135.4, 132.7, 56.1, 27.8, 14.0, 11.0, −3.5.

Dilithium(methylamido)dimethyl (tetramethylcyclopentadienyl)silane

To a solution of 1.563 g (7.463 mmol) (methylamino) (dimethyl)(tetramethylcyclopentadienyl) silane in about 65 mL ether/pentane (1:1) was slowly added 6.03 mL of 2.60 M (15.7 mmol) butyllithium in mixed $C_6$ alkane solvent. The solution turned to a thick syrup which broke down to a slurry. The reaction mixture was stirred overnight, then filtered. The solid was washed several times with ether, then with pentane, then dried under reduced pressure to give the product as a white powder. The yield was 1.883 g of a 0.25 ether adduct as determined by $^1$H NMR spectroscopy. $^1$H NMR (THF δ-8) δ 3.41 (q, J=7.0 Hz, 1H), 2.45 (s, 3H), 2.01 (s, 6H), 1.93 (s, 6H), 1.11 (t, J=7.01, .5H), 0.01–0.14 (br, 6H).

(Methylamido)dimethyl(tetramethyl-$\eta^5$-cyclopentadienyl)silanetitanium Dichloride To a solution of 0.6708 g (2.597 mmol) dilithium (methylamido)dimethyl(tetramethyl-$\eta^5$-cyclopentadienyl) silane in 80 mL THF was added all at once 0.9623 g (2.597 mmol) $TiCl_3(THF)_3$. The solution immediately turned intense brown-orange. The reaction mixture was stirred four days, then 1.861 g (12.98 mmol) AgCl was added. The slurry was stirred several days after which the reaction mixture was filtered and the solvents were removed under reduced pressure. The residue was extracted with toluene, the dark orange-brown solution was filtered and the solvent was removed. After extraction with pentane and filtration, the filtrate was concentrated to a light brown slurry in a dark red solution. After cooling to −30° C., the bright yellow product was collected on a frit, washed with pentane and dried under reduced pressure. The yield was 0.3168 g (37.4%). $^1$H NMR ($C_6D_6$): δ 3.64 (s,3H), 1.97 (s, 6H), 1.95 (s, 6H), 0.21 (s, 6H). $^{13}$C NMR ($C_6D_6$): δ 140.5, 135.5, 103.0, 41.8, 15.5, 12.3, 0.6.

Polymerization

The polymerization procedure of Examples 11–32 was substantially followed. The reaction temperature was 130°

C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 30.2 g.

EXAMPLE 99

Preparation of (Methylamido)dimethyl(tetramethyl-$\eta^5$-cyclopentadienyl)silanezirconium Dichloride In a flask 0.5705 g (2.448 mmol) $ZrCl_4$ and 0.6318 g (2.446 mmol) dilithium (methylamido)dimethyl (tetramethyl-$\eta^5$-cyclopentadienyl)silane were combined with 75 mL toluene. The slurry was stirred for several days after which time the resulting pale green solution was filtered, and the solvent was removed under reduced pressure. The residue was slurried in pentane, collected on a frit, washed with pentane and dried under reduced pressure. The yield of very pale powder blue product was 0.6162 g (68.2%). $^1$H NMR ($C_6D_6$): δ 3.50 (s, 3H), 2.49 (s, 3H) 2.36 (s, 3H), 2.14 (s, 3H), 2.10 (s, 3H), 0.46 (s, 3H), 0.43 (s, 3H).

EXAMPLE 100

Preparation of 1-(tert-Butylamido)-2-(tetramethyl-$\eta^5$-cyclopentadienyl)ethanediyltitanium Dichloride Ethyl 2-(Tetramethylcyclopentadienyl)acetate A solution of 3.822 g (22.89 mmol) ethyl bromoacetate in 25 mL THF was cooled to −78° C. and 3.000 g (20.80 g) sodium tetramethylcyclopentadienide in 50 mL THF was slowly added to it. The resulting slurry was allowed to warm to room temperature and was stirred overnight. The solvent was removed, the residue was extracted with pentane and filtered. The pentane was removed to give a mixture of isomers. Yield was 3.733 g (86.3%). Mass spectra m/e 208 (41 percent).

2-(Tetramethylcyclopentadienyl)tert-butyl Acetamide 16.35 mL of 2.00 M (32.7 mmol) trimethyl aluminum in toluene was added to 2.39 g (32.7 mmol) tert-butylamine in 50 mL toluene. The solution was stirred for 45 minutes, then 3.40 g ethyl-2-tetramethylcyclopentadienyl acetate was added. The reaction mixture was stirred for several days while gently warming. After aqueous workup the product amide was obtained as a mixture of three isomers as an orange semicrystalline paste. Mass spectra m/e 235 (21%).

1-(tert-Butylamino)-2-(tetramethylcyclopentadinyl) ethane

The amide mixture was dissolved in 120 mL ether and 0.830 g (21.8 mmol) lithium aluminum hydride was added. The reaction mixture was stirred overnight under gentle heating. Monitoring by GC indicated the reaction was incomplete. The ether was replaced by THF, more lithium aluminumhydride was added and the solution was refluxed for several days. After aqueous workup three 1-(tert-butylamino)-2-(tetramethylcyclopentadienyl)ethane isomers were obtained. Mass spectra m/e 221 (11%).

Dilithium 1-(Tertbutylamido)-2-(tetramethyl-$\eta^5$-cyclopentadienyl)ethane

To a solution of 2.00 g (9.05 mmol) (tertbutylamino)-2-(tetramethylcyclopentadienyl)ethane isomers (67% 1-(tertbutylamino)-2-(2,3,4,5-tetramethylcyclopentadi-2,4-enyl)ethane by GC, 1.34 g (6.06 mmol)) in 50 mL ether was slowly added 6.09 mL of 2.60 M (15.8 mmol) butyllithium in mixed $C_6$ alkane solvent with formation of a yellow precipitate. The reaction mixture was stirred three days, then filtered. The light yellow powder was washed several times with ether, then dried under reduced pressure. The yield was 0.7908 g (55.9%). $^1$H NMR (THF d-8): δ 2.43 (br m, 4H), 1.85 (s, 6H), 1.83 (s, 6H), 1.00 (s, 9H). $^{13}$C NMR (THF d-8): δ 109.5, 107.3, 106.3, 50.5, 45.4, 29.4, 28.2, 20.2, 10.9, 10.8.

1-(tert-Butylamido)-2-(tetramethyl-$\eta^5$-cyclopentadienyl) ethanediyltitanium Dichloride In a flask 0.3650 g (1.565 mmol) dilithium 1-(tert-butylamido)-2-(tetramethylcyclopentadienyl)ethane and 0.5799 g (1.565 mmol) TiCl3(THF)$_3$ were combined with 60 mL THF. The solution quickly turned green. The reaction mixture was stirred overnight, then 1.121 g (7.82 mmol) AgCl was added. Within a few minutes the color began to change to brownish orange. The slurry was stirred two days and the solvents were removed under reduced pressure. The residue was extracted with toluene, the solution was filtered and the solvent was removed. The residue was extracted with pentane, filtered, concentrated, and cooled to −30° C. The bright orange product was collected on a frit, washed with a small amount of cold pentane and dried under reduced pressure. The yield was 0.1904 g (36.0%). $^1$H NMR ($C_6D_6$): δ 4.01 (t, J=7.2, 2H), 2.58 (t, J=7.2, 2H), 2.02 (s, 6H), 1.89 (s, 6H), 1.41 (s, 9H). $^{13}$C NMR ($C_6D_6$): δ 138.0, 129.3, 128.6, 69.1, 62.7, 28.6, 24.9, 13.0, 12.3.

Polymerization 1

The polymerization procedure of Examples 11–32 was substantially followed. The reaction temperature was 130° C. The reactor was filled with 1000 mL of isopar-E, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 64.8 g, melt index=3.21, density=0.9262.

Polymerization 2

The above polymerization procedure was repeated excepting that 0.95 micromoles of 1-(tert-butylamido)-2-(tetramethyl-$\eta^5$-cyclopentadienyl)ethanediyltitanium dichloride was added to begin the polymerization. The polymer yield was 11.4 g, melt index <0.1, density=0.9119.

Polymerization 3

The above polymerization procedure was repeated excepting that 2.5 micromoles of 1-(tert-butylamido)-2-(tetramethyl-$\eta^5$-cyclopentadienyl)ethanediyltitanium dichloride was added to begin the polymerization. In addition, 300 mL of octene and 900 mL of isopar was used, and no hydrogen was used. The polymer yield was 36.2 g, melt index=0.21, density=0.9190.

Polymerization 4

The conditions of above polymerization 1 were repeated excepting that the temperature was 90° C. and 345 kPa (50 psi) of hydrogen was used. The polymer yield was 66.7 g, melt index=0.16.

EXAMPLE 101

Preparation of 1-(tert-Butylamido)-2-(tetramethyl-$\eta^5$-cyclopentadienyl)ethanediylzirconium Dichloride In a flask 0.3862 g (1.657 mmol) $ZrCl_4$ and 0.3866 g (1.657 mmol) dilithium [1-(tert-butylamido)-2-(tetramethyl- $\eta^5$-cyclopentadienyl)ethane] were combined with 50 mL toluene. After stirring several days, 1 mL THF was added and the slurry was stirred for an additional day after which time the solution was filtered, and the solvent was removed under reduced pressure. The solid was slurried in pentane, collected on a frit, and dried under reduced pressure. Yield of pale yellow product was 0.6307 g (99.8%). $^1$H NMR ($C_6D_6$): δ 2.75 (t of d, 1H), 2.38 (m, 2H), 2.11, (s, 6H) 2.03 (s, 3H), 2.00 (s, 3H), 1.75 (t of d, 1H), 1.08 (s, 9H). $^{13}$C NMR ($C_6D_6$): δ 131.5, 128.7, 126.8, 126.5, 126.2, 56.9, 50.9, 27.9, 23.1, 13.4, 13.2, 12.6, 12.5.

EXAMPLE 102

Terpolymer Polymerization

Mixtures of ethylene, styrene and another additional polymerizable monomer were polymerized using (tert-butylamido)dimethyl(tetramethyl-$\eta^5$-cyclopentadienyl) silanetitanium dichloride complex and MAO cocatalyst in an amount to provide an atomic ratio Al/Ti of 1000:1. Reaction conditions and results are contained in Table VI.

Polymerization

The polymerization procedure of Examples 11–32 was substantially followed. The reaction temperature was 130° C. The reactor was filled with 1000 mL of mixed alkane solvent, 200 mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of the above complex was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 55.1 g, melt index=1.71.

EXAMPLE 105

The polymerization procedure of Examples 11–32 was substantially followed. The reaction temperature was 130° C. The reactor was filled with 1000 mL of mixed alkane, 200

TABLE VI

In each case the cocatalyst was methylaluminoxane and the metal complex was (tert-butylamido)dimethyl(tetramethyl-$\eta^5$-cyclopentadienyl)titanium dichloride.

| Run | mg (complex) | T (° C.) | Solvent (mL)[a] | Ethylene (kPa) | Styrene (mL) | Olefin (g) | Time (hr) | Yield (g) | mol % Styrene | mol % Olefin | $M_w$ | $M_w M_n$ |
|---|---|---|---|---|---|---|---|---|---|---|---|---|
| 1 | 1.8 | 90 | I (670) | 1517 | 38 | butene (19) | 0.5 | 51 | 2.3 | 6.6 | 141,000 | 2.9 |
| 2 | 1.9 | 90 | I (630) | " | 76 | butene (9) | 0.5 | 45 | 3.4 | 4.5 | 155,000 | 2.4 |
| 3 | 1.9 | 90 | I (455) | " | 250 | butene (5) | 0.5 | 70 | 7.2 | 3.2 | 153,000 | 2.4 |
| 4 | 2.2 | 90 | T (40) | 1241 | 133 | Vinyl-BCB (1.5)[b] | 2.0 | 37 | 22.4 | <1 | 39,000 | 1.7 |

[a]I = mixed alkane solvent, T = toluene
[b]Vinyl-BCB = vinyl benzocyclobutane

EXAMPLE 103

Slurry Polymerization

The following example demonstrates the use of a catalyst of the present invention under slurry conditions. The procedure of Examples 11–32 was substantially followed, excepting that the reaction was run under conditions where the polymer was insoluble in the reaction medium and precipitated from the reaction mixture as it formed. The temperature was 70° C., 10 mL of octene, 1190 mL of mixed alkane solvent, and 5 mL of 15 percent MAO in toluene (1280 Al:Ti) were used. After 20 minutes, the reactor was drained to give 4.6 g of polymer. Additional solvent was added to the reactor and heated to 170° C. to remove the polymer that had formed long filaments and wound around the stirrer. The melt index was 0.28.

EXAMPLE 104

Preparation of (tert-Butylamido)dimethyl (tetramethyl-$\eta^5$-cyclopentadienyl)silanetitanium(III) Chloride In the drybox, 0.24 g of $TiCl_3(THF)_3$ and 0.33 g of $Me_4C_5SiMe_2N$-t-$BuMg_2Cl_2(THF)_2$ were mixed. 15 mL of THF was added, resulting in a deep purple color. After 30 minutes the volatile materials were removed under reduced pressure to leave a dark solid. Toluene (15 mL) was added, the solution filtered, and the toluene was removed under reduced pressure to leave a red-purple powder, 0.22 g.

mL of 1-octene and 5 mL of 15 percent MAO in toluene (1280 Al:Ti). The reactor was saturated with 3102 kPa (450 psig) of ethylene, and a 75 mL tank of hydrogen was pressurized to 3447 kPa (500 psig) to give a delta pressure of 345 kPa (50 psi). The hydrogen was expanded into the reactor, and 10 micromoles of (tert-butylamido)dimethyl (tetramethyl-$\eta^5$-cyclopentadienyl)silanetitanium dichloride was added to begin the polymerization. Ethylene was provided on demand at 3102 kPa (450 psig). After 10 minutes, the solution was drained from the reactor into a container which had a small amount of antioxidant. The polymer was dried under vacuum. The polymer yield was 76.4 g, Mw=56,700, Mw/Mn=4.5, density=0.8871, melt index ($I_2$)=10.13.

EXAMPLE 106

The polymerization procedure of Example 105 was substantially followed except that the temperature was 80° C., the amount of catalyst used was 2.5 micromoles, the amount of 1-octene used was 250 mL, and the amount of mixed alkane solvent used was 950 mL. The reaction was allowed to proceed for 1 hour. The polymer yield was 51.1 g. The melt index was 0.11.

EXAMPLE 107

Preparation of (tert-Butylamido)dimethyl (tetramethylcyclopentadienyl)silanehafnium Dichloride In the drybox, 0.50 g of $HfCl_4$ was suspended in 10 mL of toluene. 10 mL Of THF was added, the slurry was stirred for 5 minutes, and 0.77 g of Me$_4$C$_5$SiMe$_2$N-t-BuMg$_2$Cl$_2$ (THF)$_2$ was added. The solution was heated to reflux. After 30 minutes, the solution was cooled, and the volatile materials were removed under reduced pressure. Pentane (20 mL) was added, the solution was filtered, and the pentane was removed under reduced pressure to leave a white solid. This solid was washed with a small quantity of pentane to yield 0.077 g (10%) of a white solid, 1H NMR (C$_6$D$_6$): δ 2.08 (6H), 1.30 (9H), 0.44 (6H).

When ethylene was polymerized substantially according to the procedure of Example 7, a small amount of polyethylene was recovered.

COMPARATIVE 1

The polymerization procedure of Example 105 was substantially followed except that the catalyst was pentamethylcyclooentadienyltitanium trichloride. The polymer yield was 4.6 g.

COMPARATIVE 2

The polymerization procedure of Example 97 was substantially followed except that the catalyst was (tert-butylamido)pentamethyl-η$^5$-cyclopentadienyltitanium dichloride ($^1$H NMR (C$_6$D$_6$): δ 2.07 (s, 1H), 1.88 (s, 15H), 1.35 (s, 9H). $^{13}$C NMR (C$_6$D$_6$): δ 61.0, 31.3, 12.6). The polymer yield was 2.0 g.

COMPARATIVE 3

The polymerization procedure of Example 105 was substantially followed except that the catalyst was bis-(tert-butylamido)dimethylsilanetitanium dichloride. No polymer was observed after 10 minutes of reaction.

COMPARATIVE 4

The polymerization procedure of Example 105 was substantially followed except that the catalyst was dicyclopentadienylzirconium dichloride. The polymer yield was 109.0 g, Mw=16,300, Mw/Mn=3.63, melt index ASTM D-1238 Procedure A, condition E, I$_2$, was greater than 1,000 indicating a very low molecular weight polymer.

COMPARATIVE 5

The polymerization procedure of Example 105 was substantially followed except that the catalyst was dicyclopentadienyltitanium dichloride. The polymer yield was 7.3 g, melt index, ASTM D-1238 Procedure A, condition E, I$_2$, was greater than 1,000 indicating a very low molecular weight polymer.

What is claimed is:

1. A copolymer according to formula

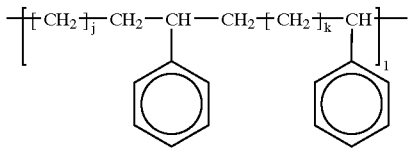

where j, k, and l ≥ 1 prepared by polymerizing a monomer mixture comprising ethylene and styrene in the presence of a catalyst comprising the following components:
a) a metal coordination complex corresponding to the formula:

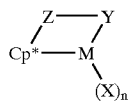

wherein:
M is a metal of Group 4 or the Lanthanide Series of the Periodic Table of the Elements;
Cp* is a cyclopentadienyl or a substituted cyclopentadienyl group wherein one or more carbons of the cyclopentadienyl group are substituted with a C$_{1-20}$ hydrocarbyl radical, C$_{1-20}$ halohydrocarbyl radical, C$_{1-20}$ hydrocarbyl substituted Group 14 metalloid radical, or halogen radical, or optionally two or more such substituents together form a fused ring system; said Cp* being bound in an η$^5$ bonding mode to M;
Z is a moiety comprising boron, or a member of Group 14 of the Periodic Table of the Elements, and optionally sulfur or oxygen, said moiety having up to 20 non-hydrogen atoms, and optionally Cp* and Z together form a fused ring system;
X independently each occurrence is an anionic ligand group having up to 30 non-hydrogen atoms;
n is 1 or 2 depending on the valence of M; and
Y is an anionic ligand group bonded to Z and M comprising nitrogen, phosphorus, oxygen or sulfur and having up to 20 non-hydrogen atoms, optionally Y and Z together form a fused ring system; and
b) an activating cocatalyst.

2. A copolymer according to claim 1 having a weight average molecular weight (M$_w$) greater than 13,000 having a structure according to formula

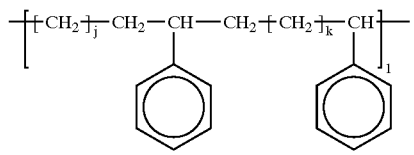

where j, k, and l ≥ 1 comprising ethylene and at least 1.0 mole percent of styrene monomer.

3. A copolymer according to claim 2 that is elastomeric.

4. A copolymer according to claim 1, comprising from 1.5 to 50 mole percent styrene monomer content.

5. A copolymer according to claim 1, comprising from 5.0 to 48 mole percent styrene monomer content.

6. A copolymer according to claim 1, comprising from 8.0 to 47 mole percent styrene monomer content.

7. A copolymer according to claim 1, having Mw greater than 20,000 and a melt index (I$_2$) from 0.01 to 100.

8. A copolymer according to claim 7, having Mw greater than 30,000 and a melt index (I2) from 0.1 to 10.

9. A copolymer according to claim 1, wherein the catalyst additionally comprises a support.

10. A copolymer according to claim 2 in the form of a film.

11. A copolymer according to claim 2, wherein said copolymer is less Newtonian than linear polyethylene resins of similar olefin content.

12. A copolymer according to claim 1, wherein said copolymer is less Newtonian than linear polyethylene resins of similar olefin content.

* * * * *